(12) United States Patent
Nguyen et al.

(10) Patent No.: US 7,863,283 B2
(45) Date of Patent: Jan. 4, 2011

(54) SULPHOXIMINE-SUBSTITUTED QUINAZOLINE DERIVATIVES AS IMMUNO-MODULATORS, THEIR PREPARATION AND USE AS MEDICAMENTS

(75) Inventors: Duy Nguyen, Berlin (DE); Arne von Bonin, Glienicke/Nordbahn (DE); Michael Haerter, Leverkusen (DE); Hartmut Schirok, Wuppertal (DE); Anne Mengel, Berlin (DE); Martina Schaefer, Berlin (DE); Oliver von Ahsen, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 48 days.

(21) Appl. No.: 12/138,879

(22) Filed: Jun. 13, 2008

(65) Prior Publication Data

US 2009/0186911 A1 Jul. 23, 2009

Related U.S. Application Data

(60) Provisional application No. 61/039,621, filed on Mar. 26, 2008.

(30) Foreign Application Priority Data

Jan. 17, 2008 (EP) .................................. 08075043

(51) Int. Cl.
*A61K 31/517* (2006.01)
(52) U.S. Cl. ................. 514/266.3; 514/266.4; 544/287; 544/293

(58) Field of Classification Search ................. 544/287, 544/293
See application file for complete search history.

(56) References Cited

FOREIGN PATENT DOCUMENTS

| WO | 9813354 A1 | 4/1998 |
| WO | 0121595 A1 | 3/2001 |
| WO | 2006099974 A1 | 9/2006 |
| WO | PCTEP2008005045 R | 9/2008 |

OTHER PUBLICATIONS

Hennequin, Laurent F., et al. "Design and Structure-Activity Relationship of a New Class of Potent VEGF Receptor Tyrosine Kinase Inhibitors." Journal of Medicinal Chemistry (1999): vol 42, No. 26.

*Primary Examiner*—James O Wilson
*Assistant Examiner*—Brian McDowell
(74) *Attorney, Agent, or Firm*—Millen, White, Zelano & Branigan, P.C.

(57) ABSTRACT

The present invention relates to sulphoximine-substituted quinazoline derivatives of the formula (I), processes for their preparation and their use as a medicament for the treatment of various diseases.

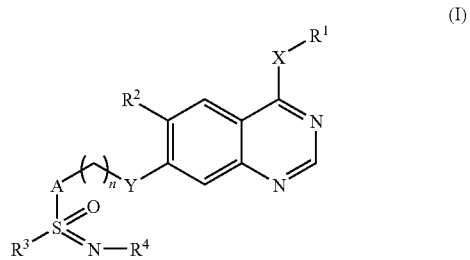

23 Claims, No Drawings

SULPHOXIMINE-SUBSTITUTED QUINAZOLINE DERIVATIVES AS IMMUNO-MODULATORS, THEIR PREPARATION AND USE AS MEDICAMENTS

This application claims the benefit of the filing date of U.S. Provisional Application Ser. No. 61/039,621 filed Mar. 26, 2008.

The present invention relates to sulphoximine-substituted quinazoline derivatives, processes for their preparation, and their use as a medicament for the treatment of various diseases.

BIOLOGICAL BACKGROUND

An over-reacting immune system is co-responsible for numerous chronic inflammatory diseases, such as, for example, rheumatoid arthritis, Crohn's disease, asthma and multiple sclerosis. Owing to an increased release of proinflammatory cytokines, damage to endogenous tissue structures results. The interplay of the innate and adaptive immune system is of central importance in this context (Akira et al., 2001). Modulation of the immune system by substances which interfere with the activation of cells of the innate and/or of the adaptive immune system has an anti-inflammatory action and can thus attenuate the pathological phenotype in the diseases mentioned by way of example above.

Innate immunity is based on the fact that microorganisms such as bacteria and viruses have certain inherent features by means of which they are recognized by the immune system and subsequently activate. Certain pathogen-associated molecular patterns (PAMPs) are recognized. PAMPs are recognized by the pattern recognition receptors (PRR), which also include toll-like receptors (TLR) (Janeway and Medzhitov, 2002). TLRs are homologues of the *Drosophila* receptor protein toll. Humans have ten different TLRs. TLR one and six are co-receptors for TLR2. TLR2 recognizes, inter alia, lipoproteins and lipopeptides. TLR3 recognizes double-stranded RNA. TLR4 recognizes, inter alia, LPS of gram-negative bacteria and lipoteichoic acid of gram-positive bacteria. TLR5 recognizes flagellin. TLR9 recognizes CpG motifs in bacterial DANN (O'Neill, 2006). Co-receptors can further modify the recognition capabilities of TLRs (Jiang et al., 2005).

IL-1/-18, TLR Signal Transduction

TLRs are related to IL-1/IL-18 cytokine receptors in signal transmission. IL-1 ("endogenous pyrogen") strongly stimulates inflammation and induces fever. Members of the IL-1R/TLR superfamily have a TIR domain (toll/IL1 receptor). The TIR domain is approximately 200 amino acids long and contains three conserved sequence motifs. Proteins bearing TIR domains bind by means of a protein-protein interaction (O'Neill et al., 2005). The subclass one (IL-1R family) contains three Ig-like domains; the receptor is a heterodimer. These include the IL-1 receptors one and two, the co-receptor IL-1RAcP and the corresponding proteins of the IL-18 system. The subclass two (TLR family) contains leucine-rich motifs. Toll-like receptors form homo- or heterodimers.

After activation of the TLR or IL-1, -18 receptors by the appropriate ligands, a multistage signal cascade is set in motion. The TLR or IL-1/-18 receptor complex interacts with the adaptor protein MyD88 by means of TIR/TIR contacts. The IL-1 associated receptor kinase (IRAK-1) normally has Tollip (toll interacting protein) bound, which probably acts as an alleviating molecule ("silencer"). IRAK/Tollip binds to the active TLR/IL-1R complex. MyD88 displaces Tollip whereby IRAK1 and IRAK-4 are activated, very highly probably as a dimer by transphosphorylation. Active IRAK leaves the receptor and binds in the cytoplasm to the adapter molecule TRAF (Barton and Medzhitov, 2003). By means of TRAF, further proteins are ubiquitinylated. By means of an unknown mechanism, Ub-TRAF leads to the autophosphorylation of the S/T kinase TAK1 (a MAP kinase kinasekinase). TAK1 phosphorylates IκB (NF-κB activation) and MKK6. The latter is responsible for the activation of the MAP kinases p38 and JNK. NF-κB has been identified as a nuclear factor for the expression of the light antibody chain kappa in B cells, but is also involved in the regulation of many other genes. NF-κB is retained in the cytoplasm in the inactive state, where it is bound to the inhibitor IκB (Deng et al., 2000). Phosphorylation of IκB causes the inhibitor IkB to be proteolytically degraded and the transcription factor can migrate into the core. NF-κB is a heterodimer of the subunits p65 (Rel) and p50 (Bäuerle and Henkel, 1994). There are a number of members of this family which can interact in different ways. NF-κB on its own cannot induce transcription. For gene activation, transcriptional co-activators are necessary, such as, for example, p300 or CBT (Akira and Takeda, 2004).

The structures of the following patent applications form the structurally obvious prior art:

Benzyloxy-substituted quinazoline derivatives are mentioned in the following patent applications: WO 2006/076246 (Inhibitors of serine proteases), U.S. Pat. No. 5,962,458 (Inhibitors of VEGF receptor tyrosine kinase), U.S. Pat. No. 6,593,333 (Inhibitors of p38 kinase), U.S. Pat. No. 7,081,461 (Inhibitors of Aurora 2 kinase), WO 2004/105765 (Inhibitors of receptor tyrosine kinases), WO 2004/94410 (Inhibitors of Aurora A and/or Aurora B kinase). However, sulphoximine substituents for the benzyloxy radical are not disclosed. Alkoxy-substituted quinazoline derivatives are mentioned in the following patent applications: US 2006/0142570 (Kinase inhibitors), WO 2006/066795 (Kinase inhibitors), US 2005/0101617 (ERB2 and EGFR inhibitors), WO 2005/013998 (Inhibitors of VEGF receptor tyrosine kinase), WO 2004/046101 (ERB2 and EGFR inhibitors), WO 2003/082831 (Inhibitors of ERB receptor tyrosine kinase), WO 2001/077085 (Inhibitors of VEGF receptor tyrosine kinase), WO 2000/047212 (Inhibitors of VEGF receptor tyrosine kinase), WO 98/13354 (Inhibitors of VEGF receptor tyrosine kinase), WO 97/30035 (Inhibitors of VEGF receptor tyrosine kinase). However, sulphoximine substituents for the alkoxy radical are not disclosed.

Starting from this prior art, the object of the present invention consists in preparing further structures for therapy, in particular for immunomodulation.

The object is achieved by sulphoximine-substituted compounds of the general formula (I),

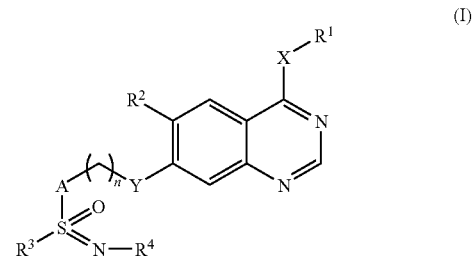

in which $R^1$ represents (i) a mono- or polysubstituted aryl or heteroaryl ring optionally identically or differently substituted by hydroxyl, $-NR^7R^8$, $-NR^6-C(O)-R^{12}$, $-NR^6-C(O)-OR^{11}$, $-NR^6-C(O)-NR^7R^8$, $-NR^7-SO_2-$ $R^{11}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, or (ii) a $C_1$-$C_6$-alkyl, $C_2$-$C_6$-alkenyl or $C_2$-$C_6$-alkynyl radical optionally identically or differently mono- or polysubstituted by hydroxyl, —$NR^7R^8$, —$NR^6$—$C(O)R^{11}$, —$NR^6$—$C(O)$—$OR^{11}$, —$NR^6$—$C(O)$—$NR^7R^8$, —$NR^6$—$SO_2$—$R^{11}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, or (iii) a $C_3$-$C_8$ cycloalkyl or heterocyclyl ring having 3 to 8 ring atoms and optionally identically or differently mono- or polysubstituted by hydroxyl, —$NR^7R^8$, —$NR^6$—$C(O)$—$R^{11}$, —$NR^6$—$C(O)$—$OR^{11}$, —$NR^6$—$C(O)$—$NR^7R^8$, —$NR^6$—$SO_2$—$R^{11}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, $R^2$ represents
(i) hydrogen,
(ii) hydroxyl, halogen, cyano, nitro, —$CF_3$, —$OCF_3$, —$C(O)OR^{11}$, —$C(O)OH$, —$C(O)NR^7R^8$, —$C(S)NR^7R^8$, —$NR^7R^8$, —$NR^6$—$C(O)$—$R^{11}$, —$NR^6$—$C(O)$—$OR^{11}$, —$NR^6$—$C(O)$—$NR^7R^8$, —$NR^6$—$SO_2$—$R^{11}$, or
(iii) a $C_1$-$C_6$-alkyl or $C_1$-$C_6$-alkoxy radical optionally identically or differently mono- or polysubstituted by halogen, hydroxyl, $C_1$-$C_6$-alkoxy, —$CF_3$, —$OCF_3$ or —$NR^7R^8$, or
(iv) a $C_3$-$C_8$-cycloalkyl ring optionally identically or differently mono- or polysubstituted by halogen, hydroxyl, $C_1$-$C_6$-alkoxy, —$CF_3$, —$OCF_3$, —$NR^7R^8$ and/or $C_1$-$C_6$-alkyl, $R^3$ represents
a $C_1$-$C_6$-alkyl, $C_2$-$C_6$-alkenyl or $C_2$-$C_6$-alkynyl radical, a $C_3$-$C_7$-cycloalkyl or aryl ring, a heterocyclyl ring having 3 to 8 ring atoms or a monocyclic heteroaryl ring, in each case itself optionally identically or differently mono- or polysubstituted by hydroxyl, —$C(O)OR^{11}$, —$C(O)NR^7R^8$, —$NR^7R^8$, cyano, halogen, —$CF_3$, $C_1$-$C_6$-alkoxy, —$OCF_3$ and/or $C_1$-$C_6$-alkyl, $R^4$ represents
hydrogen, —$SO_2R^{11}$, —$C(O)R^{11}$, —$C(O)OR^{11}$, —$C(O)NR^7R^8$, —$C(S)OR^{11}$, —$C(S)NR^7R^8$ or —$R^{11}$, X, Y independently of one another represents —$O$— or the group —$NR^5$—, A represents
(i) a bond or
(ii) an aryl or heteroaryl ring optionally identically or differently mono- or polysubstituted by hydroxyl, —$NR^7R^8$, —$NR^6$—$C(O)$—$R^{11}$, —$C(O)NR^7R^8$, —$NR^6$—$C(O)$—$OR^{11}$, —$NR^6$—$C(O)$—$NR^7R^8$, —$NR^6$—$SO_2$—$R^{11}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, n represents 1-6, $R^5$ represents
(i) hydrogen,
(ii) a $C_1$-$C_6$-alkyl radical, $C_3$-$C_8$-cycloalkyl or aryl ring, a heterocyclyl ring having 3 to 8 ring atoms or a heteroaryl ring, or
(iii) —$C(O)$—$(C_1$-$C_6)$-alkyl, —$C(O)$-phenyl, or —$C(O)$-benzyl, (ii) and (iii) optionally being identically or differently mono- or polysubstituted by hydroxyl, —$NR^9R^{10}$, cyano, halogen, —$CF_3$, $C_1$-$C_6$-alkoxy and/or —$OCF_3$, or, if X represents —$NR^5$—, alternatively X, $R^1$ and $R^5$ together form a 3- to 8-membered ring which optionally, in addition to the nitrogen atom, contains one or more further heteroatoms, is optionally identically or differently mono- or polysubstituted by hydroxyl, $C_1$-$C_6$-alkyl, $C_1$-$C_6$-alkoxy, —$C(O)R^{11}$, —$SO_2R^{11}$, halogen or the group —$NR^8R^9$, optionally contains 1 to 3 double bonds and/or is optionally interrupted by one or more —$C(O)$— groups, $R^6$ represents hydrogen or a $C_1$-$C_6$-alkyl radical, $R^7$ and $R^8$ independently of one another represent
(i) hydrogen and/or
(ii) a $C_1$-$C_6$-alkyl radical, $C_2$-$C_6$-alkenyl, $C_3$-$C_8$-cycloalkyl and/or aryl ring, a heterocyclyl ring having 3 to 8 ring atoms and/or a heteroaryl ring, are optionally identically or differently mono- or polysubstituted by hydroxyl, —$NR^9R^{10}$, cyano, halogen, —$CF_3$, $C_1$-$C_6$-alkoxy and/or —$OCF_3$, or $R^7$ and $R^8$ together with the nitrogen atom form a 5- to 7-membered ring, which optionally, in addition to the nitrogen atom, contains 1 or 2 further heteroatoms and which can be identically or differently mono- or polysubstituted by hydroxyl, —$NR^9R^{10}$, cyano, halogen, —$CF_3$, $C_1$-$C_6$-alkyl, $C_1$-$C_6$-alkoxy and/or —$OCF_3$, $R^9$ and $R^{10}$ independently of one another represent hydrogen or a $C_1$-$C_6$-alkyl radical which is optionally identically or differently mono- or polysubstituted by hydroxyl, $R^{11}$ represents a $C_1$-$C_6$-alkyl, $C_2$-$C_6$-alkenyl or $C_2$-$C_6$-alkynyl radical, a $C_3$-$C_8$-cycloalkyl or aryl ring, a heterocyclyl ring having 3 to 8 ring atoms or a heteroaryl ring, in each case optionally itself identically or differently mono- or polysubstituted by hydroxyl, halogen, cyano, nitro, —$NR^7R^8$, $C_1$-$C_6$-alkyl , —$CF_3$, $C_1$-$C_6$-alkoxy and/or —$OCF_3$, and their salts, diastereomers and enantiomers.

The following definitions underlie the invention:

$C_n$-Alkyl:

Monovalent, straight-chain or branched, saturated hydrocarbon radical having n carbon atoms.

A $C_1$-$C_6$ alkyl radical comprises, inter alia, for example: methyl-, ethyl-, propyl-, butyl-, pentyl-, hexyl-, iso-propyl-, iso-butyl-, sec-butyl, tert-butyl-, iso-pentyl-, 2-methylbutyl-, 1-methylbutyl-, 1-ethylpropyl-, 1,2-dimethylpropyl, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-.

A methyl, ethyl, propyl or isopropyl radical is preferred.

$C_n$-Alkenyl:

Monovalent, straight-chain or branched hydrocarbon radical having n carbon atoms and at least one double bond.

A $C_2$-$C_6$ alkenyl radical comprises, inter alia, for example: vinyl-, allyl-, (E)-2-methylvinyl-, (Z)-2-methylvinyl-, homoallyl-, (E)-but-2-enyl-, (Z)-but-2-enyl-, (E)-but-1-enyl-, (Z)-but-1-enyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, isopropenyl-, 2-methylprop-2-enyl-, 1-methylprop-2-enyl-, 2-methylprop-1-enyl-, (E)-1-methylprop-1-enyl-, (Z)-1-methylprop-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1- enyl-, (Z)-1-methylbut-1-enyl-, 1,1-dimethylprop-2-enyl-, 1-ethylprop-1-enyl-, 1-propylvinyl-, 1-isopropylvinyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethyl-but-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-,(E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, (E)-3,3-dimethylprop-1-enyl-, (Z)-3,3-dimethylprop-1-enyl-, 1-(1,1-dimethylethyl)ethenyl.

A vinyl or allyl radical is preferred.

$C_n$-Alkynyl:

Monovalent, straight-chain or branched hydrocarbon radical having n carbon atoms and at least one triple bond.

A $C_2$-$C_6$ alkynyl radical comprises, inter alia, for example: ethynyl-, prop-1-ynyl-, prop-2-ynyl-, but-1-ynyl-, but-2-ynyl-, but-3-ynyl-, pent-1-ynyl-, pent-2-ynyl-, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-di-methylbut-2-ynyl- or a 3,3-dimethylbut-1-ynyl-.

An ethynyl-, prop-1-ynyl- or prop-2-ynyl- radical is preferred.

$C_n$-Cycloalkyl:

Monovalent, cyclic hydrocarbon ring having n carbon atoms.

$C_3$-$C_7$-Cycloalkyl ring comprises:

cyclopropyl, cyclobutyl, cyclopentyl, cyclohexyl and cycloheptyl.

A cyclopropyl, cyclobutyl, cyclopentyl or a cyclohexyl ring is preferred.

$C_n$-Alkoxy:

Straight-chain or branched $C_n$-alkyl ether radical of the formula —OR with R=alkyl.

Aryl

Aryl is a monovalent, aromatic ring system without a heteroatom.

$C_6$-aryl is equal to phenyl. $C_{10}$-aryl ist equal to naphthyl.

Unless stated otherwise, aryl comprises only phenyl and napthyl.

Phenyl is preferred.

Heteroatoms

Heteroatoms are to be understood as meaning oxygen, nitrogen or sulphur atoms.

Heteroaryl

Heteroaryl is a monovalent, aromatic ring system having at least one heteroatom different from a carbon. Heteroatoms which can occur are nitrogen atoms, oxygen atoms and/or sulphur atoms. The bond valency can be on any desired aromatic carbon atom or on a nitrogen atom.

Unless stated otherwise, heteroaryl comprises only monocyclic and bicyclic rings.

A monocyclic heteroaryl ring according to the present invention has 5 or 6 ring atoms.

Heteroaryl rings having 5 ring atoms comprise, for example, the rings:

thienyl, thiazolyl, furanyl, pyrrolyl, oxazolyl, imidazolyl, pyrazolyl, isoxazolyl, isothiazolyl, oxadiazolyl, triazolyl, tetrazolyl and thiadiazolyl.

Heteroaryl rings having 6 ring atoms comprise, for example, the rings:

pyridyl, pyridazinyl, pyrimidinyl, pyrazinyl and triazinyl.

A bicyclic heteroaryl ring according to the present invention has 9 or 10 ring atoms.

Heteroaryl rings having 9 ring atoms comprise, for example, the rings:

phthalidyl, thiophthalidyl, indolyl, isoindolyl, indazolyl, benzothiazolyl, indolonyl, isoindolonyl, benzofuranyl, benzothienyl, benzimidazolyl, benzoxazolyl, azocinyl, indolizinyl, purinyl.

Heteroaryl rings having 10 ring atoms comprise, for example, the rings: isoquinolinyl-, quinolinyl-, benzoxazinonyl-, phthalazinonyl, quinolonyl-, isoquinolon-yl-, quinazolinyl-, quinoxalinyl-, cinnolinyl-, phthalazinyl-, 1,7- or 1,8-naphthyridinyl-, quinolinyl-, isoquinolinyl-, quinazolinyl- or quinoxalinyl-.

Monocyclic heteroaryl rings having 5 or 6 ring atoms are preferred.

Heterocyclyl

Heterocyclyl within the meaning of the invention is a completely hydrogenated heteroaryl (completely hydrogenated heteroaryl=saturated heterocyclyl), i.e. a non-aromatic ring system having at least one heteroatom different from a carbon.

Heteroatoms which can occur are nitrogen atoms, oxygen atoms and/or sulphur atoms. The bond valency can be on any desired carbon atom or on a nitrogen atom.

Heterocyclyl ring having 3 ring atoms comprises, for example:

aziridinyl.

Heterocyclyl ring having 4 ring atoms comprises, for example:

azetidinyl, oxetanyl.

Heterocyclyl rings having 5 ring atoms comprise, for example, the rings:

pyrrolidinyl, imidazolidinyl, pyrazolidinyl and tetrahydrofuranyl.

Heterocyclyl rings having 6 ring atoms comprise, for example, the rings:

piperidinyl, piperazinyl, morpholinyl, tetrahydropyranyl and thiomorpholinyl

Heterocyclyl ring having 7 ring atoms comprises, for example:

azepanyl, oxepanyl, [1,3]-diazepanyl, [1,4]-diazepanyl.

Heterocyclyl ring having 8 ring atoms comprises, for example:

oxocanyl, azocanyl

Unless stated otherwise, heterocyclyl denotes a heterocyclyl ring having 3 to 8 ring atoms.

Halogen

The designation halogen comprises fluorine, chlorine, bromine and iodine.

Compounds of the general formula (I) form a preferred subgroup, in which $R^1$ represents
  (i) an aryl or heteroaryl ring optionally identically or differently mono- or polysubstituted by hydroxyl, —$NR^7R^8$, cyano, halogen, $C_1$-$C_6$-alkoxy, —$NR^6$—C(O)$R^{11}$, —$OCF_3$, —$CF_3$, $C_1$-$C_6$-alkyl, or
  (ii) a $C_1$-$C_6$-alkyl radical optionally identically or differently mono- or polysubstituted by hydroxyl, —$NR^7R^8$, cyano, halogen, $C_1$-$C_6$-alkoxy, —$NR^6$—C(O)$R^{11}$, —$OCF_3$, —$CF_3$, $C_1$-$C_6$-alkyl, or
  (iii) a $C_3$-$C_8$ cycloalkyl or heterocyclyl ring having 3 to 8 ring atoms and optionally identically or differently mono- or polysubstituted by hydroxyl, —$NR^7R^8$, cyano, halogen, $C_1$-$C_6$-alkoxy, —$OCF_3$, —$CF_3$, $C_1$-$C_6$-alkyl, $R^2$ represents hydrogen, halogen, cyano, —C(O)$OR^{11}$, —C(O)OH, —C(O)$NR^7R^8$ or a $C_1$-$C_6$-alkyl or $C_1$-$C_6$-alkoxy radical optionally identically or differently mono- or polysubstituted by halogen, hydroxyl, $C_1$-$C_6$-alkoxy, —$CF_3$, —$OCF_3$ or —$NR^7R^8$ $R^3$ represents a $C_1$-$C_6$-alkyl radical or a $C_3$-$C_7$-cycloalkyl ring, optionally itself identically or differently mono- or polysubstituted by hydroxyl, —C(O)$OR^{11}$, —C(O)$NR^7R^8$, —$NR^7R^8$, cyano, halogen, —$CF_3$, $C_1$-$C_6$-alkoxy, —$OCF_3$ and/or $C_1$-$C_6$-alkyl, $R^4$ represents
  hydrogen, —$SO_2R^{11}$, —C(O)$OR^{11}$, —C(O)$NR^7R^8$, X represents the group —$NR^5$—, Y represents —O— or the group $NR^5$, A represents
  (i) a bond or
  (ii) an aryl or heteroaryl ring optionally identically or differently mono- or polysubstituted by hydroxyl, —$NR^7R^8$, —C(O)$NR^7R^8$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, n represents 1-5, $R^5$ represents hydrogen, a $C_1$-$C_6$-alkyl radical, a $C_3$-$C_8$-cycloalkyl ring or —C(O)—($C_1$-$C_6$)-alkyl, are in each case optionally identically or differently mono- or polysubstituted by hydroxyl, —$NR^9R^{10}$, cyano, halogen, —$CF_3$, $C_1$-$C_6$-alkoxy and/or —$OCF_3$, $R^7$ and $R^8$ independently of one another represent
  (i) hydrogen and/or
  (ii) a $C_1$-$C_6$-alkyl radical, a $C_3$-$C_8$-cycloalkyl and/or aryl ring, a heterocyclyl ring having 3 to 8 ring atoms and/or a heteroaryl ring, are optionally identically or differently mono- or polysubstituted by hydroxyl, —$NR^9R^{10}$, cyano, halogen, —$CF_3$, $C_1$-$C_6$-alkoxy and/or —$OCF_3$, $R^{11}$ represents a $C_1$-$C_3$-alkyl, a $C_3$-$C_8$-cycloalkyl or aryl ring, a heterocyclyl ring having 3 to 8 ring atoms or a heteroaryl ring, in each case optionally itself identically or differently mono- or polysubstituted by hydroxyl, halogen, cyano, nitro, —$NR^7R^8$, $C_1$-$C_6$-alkyl, —$CF_3$, $C_1$-$C_6$-alkoxy and/or —$OCF_3$, and their salts, diastereomers and enantiomers.

Compounds of the general formula (I) form a particularly preferred subgroup, in which $R^1$ represents an aryl or heteroaryl ring optionally substituted by hydroxyl, or represents a $C_1$-$C_6$-alkyl radical or $C_3$-$C_8$ cycloalkyl ring optionally identically or differently mono- or polysubstituted by —$NR^7R^8$ or $C_1$-$C_6$-alkoxy $R^2$ represents hydrogen, halogen, —C(O)$OR^{11}$, —C(O)OH or a $C_1$-$C_6$-alkoxy radical, $R^3$ represents a $C_1$-$C_3$-alkyl radical $R^4$ represents hydrogen, —$SO_2R^{11}$ or —C(O)$OR^{11}$, X represents —NH—, Y represents —O—, A represents a bond or an aryl ring, n represents 1-4, $R^7$ and $R^8$ independently of one another represent a $C_1$-$C_6$-alkyl radical $R^{11}$ represents a $C_1$-$C_3$-alkyl radical or an aryl ring, in each case optionally itself substituted by nitro, and their salts, diastereomers and enantiomers.

Compounds of the general formula (I) form a likewise particularly preferred subgroup, in which $R^1$ represents
  (i) a phenyl or monocyclic heteroaryl ring optionally identically or differently mono- or polysubstituted by hydroxyl, —$NR^6$—C(O)—$R^{11}$, cyano, $C_1$-$C_6$-alkyl, or
  (ii) a $C_1$-$C_6$-alkyl radical optionally identically or differently mono or polysubstituted by hydroxyl, —$NR^7R^8$, $C_1$-$C_6$-alkoxy and/or $C_3$-$C_6$-cycloalkyl, or
  (iii) a $C_3$-$C_8$ cycloalkyl ring.

$R^2$ represents hydrogen, halogen, cyano, —C(O)$OR^{11}$, —C(O)OH, or a $C_1$-$C_6$-alkoxy radical, $R^3$ represents a $C_1$-$C_6$-alkyl radical $R^4$ represents hydrogen, —$SO_2R^{11}$ or —C(O)$OR^{11}$, X represents —NH—, Y represents —O—, or —NH—

A represents a bond or a phenyl or monocyclic heteroaryl ring, n represents 1-4, $R^6$ represents hydrogen, $R^7$ and $R^8$ represent a $C_1$-$C_6$-alkyl radical, $R^{11}$ represents a $C_1$-$C_6$-alkyl radical or phenyl ring, in each case optionally itself substituted by nitro, and their salts, diastereomers and enantiomers.

In the general formula (I), $R^1$ can represent
(i) an aryl or heteroaryl ring optionally identically or differently mono- or polysubstituted by hydroxyl, —$NR^7R^8$, —$NR^6$—C(O)—$R^{11}$, —$NR^6$—C(O)—$OR^{11}$, —$NR^6$—C(O)—$NR^7R^8$, —$NR^7$—$SO_2$—$R^{11}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, or
(ii) a $C_1$-$C_6$-alkyl, $C_2$-$C_6$-alkenyl or $C_2$-$C_6$-alkynyl radical, optionally identically or differently mono- or polysubstituted by hydroxyl, —$NR^7R^8$, —$NR^6$—C(O)$R^{11}$, —$NR^6$—C(O)—$OR^{11}$, —$NR^6$—C(O)—$NR^7R^8$, —$NR^6$—$SO_2$—$R^{11}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, or
(iii) a $C_3$-$C_8$ cycloalkyl or heterocyclyl ring having 3 to 8 ring atoms and optionally identically or differently mono- or polysubstituted by hydroxyl, —$NR^7R^8$, —$NR^6$—C(O)—$R^{11}$, —$NR^6$—C(O)—$OR^{11}$, —$NR^6$—C(O)—$NR^7R^8$, —$NR^6$—$SO_2$—$R^{11}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms.

Preferably, $R^1$ represents
(i) an aryl or heteroaryl ring optionally identically or differently mono- or polysubstituted by hydroxyl, —$NR^7R^8$, cyano, halogen, $C_1$-$C_6$-alkoxy, —$NR^6$—$C(O)R^{11}$, —$OCF_3$, —$CF_3$, $C_1$-$C_6$-alkyl, or (ii) a $C_1$-$C_6$-alkyl radical optionally identically or differently mono- or polysubstituted by hydroxyl, —$NR^7R^8$, cyano, halogen, $C_1$-$C_6$-alkoxy, —$NR^6$—$C(O)R^{11}$, —$OCF_3$, —$CF_3$, $C_1$-$C_6$-alkyl, or (iii) a $C_3$-$C_8$ cycloalkyl or heterocyclyl ring having 3 to 8 ring atoms and optionally identically or differently mono- or polysubstituted by hydroxyl, —$NR^7R^8$, cyano, halogen, $C_1$-$C_6$-alkoxy, —$OCF_3$, —$CF_3$, $C_1$-$C_6$-alkyl.

Particularly preferably, $R^1$ represents:

(i) a phenyl or monocyclic heteroaryl ring optionally identically or differently mono- or polysubstituted by hydroxyl, —$NR^6$—$C(O)$—Rl, cyano, $C_1$-$C_6$-alkyl, or (ii) a $C_1$-$C_6$-alkyl radical optionally identically or differently mono- or polysubstituted by hydroxyl, —$NR^7R^8$, $C_1$-$C_6$-alkoxy and/or $C_3$-$C_6$-cycloalkyl, or (iii) a $C_3$-$C_8$ cycloalkyl ring.

Particularly preferably, $R^1$ also represents:

an aryl or heteroaryl ring optionally substituted by hydroxyl, or a $C_1$-$C_6$-alkyl radical or $C_3$-$C_8$ cycloalkyl ring optionally identically or differently mono- or polysubstituted by —$NR^7R^8$ or $C_1$-$C_6$-alkoxy.

In the general formula (1), $R^2$ can represent (i) hydrogen, (ii) hydroxyl, halogen, cyano, nitro, —$CF_3$, —$OCF_3$, —$C(O)OR^{11}$, —$C(O)OH$, —$C(O)NR^7R^8$, —$C(S)NR^7R^8$, —$NR^7R^8$, —$NR^6$—$C(O)$—$R^{11}$, —$NR^6$—$C(O)$—$OR^{11}$, —$NR^6$—$C(O)$—$NR^7R^8$, —$NR^6$—$SO_2$—$R^{11}$, or (iii) a $C_1$-$C_6$-alkyl or $C_1$-$C_6$-alkoxy radical optionally identically or differently mono- or polysubstituted by halogen, hydroxyl, $C_1$-$C_6$-alkoxy, —$CF_3$, —$OCF_3$ or —$NR^7R^8$, or (iv) a $C_3$-$C_8$-cycloalkyl ring optionally identically or differently mono- or polysubstituted by halogen, hydroxyl, $C_1$-$C_6$-alkoxy, —$CF_3$, —$OCF_3$, —$NR^7R^8$ and/or $C_1$-$C_6$-alkyl.

Preferably, $R^2$ represents:

hydrogen, halogen, cyano, —$C(O)OR^{11}$, —$C(O)OH$, —$C(O)NR^7R^8$ or a $C_1$-$C_6$-alkyl or $C_1$-$C_6$-alkoxy radical optionally identically or differently mono- or polysubstituted by halogen, hydroxyl, $C_1$-$C_6$-alkoxy, —$CF_3$, —$OCF_3$ or —$NR^7R^8$.

Particularly preferably, $R^2$ represents:

hydrogen, halogen, cyano, —$C(O)OR^{11}$, —$C(O)OH$ or a $C_1$-$C_6$-alkoxy radical.

Particularly preferably, $R^2$ also represents hydrogen, halogen, —$C(O)OR^{11}$, —$C(O)OH$ or a $C_1$-$C_6$-alkoxy radical.

In the general formula (1), $R^3$ can represent a $C_1$-$C_6$-alkyl, $C_2$-$C_6$-alkenyl or $C_2$-$C_6$-alkynyl radical, a $C_3$-$C_7$-cycloalkyl or aryl ring, a heterocyclyl ring having 3 to 8 ring atoms or a monocyclic heteroaryl ring, in each case optionally itself identically or differently mono- or polysubstituted by hydroxyl, —$C(O)OR^{11}$, —$C(O)NR^7R^8$, —$NR^7R^8$, cyano, halogen, —$CF_3$, $C_1$-$C_6$-alkoxy, —$OCF_3$ and/or $C_1$-$C_6$-alkyl.

Preferably, $R^3$ represents a $C_1$-$C_6$-alkyl radical or a $C_3$-$C_7$-cycloalkyl ring, optionally itself identically or differently mono- or polysubstituted by hydroxyl, —$C(O)OR^{11}$, —$C(O)NR^7R^8$, —$NR^7R^8$, cyano, halogen, —$CF_3$, $C_1$-$C_6$-alkoxy, —$OCF_3$ and/or $C_1$-$C_6$-alkyl, Particularly preferably, $R^3$ represents a $C_1$-$C_3$-alkyl radical In the general formula (I) $R^4$ can represent hydrogen, —$SO_2R^{11}$, —$C(O)R^{11}$, —$C(O)OR^{11}$, —$C(O)NR^7R^8$, —$C(S)OR^{11}$, —$C(S)NR^7R^8$ or —$R^{11}$, Preferably, $R^4$ represents hydrogen, —$SO_2R^{11}$, —$C(O)OR^{11}$ or —$C(O)NR^7R^8$ Particularly preferably, $R^4$ represents:

hydrogen, —$SO_2R^{11}$ or —$C(O)OR^{11}$

In the general formula (I), X and Y independently of one another represent:

—O— or the group —$NR^5$—.

Preferably, X represents the group —$NR^5$—.

Particularly preferably, X represents —NH—.

Preferably, Y represents —O—, or the group —$NR^5$—.

Particularly preferably, Y represents —O— or —NH—.

Exceptionally preferably, Y represents —O—.

In the general formula (I), A can represent (i) a bond or (ii) an aryl or heteroaryl ring optionally identically or differently mono- or polysubstituted by hydroxyl, —$NR^7R^8$, —$NR^6$—$C(O)$—$R^{11}$—$C(O)NR^7R^8$, —$NR^6$—$C(O)$—$OR^{11}$, —$NR^6$—$C(O)$—$NR^7R^8$, —$NR^6$—$SO_2$—$R^{11}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms.

Preferably, A represents:

(i) a bond or (ii) an aryl or heteroaryl ring optionally identically or differently mono- or polysubstituted by hydroxyl, —$NR^7R^8$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, Particularly preferably, A represents:

a bond or a phenyl or monocyclic heteroaryl ring.

Particularly preferably, A also represents:

a bond or a phenyl ring.

In the general formula (I), n can represent 1-6.

Preferably, n represents 1-5.

Particularly preferably, n represents 1-4.

In the general formula (I), $R^5$ can represent (i) hydrogen, (ii) a $C_1$-$C_6$-alkyl radical, $C_3$-$C_8$-cycloalkyl or aryl ring, a heterocyclyl ring having 3 to 8 ring atoms or a heteroaryl ring, or (iii) —$C(O)$—$(C_1$-$C_6)$-alkyl, —$C(O)$-phenyl, or —$C(O)$-benzyl, and (ii) and (iii) are optionally identically or differently mono- or polysubstituted by hydroxyl, —$NR^9R^{10}$, cyano, halogen, —$CF_3$, $C_1$-$C_6$-alkoxy and/or —$OCF_3$, or, if X represents —$NR^5$—, alternatively X, $R^1$ and $R^5$ together form a 3- to 8-membered ring which optionally, in addition to the nitrogen atom, contains one or more further heteroatoms, is optionally identically or differently mono- or polysubstituted by hydroxyl, $C_1$-$C_6$-alkyl, $C_1$-$C_6$-alkoxy, —$C(O)R^{11}$, —$SO_2R^{11}$, halogen or the group —$NR^8R^9$, optionally contains 1 to 3 double bonds and/or is optionally interrupted by one or more —$C(O)$— groups, Preferably, $R^5$ represents:

hydrogen, a $C_1$-$C_6$-alkyl radical, a $C_3$-$C_8$-cycloalkyl ring or —$C(O)$—$(C_1$-$C_6)$-alkyl, are in each case optionally identically or differently mono- or polysubstituted by hydroxyl, —$NR^9R^{10}$, cyano, halogen, —$CF_3$, $C_1$-$C_6$-alkoxy and/or —$OCF_3$.

In the general formula (I), $R^6$ can represent hydrogen or a $C_1$-$C_6$-alkyl radical.

Particularly preferably, $R^6$ represents hydrogen.

In the general formula (I), $R^7$ and $R^8$ independently of one another can represent (i) hydrogen and/or (ii) a $C_1$-$C_6$-alkyl radical, $C_2$-$C_6$-alkenyl, $C_3$-$C_8$-cycloalkyl and/or aryl ring, a heterocyclyl ring having 3 to 8 ring atoms and/or a heteroaryl ring, are optionally identically or differently mono- or polysubstituted by hydroxyl, —NR$^9$R$^{10}$, cyano, halogen, —CF$_3$, C$_1$-C$_6$-alkoxy and/or —OCF$_3$, or R$^7$ and R$^8$ together with the nitrogen atom form a 5- to 7-membered ring, which optionally in addition to the nitrogen atom contains 1 or 2 further heteroatoms and which can be identically or differently mono- or polysubstituted by hydroxyl, —NR$^9$R$^{10}$, cyano, halogen, —CF$_3$, C$_1$-C$_6$-alkyl, C$_1$-C$_6$-alkoxy and/or —OCF$_3$.

Preferably, R$^7$ and R$^8$ independently of one another represent:

(i) hydrogen and/or (ii) a C$_1$-C$_6$-alkyl radical, a C$_3$-C$_8$-cycloalkyl and/or aryl ring, a heterocyclyl ring having 3 to 8 ring atoms and/or a heteroaryl ring, are optionally identically or differently mono- or polysubstituted by hydroxyl, —NR$^9$R$^{10}$, cyano, halogen, —CF$_3$, C$_1$-C$_6$-alkoxy and/or —OCF$_3$.

Particularly preferably, R$^7$ and R$^8$ independently of one another represent:

a C$_1$-C$_6$-alkyl radical.

In the general formula (I), R$^9$ and R$^{10}$ independently of one another represent:

hydrogen or a C$_1$-C$_6$-alkyl radical, which is optionally identically or differently mono- or polysubstituted by hydroxyl, In the general formula (I), R$^{11}$ can represent for a C$_1$-C$_6$-alkyl, C$_2$-C$_6$-alkenyl or C$_2$-C$_6$-alkynyl radical, a C$_3$-C$_8$-cycloalkyl or aryl ring, a heterocyclyl ring having 3 to 8 ring atoms or a heteroaryl ring, in each case optionally itself identically or differently mono- or polysubstituted by hydroxyl, halogen, cyano, nitro, —NR$^7$R$^8$, C$_1$-C$_6$-alkyl, —CF$_3$, C$_1$-C$_6$-alkoxy and/or —OCF$_3$.

Preferably, R$^{11}$ represents a C$_1$-C$_3$-alkyl, a C$_3$-C$_8$-cycloalkyl or aryl ring, a heterocyclyl ring having 3 to 8 ring atoms or a heteroaryl ring, in each case optionally itself identically or differently mono- or polysubstituted by hydroxyl, halogen, cyano, nitro, —NR$^7$R$^8$, C$_1$-C$_6$-alkyl, —CF$_3$, C$_1$-C$_6$-alkoxy and/or —OCF$_3$.

Particularly preferably, R$^{11}$ represents:

for a C$_1$-C$_3$-alkyl radical or a phenyl ring, in each case optionally itself substituted by nitro.

All compounds which result by any possible combination of the abovementioned possible, preferred and particularly preferred meanings of the substituents are likewise to be regarded as covered by the present invention.

Particular embodiments of the invention moreover consist in compounds which result by combination of the meanings for the substituents directly disclosed in the examples.

The salts of the compounds are likewise to be regarded as covered by the present invention.

The formulation of the compounds according to the invention to give pharmaceutical preparations is carried out in a manner known per se, by converting the active compound or compounds into the desired administration form using the excipients customary in galenics.

Excipients which can be used here are, for example, vehicles, fillers, disintegrants, binders, moisturizers, lubricants, absorbents and adsorbents, diluents, solvents, cosolvents, emulsifiers, solubilizers, taste corrigents, colourants, preservatives, stabilizers, wetting agents, salts for changing the osmotic pressure or buffers. Reference is to be made here to Remington's Pharmaceutical Science, 15th ed. Mack Publishing Company, East Pennsylvania (1980).

The pharmaceutical formulations can be present in solid form, for example as tablets, coated tablets, pills, suppositories, capsules, transdermal systems or in semi-solid form, for example as ointments, creams, gels, suppositories, emulsions or in liquid form, for example as solutions, tinctures, suspensions or emulsions.

Excipients within the meaning of the invention can be, for example, salts, saccharides (mono-, di-, tri-, oligo-, and/or polysaccharides), proteins, amino acids, peptides, fats, waxes, oils, hydrocarbons and their derivatives, where the excipients can be of natural origin or can be obtained synthetically or partially synthetically.

Tablets, coated tablets, capsules, pills, powders, granules, pastilles, suspensions, emulsions or solutions, in particular, are suitable for oral or peroral administration. Suspensions, emulsions and especially solutions, in particular, are suitable for parenteral administration.

On account of their anti-inflammatory and in addition immunosuppressive action, the compounds of the general formula (I) according to the invention can be used for local and systemic administration as medicaments for the treatment or prophylaxis of the following disease states in mammals and humans:

(i) Pulmonary diseases which involve inflammatory, allergic and/or proliferative processes:
Chronic obstructive pulmonary diseases of any genesis, especially bronchial asthma
Bronchitis of varying genesis
Adult respiratory distress syndrome (ARDS), acute respiratory distress syndrome
Bronchiectasis
All forms of restrictive pulmonary diseases, especially allergic alveolitis,
Pulmonary oedema, in particular allergic
Sarcoidosis and granulomatosis, in particular Boeck disease (ii) Rheumatic diseases/autoimmune diseases/joint diseases, which involve inflammatory, allergic and/or proliferative processes:
All forms of rheumatic diseases, in particular rheumatoid arthritis, acute rheumatic fever, rheumatic polymyalgia, Behcet's disease
Reactive arthritis
Inflammatory soft-tissue diseases of other genesis
Arthritic symptoms in degenerative joint diseases (arthroses)
Vitiligo
Collagenoses of any origin, e.g. systemic lupus erythematosus, scleroderma, polymyositis, dermatomyositis-Sjögren's syndrome, Still's disease, Felty's syndrome
Sarcoidoses and granulomatoses
Soft tissue rheumatism (iii) Allergies or pseudoallergic diseases, which involve inflammatory, and/or proliferative processes:
All forms of allergic reactions, e.g. Quincke's oedema, hayfever, insect bite, allergic reactions to medicaments, blood derivatives, contrast agents etc., anaphylactic shock, urticaria, allergic and irritative contact dermatitis, allergic vascular diseases
Allergic vasculitis (iv) Vascular inflammation (vasculitis)
Panarteritis nodosa, temporal arteritis, nodal fever
Polyarteritis nodosa
Wegener's granulomatosis
Giant cell arteritis (v) Dermatological diseases which involve inflammatory, allergic and/or proliferative processes:
Atopic dermatitis (especially in children)
All forms of eczema such as, for example, atopic eczema (esp. in children)
Exanthema of any genesis or dermatoses
Psoriasis and parapsoriasis disorder
Pityriasis rubra pilaris
Erythematous diseases caused by different noxae, e.g. rays, chemicals, burns etc.
Bullous dermatoses such as, for example, autoimmune pemphigus vulgaris, bullous pemphigoid
Diseases of the lichenoid type,
Pruritus (e.g. of allergic genesis)
Rosacea disorder
Stevens-Johnson syndrome
Manifestation of vascular diseases
Hair loss such as alopecia areata
Cutaneous lymphoma
(vi) Renal diseases which involve inflammatory, allergic and/or proliferative processes:
Nephrotic syndrome
All nephrites, e.g. glomerulonephritis
(vii) Hepatic diseases which involve inflammatory, allergic and/or proliferative processes:
acute hepatitis of varying origin
chronic aggressive and/or chronic intermittent hepatitis
(viii) Gastrointestinal diseases which involve inflammatory, allergic and/or proliferative processes:
regional enteritis (Crohn's disease)
ulcerative colitis
gastroenteritis of varying origin, e.g. endemic sprue
(ix) Eye diseases which involve inflammatory, allergic and/or proliferative processes:
allergic keratitis, uveitis, iritis,
conjunctivitis
blepharitis
optical nerve neuritis
chorioiditis
sympathetic ophthalmia
(x) Diseases of the otorhinolaryngological region, which involve inflammatory, allergic and/or proliferative processes:
allergic rhinitis, hayfever
external otitis, e.g. caused by contact eczema
(xi) neurological diseases which involve inflammatory, allergic and/or proliferative processes:
cerebral oedema, especially allergic cerebral oedema
multiple sclerosis
acute encephalomyelitis
meningitis, especially allergic
Guillain-Barre syndrome
Alzheimer's disease
(xii) Blood diseases which involve inflammatory, allergic and/or proliferative processes, such as, for example:
Hodgkin's disease or non-Hodgkin's lymphoma, thrombocytaemias, erythrocytoses
Acquired haemolytic anaemia
Idiopathic thrombocytopenia
Idiopathic granulocytopenia
(xiii) Oncoses which involve inflammatory, allergic and/or proliferative processes
Acute lymphatic leukaemia
Malignant lymphoma
Lymphogranulomatoses
Lymphosarcomas
(xiv) Endocrine diseases which involve inflammatory, allergic and/or proliferative processes such as, for example:
Endocrine orbitopathy
De Quervain thyroiditis
Hashimoto's thyroiditis
Basedow's disease
Granulomatous thyroiditis
Lymphadenoid goitre
Autoimmune adrenalitis
Diabetes mellitus, in particular type 1 diabetes
Endometriosis
(xv) Organ and tissue transplants, graft-versus-host disease
(xvi) Severe states of shock, e.g. anaphylactic shock, systemic inflammatory response syndrome (SIRS)

One subject of the invention is the use of the compounds of the general formula (I) according to the invention for the production of a medicament.

A further subject of the invention is the use of the compounds according to the invention for the treatment of diseases which involve inflammatory, allergic and/or proliferative processes.

Preparation of the Compounds According to the Invention

Process Variant 1:

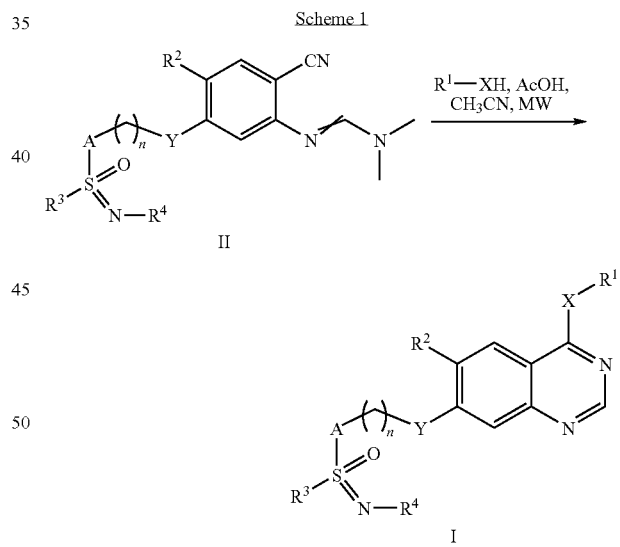

According to Y. Hang et al. (Org. Lett., 2004, 6, 4775-4778), the preparation of the compounds of the general formula (I) according to the invention is carried out by reaction of the intermediates as in formula (II) with compounds $R^1$—XH in the presence of acetic acid in acetonitrile as a solvent in a microwave, where $R^1$, $R^2$, $R^3$ and X, Y, A and n have the meanings indicated in the general formula (I) according to Claims 1 to 13. In this way, compounds with $R^4$ unequal to hydrogen are obtainable. By subsequent removal of $R^4$, compounds with $R^4$ equal to hydrogen can be obtained.

Preparation of the Intermediates of the Formula (II)

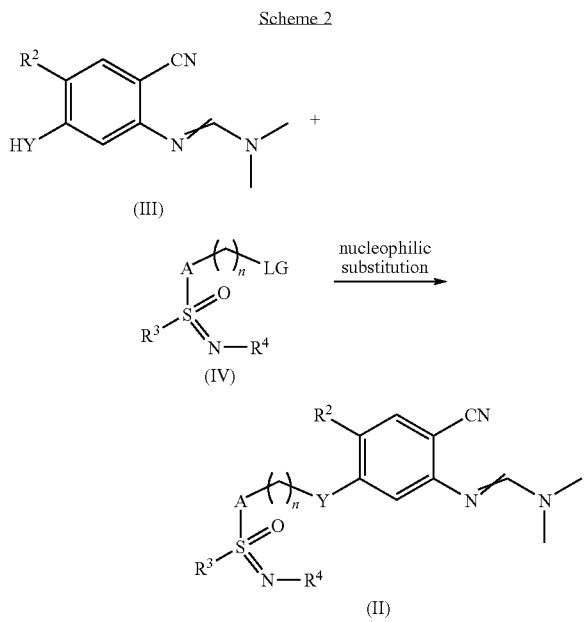

The substituents $R^2$, $R^3$ and Y, A and n have the meanings indicated in the general formula (I) according to Claims 1 to 13, where $R^4$ next to $R^4$ is unequal to hydrogen. Intermediates of the formula (II) are obtained by a nucleophilic substitution reaction of intermediates of the formula (III) with intermediates of the formula (IV). Intermediates of the formula (IV) are functionalized here using a group LG suitable for this purpose. Halogen and a mesylate, tosylate or triflate group, for example, are suitable as an LG. For the reaction of the intermediates (III) with (IV), inter alia, sodium carbonate, potassium carbonate or caesium carbonate are used as a base. Suitable solvents are, for example, acetone or dimethylformamide.

Preparation of the Intermediates of the Formula (III)

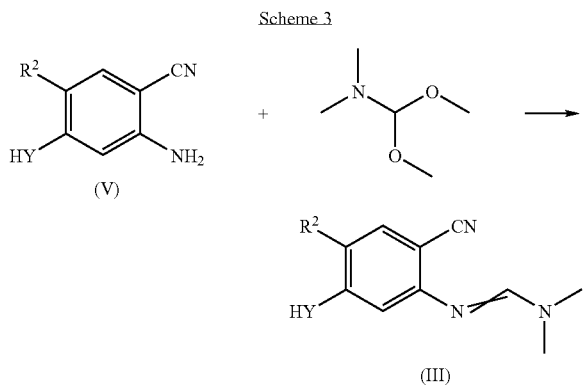

Intermediates of the formula (III) are obtained by reaction of intermediates of the formula (V) with N,N-dimethylformamide dimethyl acetal, where $R^2$ and Y have the meanings indicated in the general formula (I) according to Claims 1 to 13.

Preparation of the Intermediates of the Formula (IV)

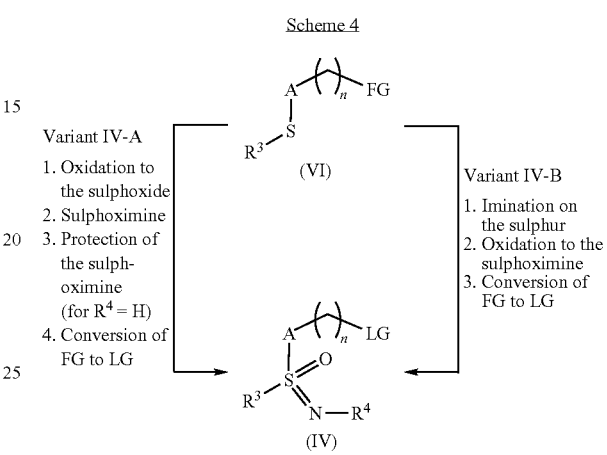

Variant IV-A
1. Oxidation to the sulphoxide
2. Sulphoximine
3. Protection of the sulphoximine (for $R^4$ = H)
4. Conversion of FG to LG Variant IV-B
1. Imination on the sulphur
2. Oxidation to the sulphoximine
3. Conversion of FG to LG Variant IV-A 1. Oxidation to the Sulphoxide.

A thioether of the formula (VI) is initially converted to the corresponding sulphoxide, where A and $R^3$ have the meanings indicated in the general formula (I) according to Claims 1 to 13. Suitable oxidizing agents for this transformation are, for example, sodium periodate, meta-chloroperbenzoic acid or hydrogen peroxide.

2. Sulphoximine Preparation

One of the most important methods of preparation of sulphoximines is the reaction of a sulphoxide with hydrazoic acid, which is generated in situ, for example from the reaction of sodium azide and conc. sulphuric acid (M. Reggelin, C. Zur, Synthesis 2000, 1, 1). The reaction can be carried out in an organic solvent, such as chloroform.

Further methods for the synthesis of sulphoximines are, for example, the reaction of sulphoxides with a) $TsN_3$ ((a) R. Tanaka, K. Yamabe, J. Chem. Soc. Chem. Commun. 1983, 329; (b) H. Kwart, A. A. Kahn, J. Am. Chem. Soc. 1967, 89, 1959)).

b) N-tosylimino phenyl iodinane and catalytic amounts of Cu(I) triflate (J. F. K. Müller, P. Vogt, Tetrahedron Lett. 1998, 39, 4805)

c) Boc azide and catalytic amounts of iron(ll) chloride (T. Bach, C. Korber, Tetrahedron Lett. 1998, 39, 5015) or d) o-Mesitylenesulphonylhydroxylamine (MSH) (C. R. Johnson, R. A. Kirchhoff, H. G. Corkins, J. Org. Chem. 1974, 39, 2458).

e) [N-(2-(Trimethylsilyl)ethanesulphonyl)imino]phenyliodinane (PhI=NSes) (S. Cren, T. C. Kinahan, C. L. Skinner and H. Tye, Tetrahedron Lett. 2002, 43, 2749).

f) Trifluoroacetamide or sulphonylamides in combination with iodobenzene diacetate, magnesium oxide and catalytic amounts of rhodium(II) acetate dimer (H. Okamura, C. Bolm, Org. Lett. 2004, 6, 1305.
g) Sulphonylamides in combination with iodobenzene diacetate and catalytic amounts of a chelating ligand and silver salts (G. Y. Cho, C. Bolm, Org. Lett. 2005, 7, 4983).
h) NsNH$_2$ and iodobenzene diacetate (G. Y. Cho, C. Bolm, Tetrahedron Lett. 2005, 46, 8007).
i) NsNH$_2$ and iodosylbenzene in the presence of catalytic amounts of Fe(acac)$_3$ (O. G. Mancheno, C. Bolm, Org. Lett. 2006, 8, 2349-2352).

3. Protection of the Sulphoximine

If the preparation of the sulphoximine is carried out, for example, by means of sodium azide and sulphuric acid or by means of o-mesitylenesulphonylhydroxylamine (MSH), further derivatizations can subsequently be performed on the nitrogen of the sulphoximine group. For example, the sulphoximine nitrogen can be alkylated, acylated, arylated or the reaction can be carried out using ethyl chloroformate (for derivatization on the sulphoximine nitrogen, for this see M. Reggelin, C. Zur, Synthesis 2000, 1,1-64. C. Bolm, J. Sedelmeier, J. Org. Chem. 2005, 70, 6904-6906).

4. Conversion of FG to LG

Functional groups FG are, for example, carboxylic acid and ester. These groups can be reduced to the corresponding alcohol. In a subsequent step, the alcohol is converted to a mesylate, tosylate and triflate group belonging to the LG group.

If A=aryl/hetaryl and n=1, FG can be, for example, a hydroxyl group or hydrogen optionally present in protected form. By means of free radical halogenation, this hydrogen can be replaced by a halogen substituent.

Variant IV-B

1. Imination on the Sulphur

Starting from the thioether (VI), the preparation of the corresponding sulphimides is carried out, inter alia, by means of Fe(acac)$_3$ (O. G. Mancheno, C. Bolm, Org. Lett. 2006, 8, 2349-2352) or [Rh$_2$(OAc)$_4$] (H. Okamura, C. Bolm, Org. Lett. 2004, 6,1305-1307)-catalysed imination on the sulphur centre. If the imination is chosen as the first reaction step, then this applies initially for the imination R$^4$ unequal to hydrogen 2. Oxidation to the Sulphoximine Sulphimides can be oxidized to the sulphoximine (for this see N. Pesa, C. J. Welch, A. N. Boa J. Heterocycl. Chem. 2005, 599-607).

3. Conversion of FG to LG

Functional groups FG are, for example, carboxylic acid and ester. These groups can be reduced to the corresponding alcohol. In a subsequent step, the alcohol is converted to a mesylate, tosylate and triflate group belonging to the LG group.

If A=aryl/hetaryl and n=1, FG can be, for example, a hydroxyl group or hydrogen optionally present in protected form. By means of a free radical halogenation, this hydrogen can be replaced by a halogen substituent.

The preparation of enantiomerically pure sulphoximines is described, for example, by means of resolution using enantiomerically pure camphor-10-sulphonic acid ((a) C. R. Johnson, C. W. Schroeck, J. Am. Chem. Soc. 1973, 95, 7418; (b) C. S. Shiner, A. H. Berks, J. Org. Chem. 1988, 53, 5543). A further method for the preparation of optically active sulphoximines consists in the stereoselective imination of optically active sulphoxides ((a) C. Bolm, P. Müller, K. Harms, Acta Chem. Scand. 1996, 50, 305; (b) Y. Tamura, J. Minamikawa, K. Sumoto, S. Fujii, M. Ikeda, J. Org. Chem. 1973, 38,1239; (c) (H. Okamura, C. Bolm, Org.Lett. 2004, 6, 1305).

Process Variant 2:

Scheme 5

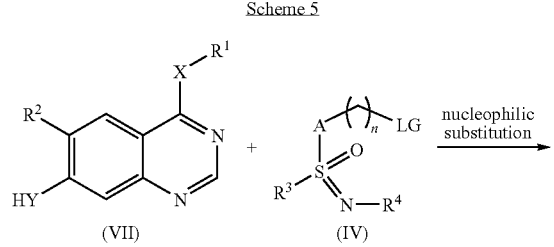

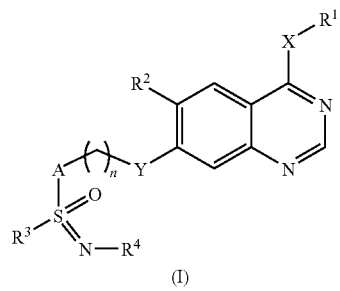

The preparation of the compounds of the general formula (I) according to the invention is carried out in this variant by the reaction of the quinazolines of the formula (VII) with intermediates of the formula (IV), where R$^1$, R$^2$, R$^3$ and X, Y, A and n have the meanings indicated in the general formula (I) according to Claims 1 to 13. In this way, initially compounds with R$^4$ unequal to hydrogen are obtainable. In a subsequent step, R$^4$ can be removed with the obtainment of compounds with R$^4$ equal to hydrogen. The reaction is carried out analogously to the reaction of the intermediates of the formula (III) with intermediates of the formula (IV) (see Scheme 2).

Preparation of the Intermediates of the Formula (VII)

The synthesis of the quinazolines of the (VII) is carried out in a manner analogous to that described in Process variant 1 (see Scheme 1) or according to other methods known to the person skilled in the art (for this see Science of Synthesis, Houben-Weyl Methods of Molecular Transformations, Thieme Verlag, 2004, Volume 16, pages 573-749).

Process Variant 3:

Scheme 6

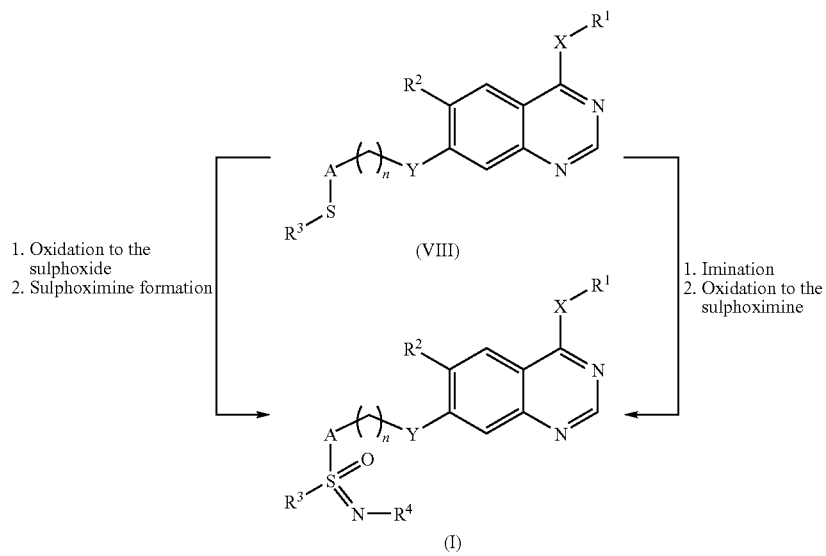

1. Oxidation to the sulphoxide
2. Sulphoximine formation

1. Imination
2. Oxidation to the sulphoximine

In this process variant, the compounds of the general formula (I) according to the invention can be prepared in two ways. Starting from compounds of the formula (VIII), the sulphur centre is converted to the sulphoxide, followed by the formation of the corresponding sulphoximine, where $R^1$, $R^2$, $R^3$, $R^4$ and X, Y, A and n have the meanings indicated in the general formula (I) according to Claims 1 to 13. Alternatively, compounds of the formula (VIII) can initially be converted by an imination reaction on the sulphur centre to a sulphimide, which is subsequently oxidized to the sulphoximine.

If the imination is chosen as the first reaction step, then this applies initially for the imination $R^4$ unequal to hydrogen. After the oxidation of the sulphimide to the corresponding sulphoximine, $R^4$ can be removed with the obtainment of compounds with $R^4$ equal to hydrogen.

Preparation of the Intermediates of the Formula (VII)

Variant VIII-A

Intermediates of the formula (VIII) can be prepared analogously to Process variant 1 (see Scheme 1). Intermediates of the formula (IX) are obtained analogously to Scheme 3 by reaction of the intermediates of the formula (III) with intermediates of the formula (X). $R^1$, $R^2$, $R^3$ and X, Y, A and n have the meanings indicated in the general formula (I) according to Claims 1 to 13.

Scheme 8

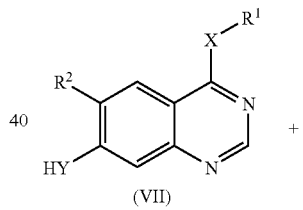

Scheme 7

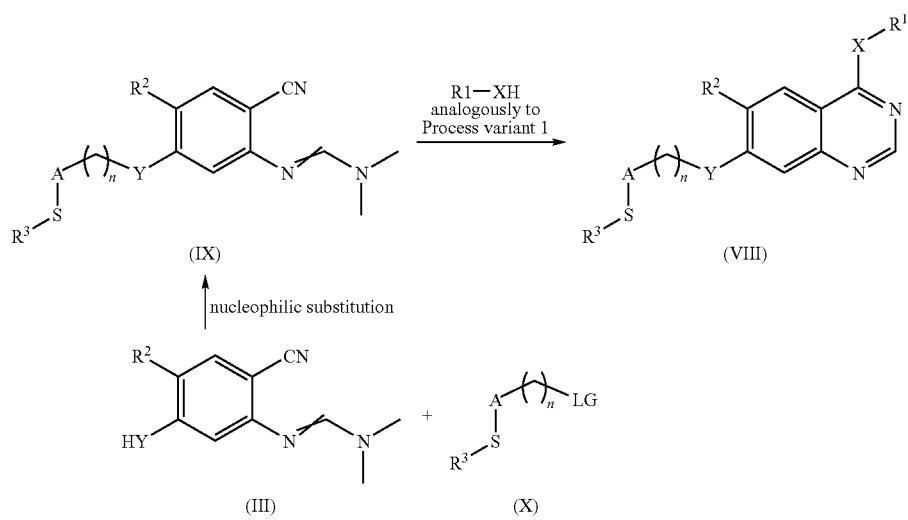

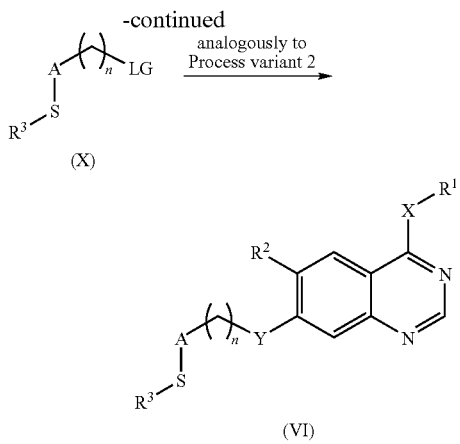

Variant VIII-B

Alternatively and analogously to Process variant 2 (see Scheme 5), intermediates of the formula (VIII) can be prepared by reaction of the intermediates of the formula (VII) with intermediates of the formula (X).

Halogen and a mesylate, tosylate or triflate group and in this case also a hydroxyl group are suitable, for example, as LG.

If LG is a hydroxyl group, the linkage of the intermediates of the formula (V) with intermediates of the formula (X) can be carried out, for example, by means of a Mitsunobu reaction (O. Mitsunobu Synthesis 1981, 1-27).

EXPERIMENTAL SECTION

I. Synthesis

General Working Procedures (GWP)

General Working Procedure 1 (GWP 1): Preparation of Sulphoxides

Thioether (1.0 eq) is introduced into methanol (15 ml/1 mmol of thioether) and tetra-hydrofuran (12 ml/1 mmol). After addition of a solution of sodium periodate (1.3 eq) in water (7 ml/1 mmol of periodate), the reaction mixture is stirred at room temperature and added to dilute aqueous sodium chloride solution. It is extracted with ethyl acetate. After drying the combined organic phases over sodium sulphate and removing the solvents, the residue is purified by means of chromatography.

General Working Procedure 2 (GWP 2): Preparation of Sulphoximines

Sulphoxide (1.0 eq) is suspended in chloroform (1 ml/1 mmol) and treated with sodium azide (2.3 eq). Sulphuric acid (9.5 eq) is added dropwise at 0° C. and the reaction batch is subsequently stirred at 45° C. for 72 h and rendered basic by means of 4N sodium hydroxide solution with ice bath cooling. After removal of the solvents, the residue is purified by means of chromatography.

General Working Procedure 3 (GWP 3): Reaction of the Sulphoximines with Ethyl Chloroformate A solution of sulphoximine (1.0 eq) in pyridine (10 ml/1 mmol) is treated dropwise at room temperature with ethyl chloroformate (5.0 eq) and subsequently stirred at room temperature. The batch is added to dilute NaCl solution and extracted with ethyl acetate. After drying the combined organic phases over sodium sulphate and subsequently removing the solvents, the residue is purified by means of chromatography.

General Working Procedure 4 (GWP 4): Free Radical Bromination

The compound prepared by means of GWP3 (1.0 eq) is introduced into carbon tetrachloride (1 ml/1 mmol), treated with N-bromosuccinimide (1.0 eq) and azobisisobutyronitrile (0.1 eq) and subsequently refluxed for 5 hours. After cooling to RT, precipitated crystals are filtered off with suction and washed with $CCl_4$. The filtrate is concentrated to dryness and the residue is purified by chromatography.

General Working Procedure 5 (GWP 5): Preparation of Compounds of the General Formula (I) According to Process Variant 1 (see Scheme 1)

According to Y. Hang et al. (Org. Lett., 2004, 6, 4775-4778), the intermediate of the formula (II) (1.0 eq) is introduced into acetonitrile (1 mL/0.1 mmol)) and acetic acid (6.0 eq), treated with amine (1.2 eq) and irradiated with microwaves at 160° C. with stirring for 10 minutes. The reaction mixture is subsequently concentrated. The residue is treated with saturated $NaHCO_3$ solution. The aqueous phase is extracted with ethyl acetate. After drying the combined organic phases over sodium sulphate and removing the solvents, the residue is purified by means of chromatography.

General Working Procedure 6 (GWP 6): Removal of the Ethoxycarbonyl Group on the Sulphoximine The compound prepared according to GWP 5 (1.0 eq) is dissolved in ethanol (10 ml/1 mmol). After addition of sodium ethoxide (3.6 eq), the reaction mixture is stirred at 60° C. for 6 hours and is subsequently added to dilute aqueous sodium carbonate solution. The aqueous phase is extracted with ethyl acetate and the combined organic phases are dried over sodium sulphate. After removing the solvents, the residue is purified by means of chromatography.

1. Process Variant 1

Example 1.1

(RS)-S-[3-({[6-Bromo-4-(isopropylamino)quinazolin-7-yl]oxy}methyl)phenyl]-N-(ethoxycarbonyl)-S-methylsulphoximide

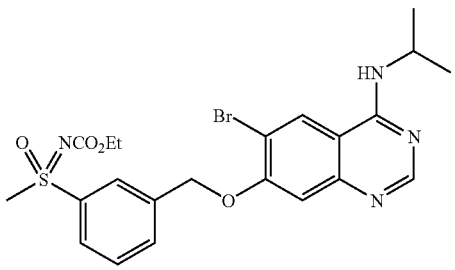

1.1. a) Preparation of the Intermediates

Compound 1.1. a.1

(RS)-3-(Methylsulphinyl)toluene

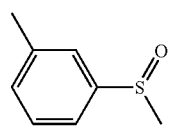

According to GWP 1, in the case of reaction of 3-methylthioanisole (5.0 g, 36.2 mmol) the desired product is obtained after chromatographic purification (silica gel, hexane/ethyl acetate: 0→100% ethyl acetate) in 83% yield (4.6 g).

¹H-NMR (400 MHz, DMSO-d6): δ 2.35 (s, 3H), 2.68 (s, 3H), 7.30-7.32 (m, 1H), 7.42-7.46 (m, 3H).

Compound 1.1. a.2

(RS)-S-Methyl-S-(m-tolyl)sulphoximide

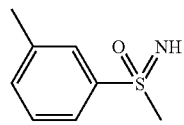

According to GWP 2, in the case of the reaction of (RS)-3-(methylsulphinyl)toluene (4.6 g, 29.8 mmol) the desired product is obtained after chromatographic purification (silica gel, hexane/ethyl acetate: 0→100% ethyl acetate, then ethyl acetate/methanol: 4/1) in 74% yield (3.74 g).

¹H-NMR (400 MHz, DMSO-d6): δ 2.37 (s, 3H), 3.00 (s, 3H), 4.11 (s, 1H), 7.41-7.45 (m, 2H), 7.67-7.72 (m, 2H).

Compound 1.1. a.3

(RS)-N-(Ethoxycarbonyl)-S-methyl-S-(m-tolyl)sulphoximide

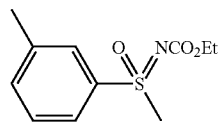

According to GWP 3, in the case of the reaction of (RS)-S-methyl-S-(m-tolyl)sulphoximide (3.74 g, 22.1 mmol) the desired product is obtained after chromatographic purification (silica gel, hexane/ethyl acetate: 0→100% ethyl acetate, then ethyl acetate/methanol: 4/1) in 99% yield (5.3 g).

¹H-NMR (300 MHz, DMSO-d6): δ 1.05 (t, 3H), 2.39 (s, 3H), 3.40 (s, 3H), 3.82-3.91 (m, 2H), 7.52-7.54 (m, 2H), 7.71-7.74 (m, 2H).

Compound 1.1. a.4

(RS)-S-[3-(Bromomethyl)phenyl]-N-(ethoxycarbonyl)-S-methylsulphoximide

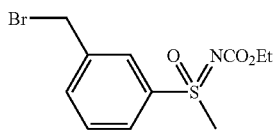

According to GWP 4, in the case of the reaction of (RS)-N-(ethoxycarbonyl)-S-methyl-S-(m-tolyl)sulphoximide (2.71 g, 11.2 mmol) the desired product is obtained after chromatographic purification (silica gel, hexane/ethyl acetate: 0→100% ethyl acetate, then ethyl acetate/methanol: 4/1) in 31% yield (1.1 g).

¹H-NMR (400 MHz, DMSO-d6): δ 1.04 (t, 3H), 3.44(s, 3H), 3.84-3.91 (m, 2H), 4.80 (s, 2H), 7.64 (t, 1H), 7.79 (d, 1H), 7.86 (d, 1H), 8.02 (s, 1H).

Compound 1.1. a.5

2-Amino-5-bromo-4-methoxybenzonitrile

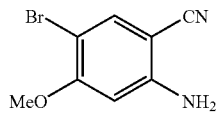

2-Amino-4-methoxybenzonitrile (4.47 g, 30.2 mmol) is dissolved in 70 ml of dioxane and treated at 0° C. with bromine (1.71 ml, 33.2 mmol). It is subsequently stirred at 0° C. for one hour. After addition of diethyl ether, the resulting crystals are filtered off with suction. The desired product is obtained in 81% yield (5.52 g).

¹H-NMR (400 MHz, DMSO-d6): δ 3.75 (s, 3H), 6.30-6.50 (m, 3H), 7.54 (s, 1H).

Compound 1.1. a.6

(E/Z)-N'-(4-Bromo-2-cyano-5-methoxyphenyl)-N,N-dimethylformimidamide

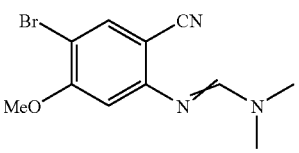

2-Amino-5-bromo-4-methoxybenzonitrile (3.0 g, 13.2 mmol) is treated with N,N-di-methylformamide dimethyl acetal (6.5 ml, 48.9 mmol) and subsequently stirred at room temperature for 24 hours. The reaction mixture is concentrated to dryness a number of times with toluene. The desired product is obtained after chromatographic purification (silica gel, hexane/ethyl acetate: 0→100% ethyl acetate, then ethyl acetate/methanol: 4/1) in 42% yield (1.56 g).

¹H-NMR (300 MHz, DMSO-d6): δ 2.95 (s, 3H), 3.05 (s, 3H), 3.87 (s, 3H), 6.80 (s, 1H), 7.75 (s, 1H), 7.99 (s, 1H).

Compound 1.1. a.7

(E/Z)-N'-(4-Bromo-2-cyano-5-hydroxyphenyl)-N,N-dimethylformimidamide

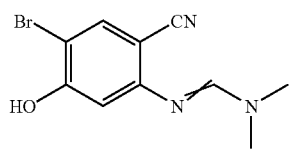

(E/Z)-N'-(4-Bromo-2-cyano-5-methoxyphenyl)-N,N-dimethylformimidamide (1.28 g, 4.54 mmol) is dissolved in 45 ml of methylene chloride. Boron tribromide solution (1 M) in methylene chloride (91 ml, 91 mmol) is added dropwise. After 20 hours at room temperature, the reaction is terminated by addition of methanol. The reaction mixture is concentrated to dryness a number of times with toluene. The desired product is obtained after chromatographic purification (silica gel, hexane/ethyl acetate: 0→100% ethyl acetate, then ethyl acetate/methanol: 4/1) in 21% yield (250 mg).

¹H-NMR (300 MHz, DMSO-d6): δ 2.92 (s, 3H), 3.02 (s, 3H), 6.50 (s, 1H), 7.69 (s, 1H), 7.75 (s, 1H), 11.01 (br, 1H).

Compound 1.1. a.8

(E/Z)-N'-(4-Bromo-2-cyano-5-{3-[(RS)-N-(ethoxycarbonyl)-S-methylsulphonimidoyl]-benzyloxy}phenyl)-N,N-dimethylformimidamide

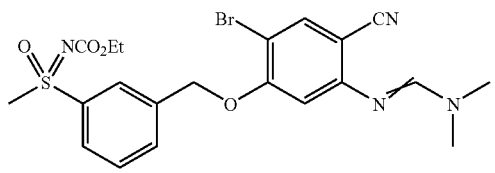

(E/Z)-N'-(4-Bromo-2-cyano-5-hydroxyphenyl)-N,N-dimethylformimidamide (720 mg, 2.69 mmol) and (RS)-S-[3-(bromomethyl)phenyl]-N-(ethoxycarbonyl)-S-methyl-sulphoximide (945 mg, 2.95 mmol) are suspended in 12 ml of acetone. After addition of potassium carbonate (687 mg, 4.97 mmol), the reaction mixture is refluxed for 6 hours. The batch is diluted with ethyl acetate, and the organic phase is washed with water and dried over sodium sulphate. The desired product is obtained after removing the solvent and after chromatographic purification (silica gel, hexane/ethyl acetate: 0→100% ethyl acetate, then ethyl acetate/methanol: 4/1) in 46% yield (620 mg).

¹H-NMR (300 MHz, DMSO-d6): δ 1.02 (t, 3H), 2.96 (s, 3H), 3.06 (s, 3H), 3.44 (s, 3H), 3.79-3.91 (m, 2H), 5.37 (s, 2H), 6.96 (s, 1H), 7.71 (t, 1H), 7.79-7.81 (m, 2H), 7.91 (d, 1H), 7.96 (s, 1H), 8.08 (s, 1H).

1.1. b) Preparation of the Final Product

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (50 mg, 0.1 mmol) with isopropylamine (0.01 ml, 0.12 mmol) the desired product is obtained after chromatographic purification (silica gel, dichloromethane/methanol: 0→20% methanol) in 78% yield (40 mg).

¹H-NMR (300 MHz, DMSO-d6): δ 1.07 (t, 3H), 1.25 (d, 6H), 3.48 (s, 3H), 3.84-3.95 (m, 2H), 4.43-4.51 (m, 1H), 5.50 (s, 2H), 7.33 (s, 1H), 7.77 (t, 1H), 7.89-7.97 (m, 3H), 8.15 (s, 1H), 8.43 (s, 1H), 8.72 (s, 1H).

Example 1.2

(RS)-S-[3-({[6-Bromo-4-(isopropylamino)quinazolin-7-yl]oxy}methyl)phenyl]-S-methylsulphoximide

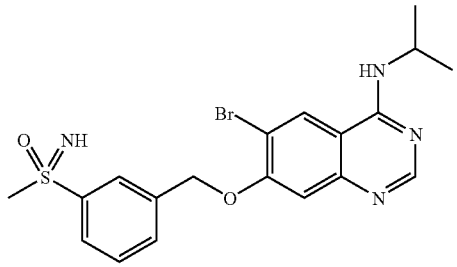

According to GWP 6, in the case of the reaction of (RS)-S-[3-({[6-bromo-4-(isopropylamino)quinazolin-7-yl]oxy}methyl)phenyl]-N-(ethoxycarbonyl)-S-methylsulphoximide (100 mg, 0.19 mmol), the desired product is obtained after chromatographic purification (silica gel, dichloromethane/methanol: 0→20% methanol) in 61% yield (52 mg).

¹H-NMR (300 MHz, DMSO-d6): δ 1.25 (d, 6H), 3.09 (s, 3H), 4.28 (s, 1H), 4.43-4.51 (m, 1H), 5.47 (s, 2H), 7.32 (s, 1H), 7.68 (t, 1H), 7.80 (d, 1H), 7.92-7.95 (m, 2H), 8.13 (s, 1H), 8.42 (s, 1H), 8.71 (s, 1H).

Example 1.3

(RS)-S-{3-[({6-Bromo-4-[(cyclopropylmethyl)amino]quinazolin-7-yl}oxy)methyl]-phenyl}-N-(ethoxycarbonyl)-S-methylsulphoximide

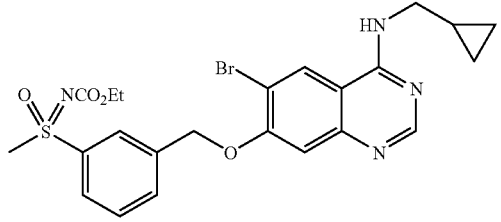

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (50 mg, 0.1 mmol) with cyclopropylmethylamine (8.4 mg, 0.12 mmol), the desired product is obtained after chromatographic purification in 76% yield (40 mg).

¹H-NMR (300 MHz, DMSO-d6): δ 0.26-0.31 (m, 2H), 0.47-0.51 (m, 2H), 1.05-1.17 (m, 4H), 3.37-3.41 (m, 2H), 3.48 (s, 3H), 3.48-3.95 (m, 2H), 5.50 (s, 2H), 7.35 (s, 1H), 7.77 (t, 1H), 7.89-7.97 (m, 2H), 8.15 (s, 1H), 8.37 (t, 1H), 8.42 (s, 1H), 8.69 (s, 1H).

Example 1.4

(RS)-S-{3-[({6-Bromo-4-[(cyclopropylmethyl)amino]quinazolin-7-yl}oxy)methyl]-phenyl}-S-methylsulphoximide

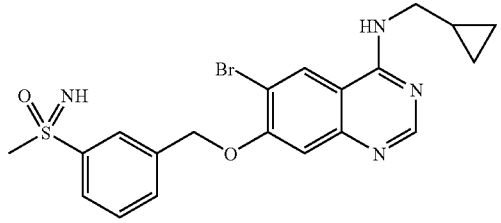

According to GWP 6, in the case of the reaction of (RS)-S-{3-[({6-bromo-4-[(cyclo-propylmethyl)amino]quinazolin-7-yl}oxy)methyl]phenyl]-N-(ethoxycarbonyl)-S-methyl-sulphoximide (40 mg, 0.075 mmol), the desired product is obtained after chromatographic purification (silica gel, dichloromethane/methanol: 0→30% methanol) in 90% yield (31 mg).

¹H-NMR (300 MHz, DMSO-d6): δ 0.26-0.31 (m, 2H), 0.45-0.51 (m, 2H), 1.15-1.19 1H), 3.09 (s, 3H), 3.36-3.41 (m, 2H), 4.27 (s, 1H), 5.48 (s, 2H), 7.34 (s, 1H), 7.68 (t, 1H), 7.80 (d, 1H), 7.93 (d, 1H), 8.13 (s, 1H), 8.36 (t, 1H), 8.42 (s, 1H), 8.69 (s, 1H).

Example 1.5

(RS)-S-{3-[({6-Bromo-4-[(4-hydroxyphenyl)amino]quinazolin-7-yl}oxy)methyl]-phenyl}-N-(ethoxycarbonyl)-S-methylsulphoximide

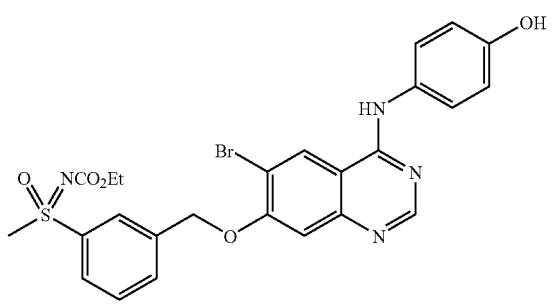

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethyl-formimidamide (53 mg, 0.1 mmol) with 4-aminophenol (13.7 mg, 0.13 mmol), the desired product is obtained after chromatographic purification (silica gel, hexane/ethyl acetate: 0→100% ethyl acetate, then dichloromethane/methanol 0→20% methanol) in quantitative yield (60 mg).

¹H-NMR (300 MHz, DMSO-d6): δ 1.07 (t, 3H), 3.49 (s, 3H), 3.85-3.96 (m, 2H), 5.53 (s, 2H), 6.79 (d, 2H), 7.41 (s, 1H), 7.52 (d, 2H), 7.78 (t, 1H), 7.90-7.98 (m, 2H), 8.17 (s, 1H), 8.47 (s, 1H), 8.90 (s, 1H), 9.33 (s, 1H).

Example 1.6

(RS)-S-[3-({[6-Bromo-4-(1H-pyrazol-3-ylamino)quinazolin-7-yl]oxy}methyl)-phenyl]-N-(ethoxycarbonyl)-S-methylsulphoximide

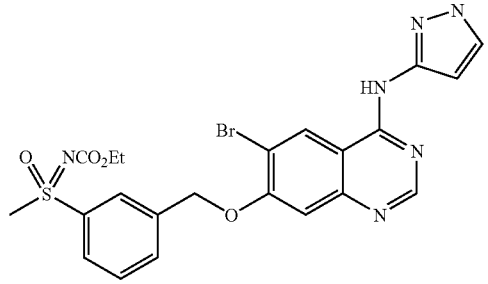

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethyl-formimidamide (50 mg, 0.1 mmol) with 3-aminopyrazole (9.8 mg, 0.12 mmol), the desired product is obtained after chromatographic purification (silica gel, dichloromethane/methanol: 0→30% methanol) in 77% yield (42 mg).

¹H-NMR (400 MHz, DMSO-d6): δ 1.03 (t, 3H), 3.44 (s, 3H), 3.83-3.92 (m, 2H), 5.49 (s, 2H), 6.79 (s, 1H), 7.38 (s, 1H), 7.65 (s, 1H), 7.73 (t, 1H), 7.87 (d, 1H), 7.92 (d, 1H), 8.12 (s, 1H), 8.52 (s, 1H), 9.04 (s, 1H), 10.41 (s, 1H), 12.46 (s, 1H).

Example 1.7

(RS)-S-[3-({[6-Bromo-4-(1H-pyrazol-3-ylamino)quinazolin-7-yl]oxy}methyl)-phenyl]-S-methylsulphoximide

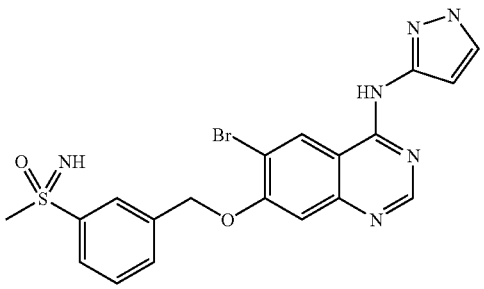

According to GWP 6, in the case of the reaction of (RS)-S-[3-({[6-bromo-4-(1 H-pyrazol-3-ylamino)quinazolin-7-yl]oxy}methyl)phenyl]-N-(ethoxycarbonyl)-S-methyl-sulphoximide (40 mg, 0.073 mmol), the desired product is obtained after chromatographic purification (silica gel, dichloromethane/methanol: 0→30% methanol) in 35% yield (12 mg).

¹H-NMR (400 MHz, DMSO-d6): δ 3.05 (s, 3H), 4.25 (s, 1H), 5.46 (s, 2H), 6.79 (s, 1H), 7.37 (s, 1H), 7.63-7.67 (m, 2H), 7.78 (d, 1H), 7.89 (d, 1H), 8.09 (s, 1H), 8.52 (s, 1H), 9.04 (s, 1H), 10.4 (s, 1H), 12.46 (s, 1H).

Example 1.8

(RS)-S-{3-[({6-Bromo-4-[(2-methoxyethyl)amino]quinazolin-7-yl}oxy)methyl]-phenyl}-N-(ethoxycarbonyl)-S-methylsulphoximide

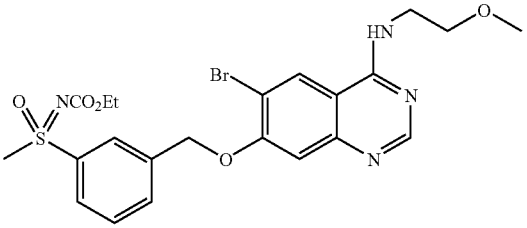

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethyl-formimidamide (50 mg, 0.1 mmol) with 2-methoxyethylamine (8.9 mg, 0.12 mmol) the desired product is obtained after chromatographic purification (silica gel, dichloro-methane/methanol: 0→30% methanol) in 95% yield (50 mg).

¹H-NMR (400 MHz, DMSO-d6): δ 1.02 (t, 3H), 3.24 (s, 3H), 3.44 (s, 3H), 3.52 (t, 2H), 3.64 (q, 2H), 3.82-3.90 (m, 2H), 5.46 (s, 2H), 7.31 (s, 1H), 7.72 (t, 1H), 7.86 (d, 1H), 7.91 (d, 1H), 8.11 (s, 1H), 8.28 (t, 1H), 8.40 (s, 1H), 8.63 (s, 1H).

Example 1.9

(RS)-S-{3-[({6-Bromo-4-[(2-methoxyethyl)amino]quinazolin-7-yl}oxy)methyl]-phenyl}-S-methylsulphoximide

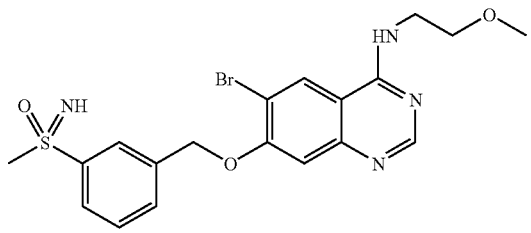

According to GWP 6, in the case of the reaction of (RS)-S-{3-[({6-bromo-4-[(2-methoxyethyl)amino]quinazolin-7-yl}oxy)methyl]phenyl}-N-(ethoxycarbonyl)-S-methyl-sulphoximide (45 mg, 0.084 mmol) the desired product is obtained after chromatographic purification (silica gel, dichloromethane/methanol: 0→25% methanol) in 92% yield (36 mg).

$^1$H-NMR (300 MHz, DMSO-d6): δ 3.09 (s, 3H), 3.29 (s, 3H), 3.56 (t, 2H), 3.68 (q, 2H), 4.28 (s, 1H), 5.48 (s, 2H), 7.34 (s, 1H), 7.68 (t, 1H), 7.80 (d, 1H), 7.93 (d, 1H), 8.13 (s, 1H), 8.33 (t, 1H), 8.44 (s, 1H), 8.67 (s, 1H).

Example 1.10

(RS)-S-(3-{[(6-Bromo-4-{[2-(dimethylamino)ethyl]amino}quinazolin-7-yl)oxy]-methyl}phenyl)-N-(ethoxycarbonyl)-S-methylsulphoximide

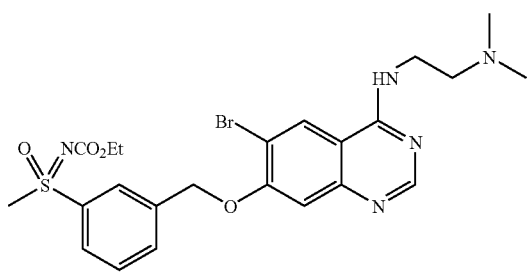

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (50 mg, 0.1 mmol) with N,N-dimethylethylenediamine (0.013 ml, 0.12 mmol) the desired product is obtained after chromatographic purification (silica gel, dichloromethane/methanol: 0→30% methanol) in 94% yield (51 mg).

$^1$H-NMR (400 MHz, DMSO-d6): δ 1.02 (t, 3H), 2.16 (s, 6H), 3.26-3.28 (m, water+2H), 3.44 (s, 3H), 3.57 (q, 2H), 3.81-3.90 (m, 2H), 5.45 (s, 2H), 7.30 (s, 7.72 (t, 1H), 7.86 (d, 1H), 7.91 (d, 1H), 8.11 (s, 1H), 8.15 (t, 1H), 8.39 (s, 1H), 8.60 (s, 1H).

Example 1.11

(RS)-S-(3-{[(6-Bromo-4-{[2-(dimethylamino)ethyl]amino}quinazolin-7-yl)oxy]-methyl}phenyl)-S-methylsulphoximide

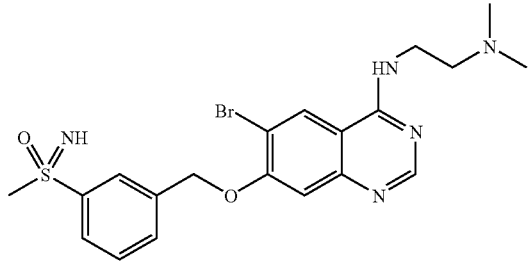

According to GWP 6, in the case of the reaction of (RS)-S-(3-{[(6-bromo-4-{[2-(dimethylamino)ethyl]amino}quinazolin-7-yl)oxy]methyl}phenyl)-N-(ethoxycarbonyl)-S-methylsulphoximide (45 mg, 0.082 mmol) the desired product is obtained after chromatographic purification (silica gel, dichloromethane/methanol: 0→25% methanol) in 85% yield (33 mg).

$^1$H-NMR (300 MHz, DMSO-d6): δ 2.23 (s, 6H), 3.09 (s, 3H), 3.31-3.33 (water, 2H), 3.62 (q, 2H), 4.28 (s, 1H), 5.48 (s, 2H), 7.34 (s, 1H), 7.68 (t, 1H), 7.80 (d, 1H), 7.93 (d, 1H), 8.12 (s, 1H), 8.21 (t, 1H), 8.43 (s, 1H), 8.64 (s, 1H).

Example 1.12

(RS)-S-[3-{[6-Bromo-4-(cyclopropylamino)quinazolin-7-yl]oxy}methyl)phenyl]-N-(ethoxycarbonyl)-S-methylsulphoximide

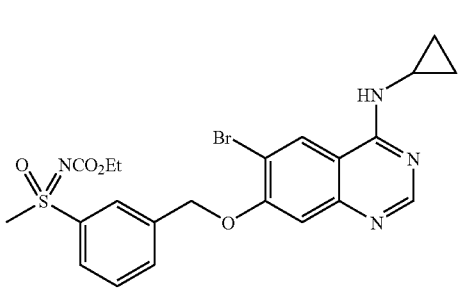

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (50 mg, 0.1 mmol) with cyclopropylamine (6.7 mg, 0.12 mmol), the desired product is obtained after chromatographic purification (silica gel, dichloro-methane/methanol: 0→30% methanol) in 98% yield (50 mg).

$^1$H-NMR (400 MHz, DMSO-d6): δ 0.58-0.61 (m, 2H), 0.73-0.78 (m, 2H), 1.02 (t, 3H), 2.96-3.00 (m, 1H), 3.44 (s, 3H), 3.80-3.90 (m, 2H), 5.45 (s, 2H), 7.31 (s, 1H), 7.72 (t, 1H), 7.85 (d, 1H), 7.91 (d, 1H), 8.11 (s, 1H), 8.17 (d, 1H), 8.45 (s, 1H), 8.58 (s, 1H).

Example 1.13

(RS)-S-[3-({[6-Bromo-4-(cyclopropylamino)quinazolin-7-yl]oxy}methyl)phenyl]-S-methylsulphoximide

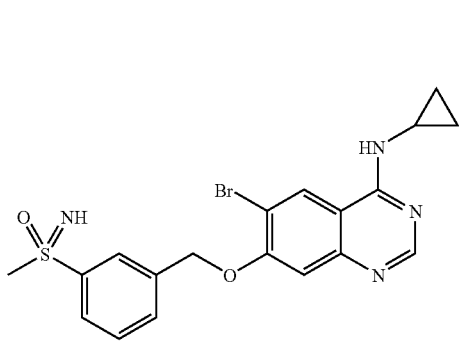

According to GWP 6, in the case of the reaction of (RS)-S-[3-({[6-bromo-4-(cyclo-propylamino)quinazolin-7-yl]oxy}methyl)phenyl]-N-(ethoxycarbonyl)-S-methylsulphoximide (45 mg, 0.087 mmol), the desired product is obtained after chromatographic purification (silica gel, dichloromethane/methanol: 0→30% methanol) in 83% yield (32 mg).

¹H-NMR (300 MHz, DMSO-d6): δ 0.61-0.66 (m, 2H), 0.77-0.83 (m, 2H), 2.99-3.06 (m, 1H), 3.09 (s, 3H), 4.28 (s, 1H), 5.47 (s, 2H), 7.35 (s, 1H), 7.68 (t, 1H), 7.80 (d, 1H), 7.93 (d, 1H), 8.12 (s, 1H), (8.22 (d, 1H), 8.49 (s, 1H), 8.62 (s, 1H).

Example 1.14

(RS)-S-[3-({[6-Bromo-4-(cyclobutylamino)quinazolin-7-yl]oxy}methyl)phenyl]-N-(ethoxycarbonyl)-S-methylsulphoximide

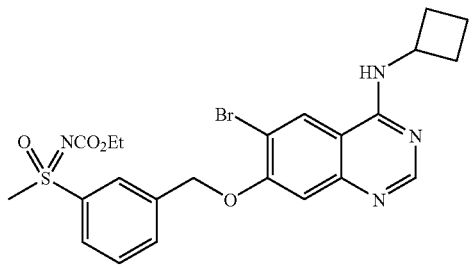

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (50 mg, 0.1 mmol) with cyclobutylamine (8.4 mg, 0.12 mmol) the desired product is obtained after chromatographic purification (silica gel, dichloromethane/methanol: 0→30% methanol) in 94% yield (49 mg).

¹H-NMR (400 MHz, DMSO-d6): δ 1.02 (t, 3H), 1.64-1.73 (m, 2H), 2.02-2.12 (m, 2H), 2.25-2.32 (m, 2H), 3.44 (s, 3H), 3.81-3.90 (m, 2H), 4.61-4.67 (m, 1H), 5.45 (s, 2H), 7.29 (s, 1H), 7.72 (t, 1H), 7.85 (d, 1H), 7.91 (d, 1H), 8.11 (s, 1H), 8.28 (d, 1H), 8.37 (s, 1H), 8.68 (s, 1H).

Example 1.15

(RS)-S-({[3-(1[6-Bromo-4-(cyclobutylamino)quinazolin-7-yl]oxy}methyl)phenyl]-S-methylsulphoximide

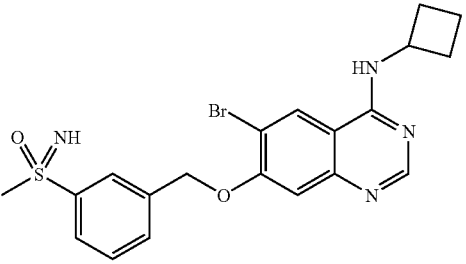

According to GWP 6, in the case of the reaction of (RS)-S-[3-({[6-bromo-4-(cyclo-butylamino)quinazolin-7-yl]oxy}methyl)phenyl]-N-(ethoxycarbonyl)-S-methylsulphoximide (45 mg, 0.084 mmol), the desired product is obtained after chromatographic purification (silica gel, dichloromethane/methanol: 0→25% methanol) in 88% yield (34 mg).

¹H-NMR (300 MHz, DMSO-d6): δ 1.67-1.79 (m, 2H), 2.05-2.20 (m, 2H), 2.28-2.35 (m, 2H), 3.09 (s, 3H), 4.28 (s, 1H), 4.60-4.75 (m, 1H), 5.47 (s, 2H), 7.33 (s, 1H), 7.68 (t, 1H), 7.80 (d, 1H), 7.93 (d, 1H), 8.12 (s, 1H), 8.33 (d, 1H), 8.42 (s, 1H), 8.72 (d, 1H).

Example 1.16

Ethyl 7-({(RS)-3-[N-(ethoxycarbonyl)-S-methylsulphonimidoyl]benzyl}oxy)-4-(isopropylamino)quinazoline-6-carboxylate

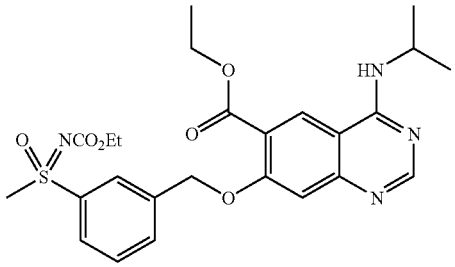

1.16. a) Preparation of the Intermediates

Compound 1.16. a.1

Ethyl-4-amino-5-cyano-2-hydroxybenzoate

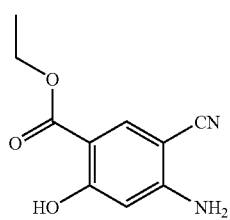

According to H.-W-. Schmidt et al. (Liebigs Ann. Chem. 1979, 2005-10), ethyl acetate (42 g, 323 mmol) is added to a solution of sodium (15 g, 23 mmol) in ethanol (4.0 l) and the mixture is stirred at room temperature for 30 minutes. Ethoxymethylene-malononitrile (40.6 g, 332 mmol) is added. After 30 minutes at 80° C., the reaction mixture is allowed to cool to room temperature and the resulting precipitate is filtered off with suction. The precipitate is dissolved using water, and the aqueous phase is acidified with concentrated hydrochloric acid and the resulting precipitate is filtered off with suction again. After recrystallization from acetic acid, the crystals are filtered off with suction, washed with water and subsequently dried. The desired product is obtained in 29% yield (21.5 g).

$^1$H-NMR (400 MHz, DMSO-d6): δ 1.30 (t, 3H), 4.28 (q, 2H), 6.20 (s, 1H), 6.80 (br s, 2H), 7.89 (s, 1H), 10.99 (s, 1H).

Compound 1.16. a.2

Ethyl 5-cyano-4-{(E/Z)-[(dimethylamino)methylene] amino}-2-hydroxybenzoate

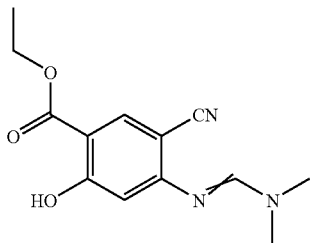

Ethyl 4-amino-5-cyano-2-hydroxybenzoate (8.3 g, 40.25 mmol) and dimethyl-formamide dimethyl acetal (38.4 g, 322 mmol) are combined and stirred at room temperature for 2 hours. The precipitate resulting during the reaction is filtered off with suction and washed with diethyl ether (7.0 g). The filtrate is concentrated and purified by chromatography (eluent: dichloromethane/methanol). The solid obtained in this way is stirred with diethyl ether, and subsequently filtered off with suction and dried (1.8 g). Altogether, the desired product is obtained in 83% yield (8.8 g).

$^1$H-NMR (400 MHz, DMSO-d6): δ 1.33 (t, 3H), 3.02 (s, 3H), 3.11 (s, 3H), 4.34 (q, 2H), 6.72 (s, 1H), 8.00 (s, 1H), 8.12 (s, 1H), 11.04 (s, 1H).

Compound 1.16. a.3

Ethyl 5-cyano-4-{(E/Z)-[(dimethylamino)methylene] amino}-2-({(RS)-3-[N-(ethoxycarbonyl)-S-methyl-sulphonimidoyl]benzyl}oxy)benzoate

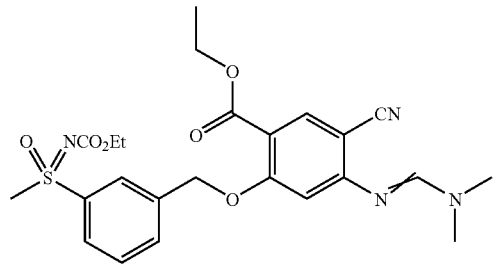

Ethyl 5-cyano-4-{(E/Z)-[(dimethylamino)methylene] amino}-2-hydroxybenzoate (30 mg, 0.12 mmol) and (RS)-S-[3-(bromomethyl)phenyl]-N-(ethoxycarbonyl)-S-methyl-sulphoximide (56 mg, 0.15 mmol) are dissolved in 1 ml of tetrahydrofuran. After addition of potassium carbonate (48 mg, 0.35 mmol), the reaction mixture is boiled at 50° C. for 20 hours. The batch is diluted with ethyl acetate, and the organic phase is washed with water and dried over sodium sulphate. After removing the solvent, the residue is reacted further as the crude product (64 mg, 84%).

LC-MS (Instrument: Micromass Quattro LCZ with HPLC Agilent Series 1100; column: Phenomenex Synergi 2.5μ MAX-RP 100A Mercury 20 mm×4 mm; eluent A: 1 l of water+0.5 ml of 50% strength formic acid, eluent B: 1 l of acetonitrile+0.5 ml of 50% strength formic acid; gradient: 0.0 min 90% A→0.1 min 90%A→3.0 min 5% A→4.0 min 5% A→4.1 min 90% A; flow: 2 ml/min; oven: 50° C.; UV detection: 208-400 nm): $R_t$=1.78 min; MS (ESI pos.): m/z=501 (M+H$^+$).

1.16. b) Preparation of the Final Product

According to GWP 5, ethyl 5-cyano-4-{(E/Z)-[(dimethylamino)methylene]amino}-2-({(RS)-3-[N-(ethoxycarbonyl)-S-methylsulphonimidoyl]benzyl}(oxy)benzoate (60 mg, 0.12 mmol) is reacted with isopropylamine (9.2 mg, 0.16 mmol). After cooling, the reaction mixture was diluted with water and sodium hydroxide solution (1N). The organic phase is separated off and dried over sodium sulphate. After concentrating the solvent, the residue (55 mg, 72%) is employed in the next reaction without further purification.

LC-MS (apparatus type MS: Micromass ZQ; apparatus type HPLC: Waters Alliance 2795; column: Phenomenex Synergi 2.5μ MAX-RP 100A Mercury 20 mm×4 mm; eluent A: 1 l water+0.5 ml 50% strength formic acid, eluent B: 1 l of acetonitrile+0.5 ml of 50% strength formic acid; gradient: 0.0 min 90% A→0.1 min 90% A→3.0 min 5% A→4.0 min 5% A→4.01 min 90% A; flow: 2 ml/min; oven: 50° C.; UV detection: 210 nm): $R_t$=1.78 min; MS (ESI pos.): m/z=515 (M+H$^+$).

Example 1.17

4-(Isopropylamino)-7-{[(RS)-3-(S-methylsulphonimidoyl)benzyl]oxy}-quinazoline-6-carboxylic acid

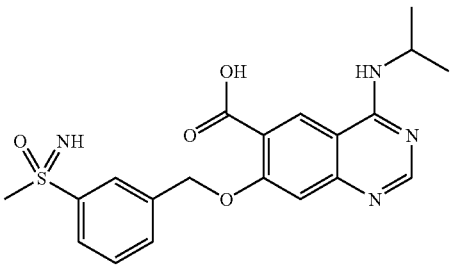

According to GWP 6, ethyl 7-({(RS)-3-[N-(ethoxycarbonyl)-S-methylsulphonimidoyl]-benzyl}oxy)-4-(isopropylamino)quinazoline-6-carboxylate (100 mg, 0.194 mmol) is reacted at 80° C. for 2 hours with sodium ethoxide (59 mg, 0.9 mmol). The reaction mixture is concentrated to dryness. The residue is taken up in ethyl acetate and water and acidified. The organic phase is separated off and subsequently concentrated. After chromatographic purification, the desired product is obtained in 35% yield (28 mg).

¹H-NMR (400 MHz, DMSO-d6): δ 1.28 (d, 6H), 3.09 (s, 3H), 3.17 (s, 1H), 4.53-4.62 (m, 1H), 5.46 (s, 2H), 7.28 (s, 1H), 7.66 (t, 1H), 7.81 (d, 1H), 7.91 (d, 1H), 8.14 (s, 1H), 8.59 (s, 1H), 8.83 (s, 1H), 8.86 (br s, 1H), 13.25 (br s, 1H).

Example 1.18

(RS)-S-[3-({[6-Bromo-4-(1,3,4-thiadiazol-2-ylamino)quinazolin-7-yl]oxy}methyl)-phenyl]-S-methylsulphoximide

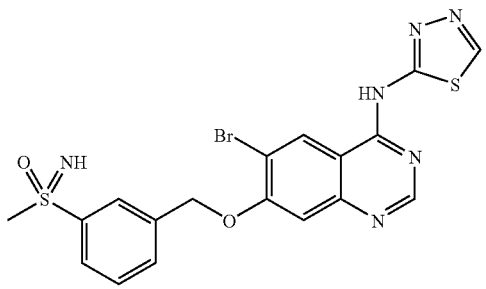

According to GWP 5, in the case of the reaction of (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (50 mg, 0.1 mmol) with 2-amino-1,3,4-thiadiazole (12 mg, 0.12 mmol) 34 mg of product is obtained after chromatographic purification (silica gel, dichloromethane/methanol: 0→30% methanol), which is employed in the next reaction.

According to GWP 6, in the case of the reaction of DSC3250 (32 mg), the desired product is obtained after chromatographic purification (silica gel, dichloromethane/methanol: 0→30% methanol) in 38% yield (19 mg, over 2 stages).

¹H-NMR (300 MHz, DMSO-d6): δ 3.05 (s, 3H), 4.22 (s, 1H), 5.39 (s, 2H), 7.12 (s, 1H), 7.64 (t, 1H), 7.77 (d, 1H), 7.87 (d, 1H), 8.09 (s, 1H), 8.32 (s, 1H), 8.52 (s, 1H), 8.68 (s, 1H).

Example 1.19

(RS)-S-[3-({[4-(Cyclopropylamino)-6-methoxyquinazolin-7-yl]oxy}methyl)-phenyl]-N-(ethoxycarbonyl)-S-methylsulphoximide

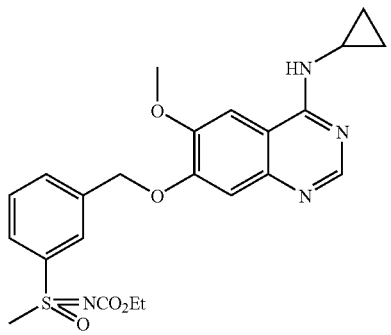

1.19. a) Preparation of the Intermediate

N'-(2-Cyano-5-{3-[(RS)-N-(ethoxycarbonyl)-S-methylsulphonimidoyl]benzyloxy}-4-methoxyphenyl)-N,N-dimethylformimidamide

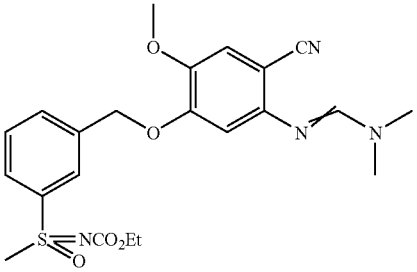

(E/Z)-N'-(2-Cyano-5-hydroxy-4-methoxyphenyl)-N,N-dimethylformimidamide (850 mg, 3.88 mmol) and (RS)-S-[3-(bromomethyl)phenyl]-N-(ethoxycarbonyl)-S-methylsulphoximide (1.86 g, 5.82 mmol) are suspended in 16 mL of acetone. After addition of potassium carbonate (992 mg, 7.17 mmol), the reaction mixture is refluxed for 6 hours. The batch is diluted with ethyl acetate and the organic phase is washed with water and dried over sodium sulphate to obtain, after removal of the solvent and also chromatographic purification (silica gel, hexane, dichloromethane/methanol: 0→10% methanol), the desired product in 88% yield (1.57 g).

¹H-NMR (300 MHz, DMSO): δ 1.03 (t, 3H), 2.92 (s, 3H), 3.02 (s, 3H), 3.44 (s, 3H), 3.70 (s, 3H), 3.81-3.91 (m, 2H), 5.26 (s, 2H), 6.86 (s, 1H), 7.11 (s, 1H), 7.69 (t, 1H), 7.79 (d, 1H), 7.84 (s, 1H), 7.90 (d, 1H), 8.04 (s, 1H).

1.19. b) Preparation of the Final Product

According to GWP 5, reaction of N'-(2-cyano-5-{3-[(RS)-N-(ethoxycarbonyl)-S-methylsulphonimidoyl]benzyloxy}-4-methoxyphenyl)-N,N-dimethylformimidamide (72 mg, 0.16 mmol) with cyclopropylamine (13 μL, 0.19 mmol) and chromatographic purification (silica gel, amino column, hexane, dichloromethane/methanol: 0→5% methanol) gives the desired product in 68% yield (50 mg).

¹H-NMR (300 MHz, DMSO): δ 0.55-0.60 (m, 2H), 0.74-0.80 (m, 2H), 1.02 (t, 3H), 2.91-2.94 (m, 1H), 3.44 (s, 3H), 3.80-3.90 (m, 5H), 5.34 (s, 2H), 7.20 (s, 1H), 7.56 (s, 1H), 7.70 (t, 1H), 7.81 (d, 1H), 7.89-7.92 (m, 2H), 8.06 (s, 1H), 8.35 (s, 1H).

Example 1.20

(RS)-S-[3-({[4-(Cyclopropylamino)-6-methoxyquinazolin-7-yl]oxy}methyl)-phenyl]-S-methylsulphoximide

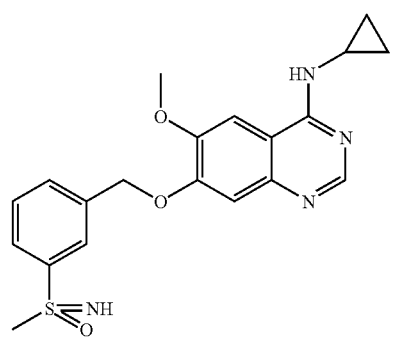

According to GWP 6, the conversion of (RS)-S-[3-({[4-(cyclopropylamino)-6-methoxy-quinazolin-7-yl]oxy}methyl)phenyl]-N-(ethoxycarbonyl)-S-methylsulphoximide (46 mg, 0.098 mmol) and preparative thin layer chromatography (silica gel, ethyl acetate/ethanol: 4/1) gives the desired product in 64% yield (25 mg).

¹H-NMR (300 MHz, DMSO): ∂ 0.55-0.60 (m, 2H), 0.75-0.80 (m, 2H), 2.88-2.95 (m, 1H), 3.04 (s, 3H), 3.85 (s, 3H), 4.23 (s, 1H), 5.31 (s, 2H), 7.18 (s, 1H), 7.56 (s, 1H), 7.61 (t, 1H), 7.72 (d, 1H), 7.87-7.92 (m, 2H), 8.03 (s, 1H), 8.35 (s, 1H).

Example 1.21

(RS)-S-[3-({[4-(Cyclobutylamino)-6-methoxyquinazolin-7-yl]oxy}methyl)phenyl]-N-(ethoxycarbonyl)-S-methylsulphoximide

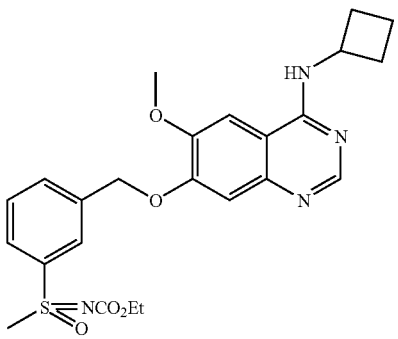

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (72 mg, 0.16 mmol) with cyclobutylamine (16 µL, 0.19 mmol) and chromatographic purification (silica gel, amino column, hexane, dichloromethane/methanol: 0→5% methanol) gives the desired product in 74% yield (56 mg).

¹H-NMR (300 MHz, DMSO): ∂ 1.07 (t, 3H), 1.69-1.81 (m, 2H), 2.09-2.16 (m, 2H), 2.32-2.41 (m, 2H), 3.49 (s, 3H), 3.84-3.95 (m, 5H), 4.68-4.76 (m, 1H), 5.38 (s, 2H), 7.23 (s, 1H), 7.68 (s, 1H), 7.75 (t, 1H), 7.87 (d, 1H), 7.94-7.89 (m, 2H), 8.11 (s, 1H), 8.32 (s, 1H).

Example 1.22

(RS)-S-[3-({[4-(Cyclobutylamino)-6-methoxyquinazolin-7-yl]oxy}methyl)phenyl]-S-methylsulphoximide

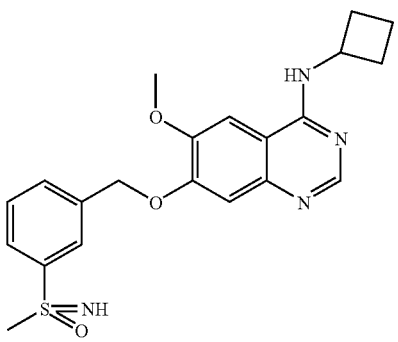

According to GWP 6, the conversion of (RS)-S-[3-({[4-(cyclobutylamino)-6-methoxy-quinazolin-7-yl]oxy}methyl)phenyl]-N-(ethoxycarbonyl)-S-methylsulphoximide (48 mg, 0.099 mmol) and preparative thin layer chromatography (silica gel, ethyl acetate/ethanol: 4/1) gives the desired product in 59% yield (24 mg).

¹H-NMR (300 MHz, DMSO): ∂ 1.64-1.76 (m, 2H), 2.01-2.11 (m, 2H), 2.23-2.35 (m, 2H), 3.04 (s, 3H), 3.88 (s, 3H), 4.23 (s, 1H), 4.60-4.70 (m, 1H), 5.31 (s, 7.17 (s, 1H), 7.59-7.64 (m, 2H), 7.73 (d, 1H), 7.87-7.94 (m, 2H), 8.03 (s, 1H), 8.27 (s, 1H).

Example 1.23

(RS)-N-(Ethoxycarbonyl)-S-methyl-S-[3-({[6-methoxy-4-(4-pyridylamino)-quinazolin-7-yl]oxy}methyl)phenyl]sulphoximide

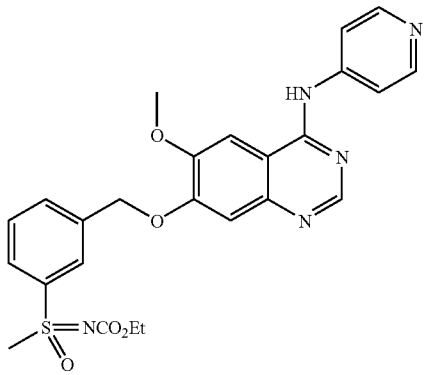

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (78 mg, 0.12 mmol) with 4-aminopyridine (19 mg, 0.20 mmol) and chromatographic purification (silica gel, amino column, hexane, dichloromethane/methanol: 0→5% methanol) gives the desired product in 34% yield (29 mg).

¹H-NMR (300 MHz, DMSO): ∂ 1.07 (t, 3H), 3.50 (s, 3H), 3.85-3.96 (m, 2H), 4.02 (s, 3H), 5.46 (s, 2H), 7.43 (s, 1H), 7.77 (t, 1H), 7.89-7.98 (m, 5H), 8.14 (s, 8.50 (d, 2H), 8.64 (s, 1H), 9.75 (s, 1H).

Example 1.24

(RS)-S-[3-({[6-Methoxy-4-(4-pyridylamino)quinazolin-7-yl]oxy}methyl)phenyl]-S-methylsulphoximide

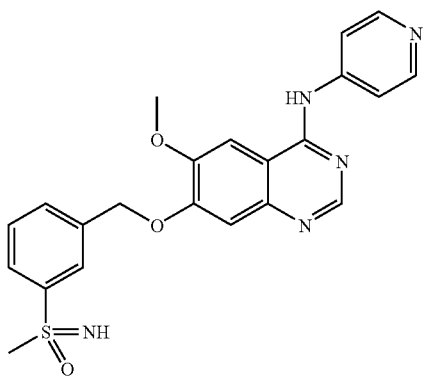

According to GWP 6, the conversion of (RS)-N-(ethoxycarbonyl)-S-methyl-S-[3-({[6-methoxy-4-(4-pyridylamino)quinazolin-7-yl]oxy}methyl)phenyl]sulphoximide (28 mg, 0.049 mmol) and preparative thin layer chromatography (silica gel, ethyl acetate/ethanol: 4/1) gives the desired product in 51% yield (11 mg).

$^1$H-NMR (300 MHz, DMSO): ∂ 3.05 (s, 3H), 3.97 (s, 3H), 4.25 (s, 1H), 5.38 (s, 2H), 7.37 (s, 1H), 7.63 (t, 1H), 7.76 (d, 1H), 7.87-7.93 (m, 4H), 8.06 (s, 1H), 8.45 (d, 2H), 8.59 (s, 1H), 9.71 (s, 1H).

Example 1.25

(RS)-N-(Ethoxycarbonyl)-S-methyl-S-[3-({[6-methoxy-4-(3-pyridylamino)-quinazolin-7-yl]oxy}methyl)phenyl]sulphoximide

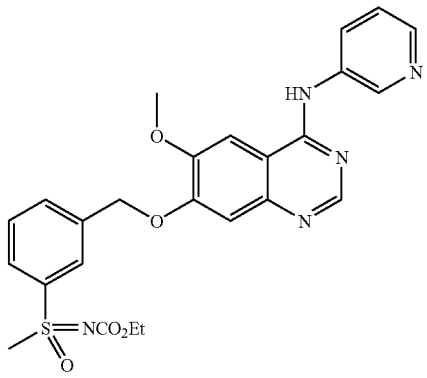

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (76 mg, 0.17 mmol) with 3-aminopyridine (19 mg, 0.20 mmol) and chromatographic purification (silica gel, amino column, hexane, dichloromethane/methanol: 0→5% methanol) gives the desired product in 55% yield (46 mg).

$^1$H-NMR (300 MHz, DMSO): ∂ 1.08 (t, 3H), 3.50 (s, 3H), 3.85-3.96 (m, 2H), 4.02 (s, 3H), 5.45 (s, 2H), 7.38 (s, 1H), 7.45 (dd, 1H), 7.76 (t, 1H), 7.89-7.99 (m, 3H), 8.14 (s, 1H), 8.24-8.27 (m, 1H), 8.32-8.34 (m, 1H), 8.50 (s, 1H), 8.96 (d, 1H), 9.60 (s, 1H).

Example 1.26

(RS)-S-[3-({[6-Methoxy-4-(3-pyridylamino)quinazolin-7-yl]oxy}methyl)-phenyl]-S-methylsulphoximide

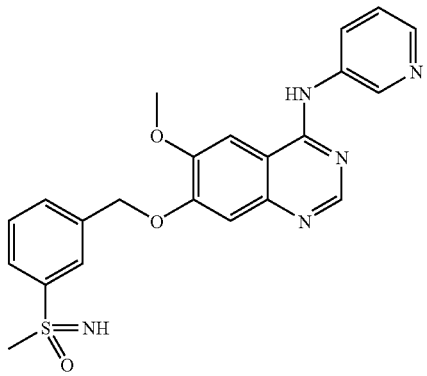

According to GWP 6, the conversion of (RS)-N-(ethoxycarbonyl)-S-methyl-S-[3-({[6-methoxy-4-(3-pyridylamino)quinazolin-7-yl]oxy}methyl)phenyl]sulphoximide (42 mg, 0.083 mmol) and preparative thin layer chromatography (silica gel, ethyl acetate/ethanol: 4/1) gives the desired product in 64% yield (23 mg).

$^1$H-NMR (300 MHz, DMSO): ∂ 3.05 (s, 3H), 3.95 (s, 3H), 4.25 (s, 1H), 5.37 (s, 2H), 7.32 (s, 1H), 7.40 (dd, 1H), 7.63 (t, 1H), 7.75 (d, 1H), 7.86 (s, 1H), 7.90 (d, 1H), 8.06 (s, 1H), 8.20-8.23 (m, 1H), 8.27-8.29 (m, 1H), 8.45 (s, 1H), 8.91 (d, 1H), 9.63 (s, 1H).

Example 1.27

(RS)-N-(Ethoxycarbonyl)-S-methyl-S-[3-({[6-methoxy-4-(thiazol-2-ylamino)-chinazolin-7-yl]oxy}methyl)phenyl]sulphoximide

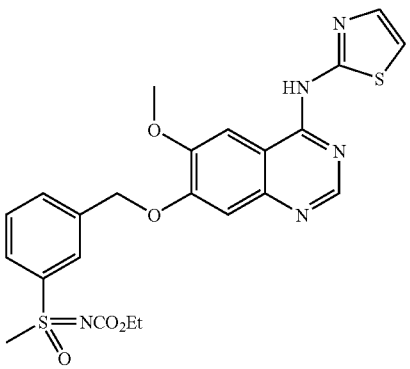

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (76 mg, 0.17 mmol) with 2-aminothiazole (20 mg, 0.20 mmol) and chromatographic purification (silica gel, amino column, hexane, dichloromethane/methanol: 0→5% methanol) gives the desired product in 67% yield (57 mg).

$^1$H-NMR (300 MHz, DMSO): ∂ 1.07 (t, 3H), 3.50 (s, 3H), 3.82-3.93 (m, 2H), 3.99 (s, 3H), 5.46 (s, 2H), 7.28 (d, 1H), 7.43 (s, 1H), 7.57 (d, 1H), 7.76 (t, 1H), 7.90 (d, 1H), 7.97 (d, 1H), 8.13 (s, 1H), 8.25 (br, 1H), 8.71 (s, 1H), 12.13 (s, 1H).

Example 1.28

(RS)-S-[3-({[6-Methoxy-4-(thiazol-2-yl-amino)quinazolin-7-yl]oxy}methyl)-phenyl]-S-methylsulphoximide

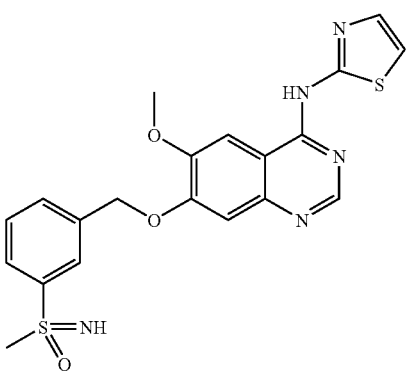

According to GWP 6, the conversion of (RS)-N-(ethoxycarbonyl)-S-methyl-S-[3-({[6-methoxy-4-(thiazolyl-2-amino)quinazolin-7-yl]oxy}methyl)phenyl]-sulphoximide (51 mg, 0.099 mmol) and stirring of the crude product in dichloromethane/methanol gives the desired product in 48% yield (21 mg).

¹H-NMR (300 MHz, DMSO): ∂ 3.05 (s, 3H), 3.94 (s, 3H), 4.25 (s, 1H), 5.38 (s, 2H), 7.21 (d, 1H), 7.37 (s, 1H), 7.52 (d, 1H), 7.63 (t, 1H), 7.75 (d, 1H), 7.90 (d, 1H), 8.06 (s, 1H), 8.14 (s, 1H), 8.65 (s, 1H), 12.13 (s, 1H).

Example 1.29

(RS)-N-(Ethoxycarbonyl)-S-methyl-S-[3-({[6-methoxy-4-(1,3,4-thiadiazol-2-ylamino)quinazolin-7-yl]oxy}methyl)phenyl]sulphoximide

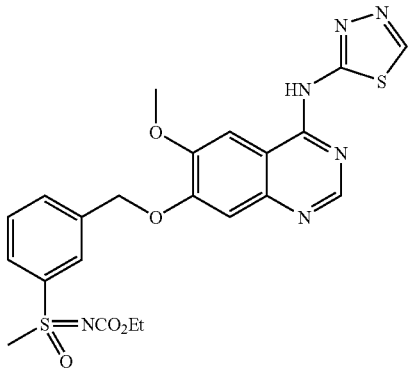

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (76 mg, 0.17 mmol) with 2-amino-1,3,4-thiadiazole (20 mg, 0.20 mmol) and chromatographic purification (silica gel, amino column, hexane, dichloromethane/methanol: 0→5% methanol) gives the desired product in 47% yield (40 mg).

¹H-NMR (300 MHz, DMSO): ∂ 1.02 (t, 3H), 3.45 (s, 3H), 3.80-3.90 (m, 2H), 3.95 (s, 3H), 5.42 (s, 2H), 7.41 (s, 1H), 7.72 (t, 1H), 7.85 (d, 1H), 7.92 (d, 1H), 8.09 (s, 1H), 8.15 (br, 1H), 8.69 (s, 1H), 9.16 (s, 1H), 12.5 (s, 1H).

Example 1.30

(RS)-S-[3-({[6-Methoxy-4-(1,3,4-thiadiazol-2-ylamino)quinazolin-7-yl]oxy}-methyl)phenyl]-S-methylsulphoximide

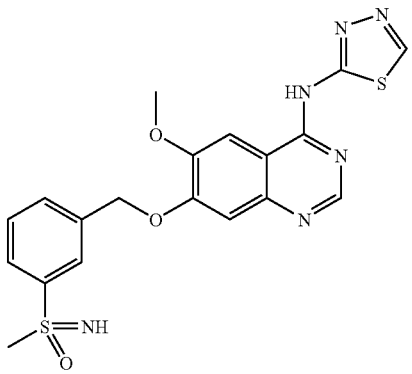

According to GWP 6, the reaction of (RS)-N-(ethoxycarbonyl)-S-methyl-S-[3-({[6-methoxy-4-(1,3,4-thiadiazol-2-ylamino)quinazolin-7-yl]oxy}methyl)phenyl]-sulphoximide (37 mg, 0.072 mmol) with sodium ethoxide (25 mg, 0.39 mmol) and chromatographic purification (silica gel, hexane, dichloromethane/methanol: 0→15% methanol) gives the desired product in 35% yield (11 mg).

¹H-NMR (300 MHz, DMSO): ∂ 3.05 (s, 3H), 3.95 (s, 3H), 4.25 (s, 1H), 5.39 (s, 2H), 7.40 (s, 1H), 7.63 (s, 1H), 7.75 (d, 1H), 7.90 (d, 1H), 8.06 (s, 1H), 8.15 (s, 8.68 (s, 1H), 9.15 (s, 1H), 12.5 (br, 1H).

Example 1.31

(RS)-S-[3-({[4-(Cyclopropylamino)-6-methoxyquinazolin-7-yl]oxy}methyl)-phenyl]-N-(ethoxycarbonyl)-S-ethylsulphoximide

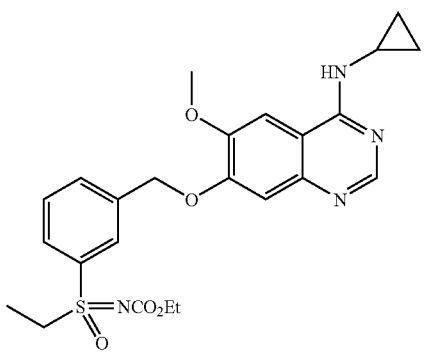

1.31. a) Preparation of the Intermediates

Compound 1.31. a.1

(RS)-N-(Ethoxycarbonyl)-S-ethyl-S-m-tolylsulphoximide

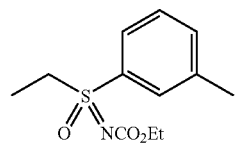

According to GWP 3, the conversion of (RS)-S-ethyl-S-(m-tolyl)sulphoximide (2.55 g, 13.91 mmol) and chromatographic purification (silica gel, hexane/ethyl acetate: 0→100% ethyl acetate) gives the desired product in 92% yield (3.27 g).

¹H-NMR (300 MHz, DMSO): ∂ 1.02-1.6 (m, 6H), 2.39 (s, 3H), 3.45-3.58 (m, 2H), 3.81-3.91 (m, 2H), 7.52-7.55 (m, 2H), 7.63-7.67 (m, 2H).

Compound 1.31. a.2

(RS)-S-[3-(Bromomethyl)phenyl]-N-(ethoxycarbonyl)-S-ethylsulphoximide

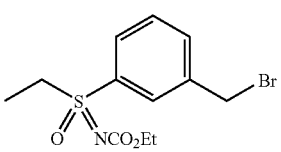

According to GWP 4, the conversion of (RS)-N-(ethoxycarbonyl)-S-ethyl-S-(m-tolyl)-sulphoximide (2.71 g, 11.2 mmol) and chromatographic purification (silica gel, hexane/ethyl acetate: 0→100% ethyl acetate, followed by ethyl acetate/methanol: 4/1) gives the desired product in 31% yield (1.1 g).

$^1$H-NMR (300 MHz, DMSO): ∂ 1.01-1.08 (m, 6H), 3.47-3.61 (m, 2H), 3.81-3.92 (m, 2H), 4.80 (s, 2H), 7.65 (t, 1H), 7.78-7.81 (m, 2H), 7.96 (t, 1H).

Compound 1.31. a.3

N'-(2-Cyano-5-{3-[(RS)-N-(ethoxycarbonyl)-S-ethylsulphonimidoyl]benzyloxy}-4-methoxyphenyl)-N,N-dimethylformimidamide

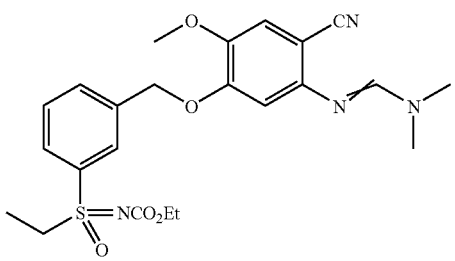

(E/Z)-N'-(2-Cyano-5-hydroxy-4-methoxyphenyl)-N,N-dimethylformimidamide (970 mg, 4.41 mmol) and (RS)-S-[3-(bromomethyl)phenyl]-N-(ethoxycarbonyl)-S-ethylsulphoximide (1.62 g, 4.85 mmol) are suspended in 18 mL of acetone. After addition of potassium carbonate (1.13 g, 8.15 mmol), the reaction mixture is refluxed for 6 hours. The batch is diluted with ethyl acetate and the organic phase is washed with water and dried over sodium sulphate to obtain, after removal of the solvent and also chromatographic purification (silica gel, hexane/ethyl acetate: 0→100% ethyl acetate, followed by ethyl acetate/methanol: 4/1), the desired product in 85% yield (1.77 g).

$^1$H-NMR (400 MHz, DMSO): ∂ 1.01-1.06 (m, 6H), 2.92 (s, 3H), 3.02 (s, 3H), 3.49-3.59 (m, 2H), 3.71 (s, 3H), 3.78-3.92 (m, 2H), 5.28 (s, 2H), 6.84 (s, 1H), 7.10 (s, 1H), 7.70 (t, 1H), 7.79 (d, 1H), 7.82-7.83 (m, 2H), 7.97 (s, 1H).

1.31. b) Preparation of the Final Product

According to GWP 5, the reaction of N'-(2-cyano-5-{3-[(RS)-N-(ethoxycarbonyl)-S-ethylsulphonimidoyl]benzyloxy}-4-methoxyphenyl)-N,N-dimethylformimidamide (50 mg, 0.11 mmol) with cyclopropylamine (7.3 mg, 0.13 mmol) and chromatographic purification (silica gel, dichloromethane/methanol: 0→30% methanol) gives the desired product in 92% yield (47 mg).

$^1$H-NMR (300 MHz, DMSO): ∂ 0.55-0.60 (m, 2H), 0.74-0.80 (m, 2H), 0.99-1.06 (m, 6H), 2.92-2.95 (m, 1H), 3.47-3.58 (m, 2H), 3.78-3.92 (m, 5H), 5.35 (s, 2H), 7.18 (s, 1H), 7.56 (s, 1H), 7.70 (t, 1H), 7.82-7.85 (m, 2H), 7.90 (d, 1H), 7.99 (s, 1H) 8.35 (s, 1H).

Example 1.32

(RS)-S-[3-({[4-(Cyclopropylamino)-6-methoxyquinazolin-7-yl]oxy}methyl)-phenyl]-S-ethylsulphoximide

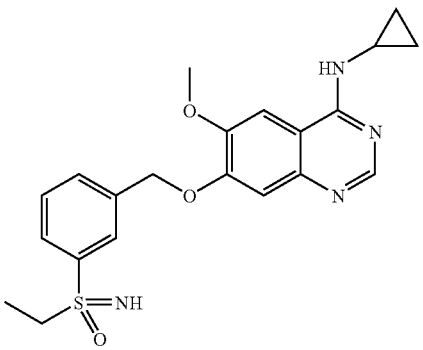

According to GWP 6, the conversion of (RS)-S-[3-({[4-(cyclopropylamino)-6-methoxy-quinazolin-7-yl]oxy}methyl)phenyl]-N-(ethoxycarbonyl)-S-ethylsulphoximide (47 mg, 0.097 mmol) and chromatographic purification (silica gel, dichloromethane/methanol: 0→30% methanol) gives the desired product in 92% yield (37 mg).

$^1$H-NMR (300 MHz, DMSO): ∂ 0.60-0.65 (m, 2H), 0.78-0.85 (m, 2H), 1.05 (t, 3H), 2.94-3.00 (m, 1H), 3.09-3.19 (m, 2H), 3.90 (s, 3H), 4.23 (s, 1H), 5.37 (s, 2H), 7.22 (s, 1H), 7.60 (s, 1H), 7.66 (t, 1H), 7.78 (d, 1H), 7.87 (d, 1H), 7.95 (d, 1H), 8.02 (s, 1H), 8.39 (s, 1H).

Example 1.33

(RS)-S-[3-({[4-(Cyclobutylamino)-6-methoxyquinazolin-7-yl]oxy}methyl)phenyl]-N-(ethoxycarbonyl)-S-ethylsulphoximide

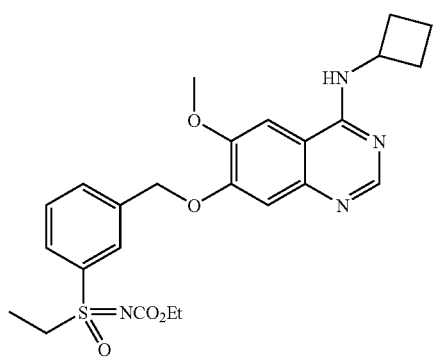

According to GWP 5, the reaction of N'-(2-cyano-5-{3-[(RS)-N-(ethoxycarbonyl)-S-ethylsulphonimidoyl]benzyloxy}-4-methoxyphenyl)-N,N-dimethylformimidamide (50 mg, 0.11 mmol) with cyclobutylamine (9.1 mg, 0.13 mmol) and chromatographic purification (silica gel, dichloromethane/methanol: 0→30% methanol) gives the desired product in 91% yield (48 mg).

$^1$H-NMR (300 MHz, DMSO): ∂ 0.99-1.06 (m, 6H), 1.64-1.76 (m, 2H), 2.02-2.15 (m, 2H), 2.23-2.36 (m, 2H), 3.47-3.60 (m, 2H), 3.76-3.92 (m, 5H), 4.60-4.75 (m, 1H), 5.35 (s, 2H), 7.16 (s, 1H), 7.63 (s, 1H), 7.70 (t, 1H), 7.82-7.85 (m, 2H), 7.93 (d, 1H), 7.99 (s, 1H), 8.27 (s, 1H).

Example 1.34

(RS)-S-[3-({[4-(Cyclobutylamino)-6-methoxyquinazolin-7-yl]oxy}methyl)-phenyl]-S-ethylsulphoximide

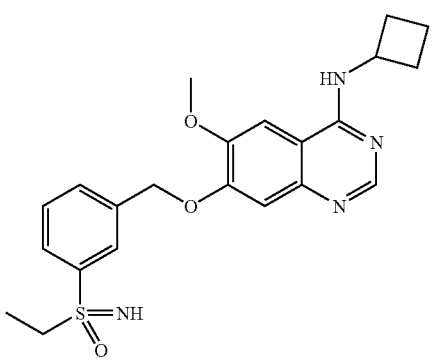

According to GWP 6, the conversion of (RS)-S-[3-({[4-(cyclobutylamino)-6-methoxy-quinazolin-7-yl]oxy}methyl)phenyl]-N-(ethoxycarbonyl)-S-ethylsulphoximide (48 mg, 0.096 mmol) and chromatographic purification (silica gel, dichloromethane/methanol: 0→30% methanol) gives the desired product in 94% yield (39 mg).

$^1$H-NMR (400 MHz, DMSO): ∂ 1.01 (t, 3H), 1.65-1.75 (m, 2H), 2.03-2.13 (m, 2H), 2.27-2.34 (m, 2H), 3.06-3.14 (m, 2H), 3.89 (s, 3H), 4.20 (s, 1H), 4.62-4.73 (m, 1H), 5.32 (s, 2H), 7.15 (s, 1H), 7.60-7.64 (m, 2H), 7.74 (d, 1H), 7.82 (d, 1H), 7.94 (d, 1H), 7.97 (s, 1H), 8.27 (s, 1H).

Example 1.35

(RS)-N-(Ethoxycarbonyl)-S-ethyl-S-[3-({[6-methoxy-4-(thiazol-2-ylamino)-quinazolin-7-yl]oxy}methyl)phenyl]sulphoximide

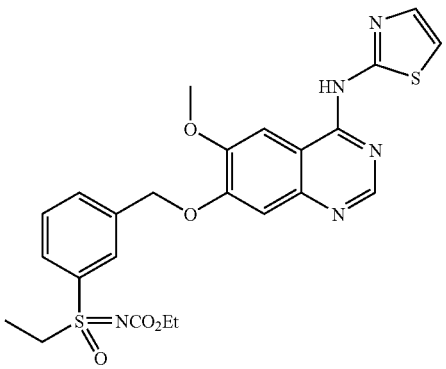

According to GWP 5, the reaction of N'-(2-cyano-5-{3-[(RS)-N-(ethoxycarbonyl)-S-ethylsulphonimidoyl]benzyloxy}-4-methoxyphenyl)-N,N-dimethylformimidamide (50 mg, 0.11 mmol) with 2-aminothiazole (12.8 mg, 0.13 mmol) and chromatographic purification (silica gel, dichloromethane/methanol: 0→30% methanol) gives the desired product in 72% yield (40 mg).

$^1$H-NMR (400 MHz, DMSO): ∂ 1.00-1.07 (m, 6H), 3.49-3.60 (m, 2H), 3.78-3.91 (m, 2H), 3.94 (s, 3H), 5.43 (s, 2H), 7.23 (br, 1H), 7.37 (s, 1H), 7.53 (d, 1H), 7.72 (t, 1H), 7.84-7.87 (m, 2H), 8.02 (s, 1H), 8.17 (br, 1H), 8.65 (s, 1H), 12.07 (s, 1H).

Example 1.36

(RS)-S-Ethyl-S-[3-({[6-methoxy-4-(thiazol-2-ylamino)quinazolin-7-yl]oxy}-methyl)phenyl]sulphoximide

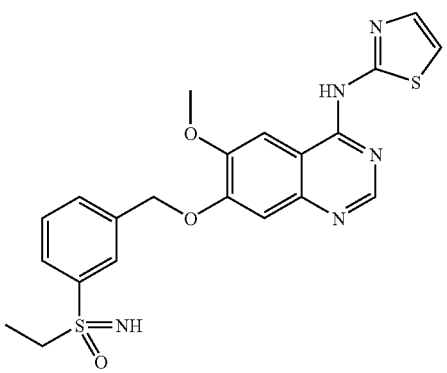

According to GWP 6, the conversion of (RS)-N-(ethoxycarbonyl)-S-ethyl-S-[3-({[6-methoxy-4-(thiazol-2-ylamino)quinazolin-7-yl]oxy}methyl)phenyl]-sulphoximide (40 mg, 0.076 mmol) and chromatographic purification (silica gel, dichloromethane/methanol: 0→30% methanol) gives the desired product in 66% yield (23 mg).

$^1$H-NMR (400 MHz, DMSO): ∂ 1.01 (t, 3H), 3.09 (q, 2H), 3.94 (s, 3H), 4.23 (br, 1H), 5.40 (s, 2H), 7.23 (s, 1H), 7.36 (s, 1H), 7.63 (t, 1H), 7.76 (d, 1H), 7.84 (d, 1H), 8.00 (s, 1H), 8.15 (br, 1H), 8.65 (s, 1H), 12.08 (br, 1H).

Example 1.37

(RS)-S-Ethyl-S-[3-({[6-methoxy-4-(1H-pyrazol-3-ylamino)quinazolin-7-yl]oxy}-methyl)phenyl]sulphoximide

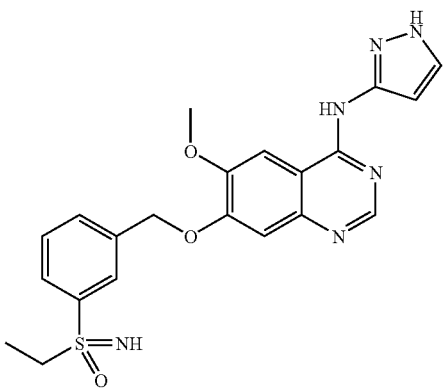

According to GWP 5, the reaction of N'-(2-cyano-5-{3-[(RS)-N-(ethoxycarbonyl)-S-ethylsulphonimidoyl]benzyloxy}-4-methoxyphenyl)-N,N-dimethylformimidamide (50 mg, 0.11 mmol) with 3-aminopyrazole (10.6 mg, 0.13 mmol) and chromatographic purification (silica gel, dichloromethane/methanol: 0→30% methanol) gives 44 g of product which is subsequently reacted with sodium ethoxide (19 mg, 0.31 mmol) according to GWP 6.

Chromatographic purification (silica gel, dichloromethane/methanol: 0→30% methanol) gives via 2 stages the desired product in 55% yield (26 mg).

$^1$H-NMR (300 MHz, DMSO): ∂ 1.06 (t, 3H), 3.10-3.20 (m, 2H), 3.96 (s, 3H), 4.25 (s, 1H), 5.41 (s, 2H), 6.83 (s, 1H), 7.29 (s, 1H), 7.65-7.70 (m, 2H), 7.80 (d, 7.87 (d, 1H), 8.03 (s, 2H), 8.46 (s, 1H), 10.23 (s, 1H), 12.43 (s, 1H).

Example 1.38

(RS)-S-Ethyl-S-[3-({[6-methoxy-4-(oxazo-3-ylamino)quinazolin-7-yl]oxy}-methyl)phenyl]sulphoximide

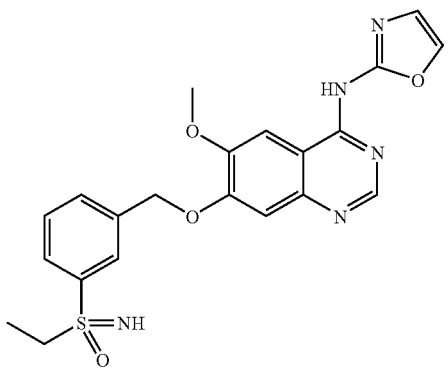

According to GWP 5, the reaction of N'-(2-cyano-5-{3-[(RS)-N-(ethoxycarbonyl)-S-ethylsulphonimidoyl]benzyloxy}-4-methoxyphenyl)-N,N-dimethylformimidamide (50 mg, 0.11 mmol) with 2-aminooxazole (11 mg, 0.13 mmol) and chromatographic purification (silica gel, dichloromethane/methanol: 0→30% methanol) gives 39 g of product which is subsequently reacted with sodium ethoxide (17 mg, 0.27 mmol) according to GWP 6.

Chromatographic purification (silica gel, dichloromethane/methanol: 0→30% methanol) gives via 2 stages the desired product in 33% yield (16 mg).

$^1$H-NMR (400 MHz, DMSO): ∂ 1.01 (t, 3H), 3.09 (q, 2H), 3.90 (s, 3H), 4.21 (s, 1H), 5.38 (s, 2H), 7.23 (d, 1H), 7.28 (s, 1H), 7.63 (t, 1H), 7.69 (s, 1H), 7.75 (d, 1H), 7.77 (d, 1H), 7.83 (d, 1H), 7.98 (s, 1H), 8.30 (d, 1H), 13.37 (s, 1H).

Example 1.39

(RS)-S-[3-({[6-Methoxy-4-(oxazo-3-ylamino)quinazolin-7-yl]oxy}methyl)phenyl]-S-methylsulphoximide

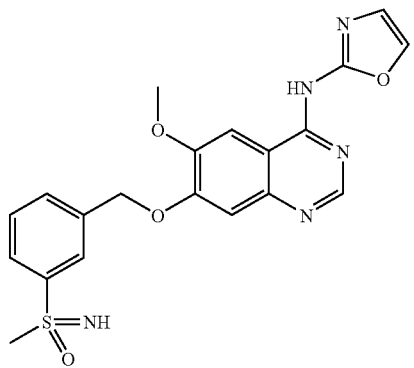

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (142 mg, 0.31 mmol) with 2-aminooxazole (32 mg, 0.37 mmol) and chromatographic purification (silica gel, dichloromethane/methanol: 0→10% methanol) gives 91 mg of product which is subsequently reacted with sodium ethoxide (40 mg, 0.65 mmol) according to GWP 6.

Preparative thin layer chromatography (silica gel, dichloromethane/methanol: 9/1) gives via 2 stages the desired product in 9% yield (12 mg).

$^1$H-NMR (400 MHz, DMSO): ∂ 3.05 (s, 3H), 3.90 (s, 3H), 4.25 (s, 1H), 5.37 (s, 2H), 7.23 (d, 1H), 7.30 (s, 1H), 7.63 (t, 1H), 7.70 (s, 1H), 7.74 (d, 1H), 7.77 (d, 1H), 7.89 (d, 1H), 8.04 (s, 1H), 8.31 (d, 1H), 13.37 (s, 1H).

Example 1.40

(RS)-S-(3-{[(6-Bromo-4-{[2-hydroxy-1-(hydroxymethyl)ethyl]amino}quinazolin-7-yl)oxy]methyl}phenyl)-N-(ethoxycarbonyl)-S-methylsulphoximide

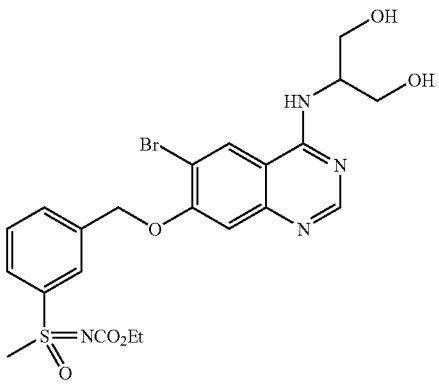

According to GWP 5, the reaction of (E/Z)-N'-(4-bromo-2-cyano-5-{3-[(RS)-N-(ethoxycarbonyl)-S-methylsulphonimidoyl]benzyloxy}phenyl)-N,N-dimethyl-formimidamide (113 mg, 0.22 mmol) with 2-amino-1,3-propanediol (25 mg, 0.27 mmol) and chromatographic purification (silica gel, dichloromethane/methanol: 0→10% methanol) gives the desired product in 44% yield (54 mg).

$^1$H-NMR (300 MHz, DMSO): ∂ 1.07 (t, 3H) 3.49 (s, 3H), 3.79-3.95 (m, 4H), 4.40-4.52 (m, 2H), 4.95 (m, 1H), 5.21 (t, 1H), 5.54 (s, 2H), 7.42 (s, 1H), 7.77 (t, 1H), 7.89 (d, 1H), 7.96 (d, 1H), 8.15 (s, 1H), 8.30 (s, 1H), 8.44 (s, 1H).

Example 1.41

(RS)-S-(3-{[(6-Bromo-4-{[2-hydroxy-1-(hydroxymethyl)ethyl]amino}quinazolin-7-yl)oxy]methyl}phenyl)-S-methylsulphoximide

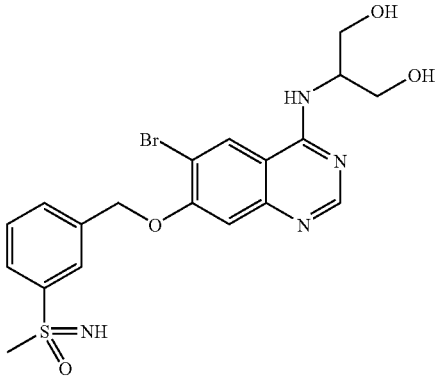

According to GWP 6, the conversion of (RS)-S-(3-{[(6-bromo-4-{[2-hydroxy-1-(hydroxymethyl)ethyl]

amino}quinazolin-7-yl)oxy]methyl}phenyl)-N-(ethoxycarbonyl)-S-methylsulphoximide (45 mg, 0.081 mmol) and preparation thin layer chromatography (silica gel, dichloromethane/methanol: 4/1) gives the desired product in 24% yield (9 mg).

$^1$H-NMR (300 MHz, DMSO): ∂ 3.09 (s, 3H), 3.70-3.87 (m, 4H), 4.28 (s, 1H), 4.76 (m, 1H), 5.02 (t, 2H), 5.51 (s, 2H), 7.41 (s, 1H), 7.70 (d, 1H), 7.93 (d, 1H), 8.12 (s, 1H), 8.29(s, 1H), 8.31 (s, 1H).

Example 1.42

(RS)-S-[3-({[6-Bromo-4-(2-hydroxyethylamino)quinazolin-7-yl]oxy}methyl)-phenyl]-N-(ethoxycarbonyl)-S-methylsulphoximide

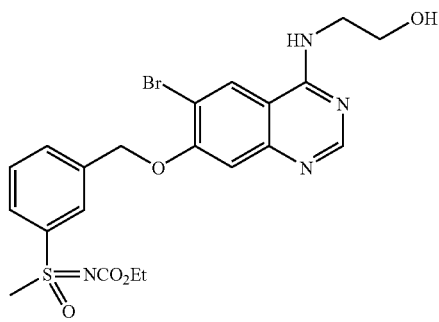

According to GWP 5, the reaction of (E/Z)-N'-(4-bromo-2-cyano-5-{3-[(RS)-N-(ethoxycarbonyl)-S-methylsulphonimidoyl]benzyloxy}phenyl)-N,N-dimethyl-formimidamide (113 mg, 0.22 mmol) with 2-aminoethanol (0.016 mL, 0.27 mmol) and chromatographic purification (silica gel, dichloromethane/methanol: 0→10% methanol) gives the desired product in 66% yield (77 mg).

$^1$H-NMR (300 MHz, DMSO): ∂ 1.07 (t, 3H) 3.48 (s, 3H), 3.57-3.63 (m, 4H), 3.84-3.98 (m, 2H), 4.81 (t, 1H), 5.50 (s, 2H), 7.35 (s, 1H), 7.77 (t, 1H), 7.90 (d, 1H), 7.96 (d, 1H), 8.15 (s, 1H), 8.29 (t, 1H), 8.43 (s, 1H), 8.67 (s, 1H).

Example 1.43

(RS)-S-[3-({[6-Bromo-4-(2-hydroxyethylamino)quinazolin-7-yl]oxy}methyl)-phenyl]-S-methylsulphoximide

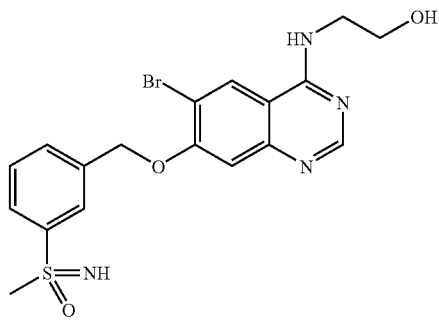

According to GWP 6, (RS)-S-[3-({[6-bromo-4-(2-hydroxyethylamino)quinazolin-7-yl]oxy}methyl)phenyl]-N-(ethoxycarbonyl)-S-methylsulphoximide (67 mg, 0.13 mmol) is reacted with sodium ethoxide (29 mg, 0.46 mmol) in ethanol (3 mL). After cooling to room temperature, the reaction mixture is admixed with brine and stirred for 30 minutes and the resulting precipitate is filtered off with suction to leave the desired product in 81% yield (47 mg).

$^1$H-NMR (300 MHz, DMSO): ∂ 3.09 (s, 3H), 3.57-3.60 (m, 4H), 4.28 (s, 1H), 4.81 (br, 1H), 5.47 (s, 2H), 7.34 (s, 1H), 7.68 (t, 1H), 7.80 (d, 1H), 7.93 (d, 1H), 8.12 (s, 1H), 8.28 (t, 1H), 8.42 (s, 1H), 8.66 (s, 1H).

Example 1.44

(RS)-N-(Ethoxycarbonyl)-S-methyl-S-[4-({[6-methoxy-4-(3-pyridylamino)-quinazolin-7-yl]oxy}methyl)phenyl]sulphoximide

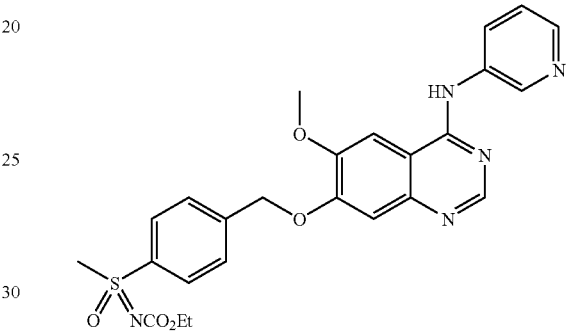

1.44. a) Preparation of the Intermediate

N'-(2-Cyano-5-{4-[(RS)-N-(ethoxycarbonyl)-S-methylsulphonimidoyl]benzyloxy}-4-methoxyphenyl)-N,N-dimethylformimidamide

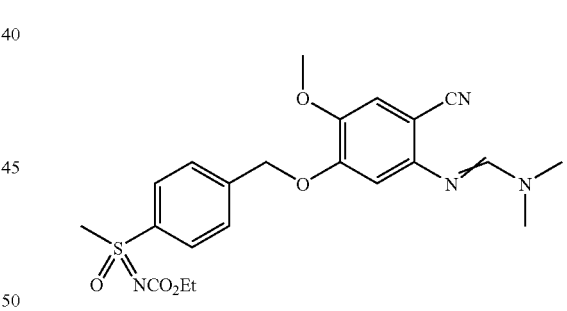

(E/Z)-N'-(2-Cyano-5-hydroxy-4-methoxyphenyl)-N,N-dimethylformimidamide (268 mg, 1.22 mmol) and (RS)-S-[4-(bromomethyl)phenyl]-N-(ethoxycarbonyl)-S-ethylsulphoximide (430 g, 1.34 mmol) are suspended in 5 mL of acetone. After addition of potassium carbonate (312 mg, 2.26 mmol), the reaction mixture is refluxed for 6 hours. The batch is diluted with ethyl acetate and the organic phase is washed with water and dried over sodium sulphate to obtain, after removal of the solvent and also chromatographic purification (silica gel, hexane/ethyl acetate: 0→70% ethyl acetate, followed by ethyl acetate/methanol: 0→20% methanol), the desired product in 32% yield (180 mg).

$^1$H-NMR (300 MHz, DMSO): ∂ 1.09 (t, 3H), 2.97 (s, 3H), 3.07 (s, 3H), 3.48 (s, 3H), 3.76 (s, 3H), 3.86-3.97 (m, 2H), 5.31 (s, 2H), 6.89 (s, 1H), 7.16 (s, 1H), 7.74 (d, 2H), 7.89 (s, 1H), 8.00 (d, 2H).

1.44. b) Preparation of the Final Product

According to GWP 5, the reaction of N'-(2-cyano-5-{4-[(RS)-N-(ethoxycarbonyl)-S-methylsulphonimidoyl]benzyloxy}-4-methoxyphenyl)-N,N-dimethylformimidamide (85 mg, 0.19 mmol) with 3-aminopyridine (21 mg, 0.22 mmol) and chromatographic purification (silica gel, dichloromethane/methanol: 0→30% methanol) gives the desired product in 42% yield (39 mg).

¹H-NMR (400 MHz, DMSO): ∂ 1.05 (t, 3H), 3.44 (s, 3H), 3.83-3.91 (m, 2H), 3.97 (s, 3H), 5.42 (s, 2H), 7.30 (s, 1H), 7.39 (dd, 1H), 7.76 (d, 2H), 7.86 (s, 1H), 7.97 (d, 2H), 8.19-8.22 (m, 1H), 8.28 (d, 1H), 8.45 (s, 1H), 8.92 (d, 1H), 9.63 (s, 1H).

Example 1.45

(RS)-S-[4-({[6-Methoxy-4-(3-pyridylamino)quinazolin-7-yl]oxy}methyl)phenyl]-S-methylsulphoximide

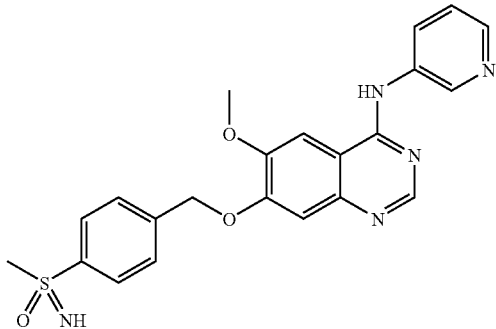

According to GWP 6, the conversion of (RS)-N-(ethoxycarbonyl)-S-methyl-S-[4-({[6-methoxy-4-(3-pyridylamino)quinazolin-7-yl]oxy}methyl)phenyl]sulphoximide (33 mg, 0.064 mmol) and chromatographic purification (silica gel, dichloromethane/methanol: 0→30% methanol) gives the desired product in 61% yield (17 mg).

¹H-NMR (300 MHz, DMSO): ∂ 3.09 (s, 3H), 4.01 (s, 3H), 4.26 (s, 1H), 5.44 (s, 2H), 7.33 (s, 1H), 7.45 (dd, 1H), 7.73 (d, 2H), 7.90 (s, 1H), 7.99 (d, 2H), 8.24-8.27 (m, 1H), 8.32-8.34 (m, 1H), 8.49 (s, 1H), 8.95 (d, 1H), 9.68 (s, 1H).

Example 1.46

(RS)-N-(Ethoxycarbonyl)-S-methyl-S-[4-({[6-methoxy-4-(1,3,4-thiadiazol-2-yl-amino)quinazolin-7-yl]oxy}methyl)phenyl]sulphoximide

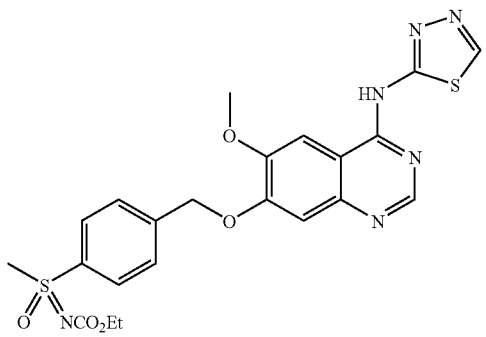

According to GWP 5, the reaction of N'-(2-cyano-5-{4-[(RS)-N-(ethoxycarbonyl)-S-methylsulphonimidoyl]benzyloxy}-4-methoxyphenyl)-N,N-dimethylformimidamide (85 mg, 0.19 mmol) with 2-amino-1,3,4-thiadiazole (23 mg, 0.22 mmol) and chromatographic purification (silica gel, dichloromethane/methanol: 0→30% methanol) gives the desired product in 40% yield (38 mg).

¹H-NMR (400 MHz, DMSO): ∂ 1.04 (t, 3H), 3.44 (s, 3H), 3.81-3.93 (m, 2H), 3.96 (s, 3H), 5.44 (s, 2H), 7.38 (s, 1H), 7.76 (d, 2H), 7.97 (d, 2H), 8.19 (s, 1H), 8.68 (s, 1H), 9.17 (s, 1H), 12.48 (s, 1H).

Example 1.47

(RS)-S-[4-({[6-Methoxy-4-(1,3,4-thiadiazol-2-ylamino)quinazolin-7-yl]oxy}-methyl)phenyl]-S-methylsulphoximide

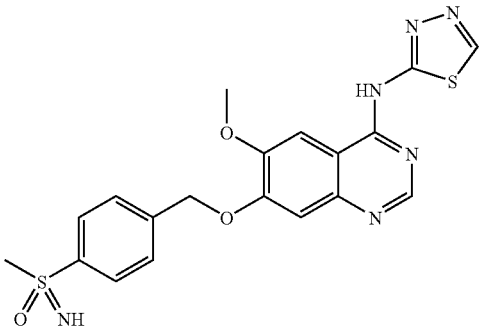

According to GWP 6, the conversion of (RS)-N-(ethoxycarbonyl)-S-methyl-S-[4-({[6-methoxy-4-(1,3,4-thiadiazol-2-ylamino)quinazolin-7-yl]oxy}methyl)-phenyl]sulphoximide (33 mg, 0.064 mmol) and chromatographic purification (silica gel, dichloromethane/methanol: 0→30% methanol) gives the desired product in 74% yield (21 mg).

¹H-NMR (300 MHz, DMSO): ∂ 3.09 (s, 3H), 4.00 (s, 3H), 4.26 (s, 1H), 5.46 (s, 2H), 7.40 (s, 1H), 7.73 (d, 2H), 7.99 (d, 2H), 8.20 (s, 1H), 8.72 (s, 1H), 9.20 (s, 1H), 12.58 (s, 1H).

Example 1.48

(RS)-S-[3-({[4-(Cyclopropylamino)quinazolin-7-yl]amino}methyl)phenyl]-N-(ethoxycarbonyl)-S-methylsulphoximide

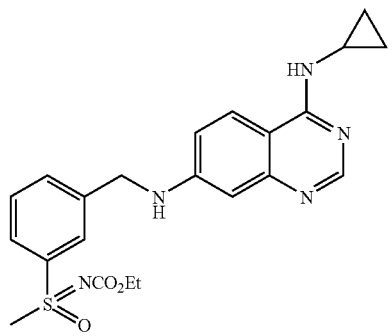

1.48. a) Preparation of the Intermediates

Compound 1.48. a.1

N'-(5-Amino-2-cyanophenyl)-N,N-dimethylformimidamide

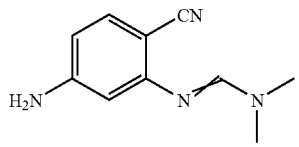

N'-(2-Cyano-5-nitrophenyl)-N,N-dimethylformimidamide (1.0 g, 4.58 mmol) is dissolved in 100 mL of tetrahydrofuran, cooled to 0° C. and admixed with titanium trichloride solution (69 mL of a 15% solution in 10% aqueous HCl). Then, the batch is stirred at room temperature for 4 hours and adjusted at 0° C. to pH 9 with 2N aqueous sodium hydroxide solution. The mixture is diluted with water and ethyl acetate. The aqueous phase is saturated with sodium chloride and stirred out three times with ethyl acetate. The combined organic phases are dried over sodium sulphate. Removal of the solvent and also chromatographic purification (silica gel, n-hexane/ethyl acetate:→100% ethyl acetate) gives the desired product in 73% yield (630 mg).

$^1$H-NMR (300 MHz, DMSO): ∂ 2.93 (s, 3H), 3.03 (s, 3H), 5.81 (s, 2H), 6.09 (d, 1H), 6.21 (dd, 1H), 7.18 (d, 1H), 7.70 (s, 1H).

Compound 1.48. a.2

N'-(2-Cyano-5-{3-[(RS)-N-(ethoxycarbonyl)-S-methylsulphonimidoyl]benzylamino}-phenyl)-N,N-dimethylformimidamide

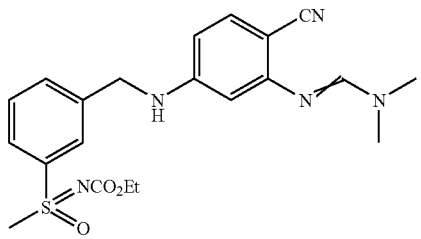

N'-(5-Amino-2-cyanophenyl)-N,N-dimethylformimidamide (50 mg, 0.27 mmol) and (RS)-S-[3-(bromomethyl)phenyl]-N-(ethoxycarbonyl)-S-methylsulphoximide (85 mg, 0.27 mmol) are dissolved in 4 mL of dimethylformamide. After addition of potassium carbonate (68 mg, 0.49 mmol), the reaction mixture is stirred at 110° C. for 4 hours. The batch is diluted with ethyl acetate and the organic phase is washed with water and dried over sodium sulphate to leave, after removal of the solvent and also after chromatographic purification (silica gel, hexane/ethyl acetate: 0→100% ethyl acetate), the desired product in 36% yield (40 mg).

$^1$H-NMR (300 MHz, DMSO): ∂ 1.01 (t, 3H), 2.88 (s, 3H), 2.97 (s, 3H), 3.40 (s, 3H), 3.77-3.86 (m, 2H), 4.42 (d, 2H), 6.11 (d, 1H), 6.24 (dd, 1H), 7.03 (t, 1H), 7.18 (d, 1H), 7.58-7.67 (m, 3H), 7.79 (d, 1H), 7.91 (s, 1H).

1.48. b) Preparation of the Final Product

According to GWP 5, reaction of N'-(2-cyano-5-{3-[(RS)-N-(ethoxycarbonyl)-S-methylsulphonimidoyl]benzylamino}phenyl)-N,N-dimethylformimidamide (80 mg, 0.19 mmol) with cyclopropylamine (13 mg, 0.22 mmol) and chromatographic purification (silica gel, n-hexane/ethyl acetate: 0→100% ethyl acetate, followed by dichloromethane/methanol: 0→20% methanol) gives the desired product in 74% yield (61 mg).

$^1$H-NMR (300 MHz, DMSO): ∂ 0.55-0.60 (m, 2H), 0.74-0.78 (m, 2H), 1.03 (t, 3H), 2.91-2.97 (m, 1H), 3.44 (s, 3H), 3.81-3.91 (m, 2H), 4.53 (d, 2H), 6.49 (d, 1H), 6.90 (dd, 1H), 7.14 (t, 1H), 7.74-7.76 (m, 2H), 7.83 (d, 1H), 7.90 (d, 1H), 7.98 (s, 1H), 8.26 (s, 1H).

Example 1.49

(RS)-S-[3-({[4-(Cyclopropylamino)quinazolin-7-yl]amino}methyl)phenyl]-S-methylsulphoximide

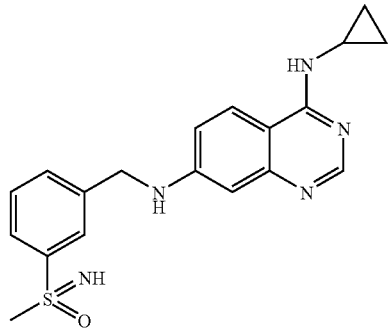

According to GWP 6, conversion of (RS)-S-[3-({[4-(cyclopropylamino)quinazolin-7-yl]amino}methyl)phenyl]-N-(ethoxycarbonyl)-S-methylsulphoximide (58 mg, 0.13 mmol) and chromatographic purification (silica gel, n-hexane/ethyl acetate: 0→100% ethyl acetate, followed by dichloromethane/methanol: 0→25% methanol) gives the desired product in 74% yield (36 mg).

$^1$H-NMR (400 MHz, DMSO): ∂ 0.51-0.55 (m, 2H), 0.68-0.72 (m, 2H), 2.28-2.91 (m, 1H), 2.99 (s, 3H), 4.14 (s, 1H), 4.45 (d, 2H), 6.43 (d, 1H), 6.86 (dd, 1H), 7.09 (t, 1H), 7.53 (t, 1H), 7.60 (d, 1H), 7.72 (d, 1H), 7.77 (d, 1H), 7.85 (d, 1H), 7.92 (s, 1H), 8.21 (s, 1H).

Example 1.50

(RS)-N-(Ethoxycarbonyl)-S-methyl-S-[3-({[4-(3-pyridylamino)quinazolin-7-yl]-amino}methyl)phenyl]sulphoximide

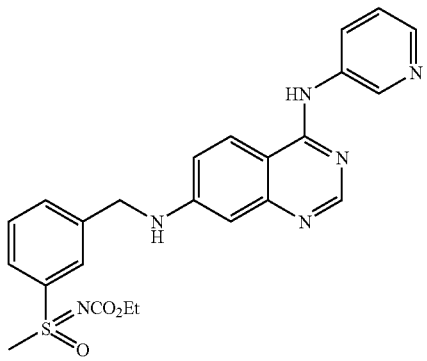

According to GWP 5, the reaction of N'-(2-cyano-5-{3-[(RS)-N-(ethoxycarbonyl)-S-methylsulphonimidoyl]benzylamino}phenyl)-N,N-dimethylformimidamide (50 mg, 0.12 mmol) with 3-aminopyridine (14 mg, 0.14 mmol) and chromatographic purification (silica gel, dichloromethane/methanol: 0→30% methanol) gives the desired product in 68% yield (38 mg).

¹H-NMR (300 MHz, DMSO): ∂ 0.99 (t, 3H), 3.40 (s, 3H), 3.77-3.83 (m, 2H), 4.54 (d, 2H), 6.56 (d, 1H), 7.04 (dd, 1H), 7.30-7.34 (m, 2H), 7.63 (t, 1H), 7.73 (d, 1H), 7.80 (d, 1H), 7.96 (s, 1H), 8.17-8.24 (m, 3H), 8.32 (m, 1H), 8.91 (d, 1H), 9.48 (s, 1H)

Example 1.51

(RS)-S-Methyl-S-[3-({[4-(3-pyridylamino)quinazolin-7-yl]amino}methyl)phenyl]-sulphoximide

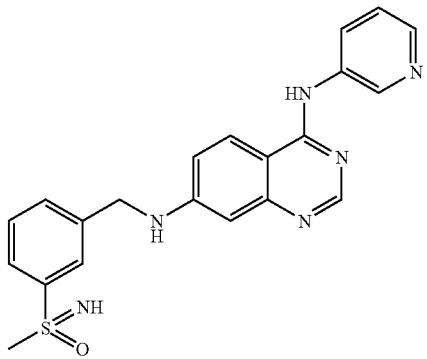

According to GWP 6, the conversion of (RS)-N-(ethoxycarbonyl)-S-methyl-S-[3-({[4-(3-pyridylamino)quinazolin-7-yl]amino}(methyl)phenyl]sulphoximide (35 mg, 0.073 mmol) and chromatographic purification (silica gel, dichloromethane/methanol: 0→30% methanol) gives the desired product in 81% yield (24 mg).

¹H-NMR (400 MHz, DMSO): ∂ 3.00 (s, 3H), 4.16 (s, 1H), 4.50 (d, 2H), 6.55 (d, 1H), 7.05 (dd, 1H), 7.31-7.35 (m, 2H), 7.54 (t, 1H), 7.63 (d, 1H), 7.78 (d, 1H), 7.95 (s, 1H), 8.17-8.25 (m, 3H), 8.32 (s, 1H), 8.91 (d, 1H), 9.49 (s, 1H).

Example 1.52

(RS)-S-[3-({[4-(Isopropylamino)quinazolin-7-yl]amino}methyl)phenyl]-S-methylsulphoximide

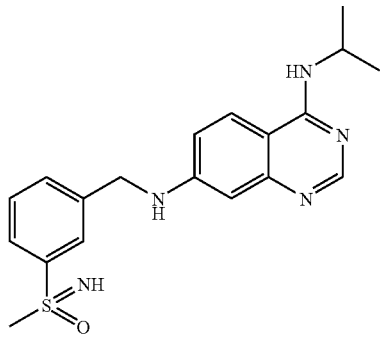

According to GWP 5, the reaction of N'-(2-cyano-5-{3-[(RS)-N-(ethoxycarbonyl)-S-methylsulphonimidoyl] benzylamino}phenyl)-N,N-dimethylformimidamide (130 mg, 0.3 mmol) with isopropylamine (0.031 mL, 0.36 mmol) and chromatographic purification (silica gel, dichloromethane/methanol: 7/3) gives 150 mg of product which is subsequently reacted with sodium ethoxide (104 mg, 1.7 mmol) according to GWP 6.

Chromatographic purification (silica gel, dichloromethane/methanol: 0→20% methanol) gives via 2 stages the desired product in 37% yield (49 mg).

¹H-NMR (300 MHz, DMSO): ∂ 1.21 (d, 6H), 3.04 (s, 3H), 4.19 (s, 1H), 4.42-4.51 (m, 3H), 6.46 (d, 1H), 6.91 (dd, 1H), 7.13 (t, 1H), 7.42 (d, 1H), 7.57 (t, 1H), 7.65 (d, 1H), 7.81 (d, 1H), 7.96-7.99 (m, 2H), 8.20 (s, 1H).

Example 1.53

(RS)-S-Methyl-S-[3-({[4-(1,3,4-thiadiazol-2-ylamino)quinazolin-7-yl]amino}-methyl)phenyl] sulphoximide

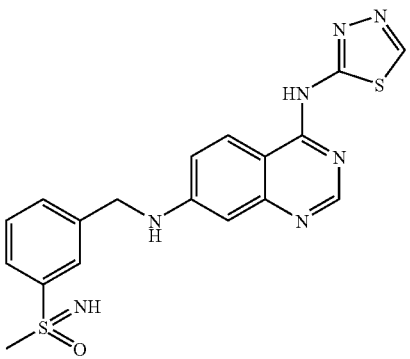

According to GWP 5, the reaction of N'-(2-cyano-5-{3-[(RS)-N-(ethoxycarbonyl)-S-methylsulphonimidoyl] benzylamino}phenyl)-N,N-dimethylformimidamide (100 mg, 0.23 mmol) with 2-amino-1,3,4-thiadiazole (29 mg, 0.28 mmol) and chromatographic purification (silica gel, n-hexane/ethyl acetate: 0→100% ethyl acetate, followed by dichloromethane/methanol: 0→20% methanol) gives 54 mg of product which is subsequently reacted with sodium ethoxide (34 mg, 0.56 mmol) according to GWP 6. Chromatographic purification (silica gel, n-hexane/ethyl acetate: 0→100% ethyl acetate, followed by dichloromethane/methanol: 0→25% methanol) gives via 2 stages the desired product in 23% yield (22 mg).

¹H-NMR (400 MHz, DMSO): ∂ 3.05 (s, 3H), 4.20 (s, 1H), 4.56 (d, 2H), 6.63 (d, 1H), 7.10 (dd, 1H), 7.53 (t, 1H), 7.59 (t, 1H), 7.68 (d, 1H), 7.84 (d, 1H), 7.99 (s, 1H), 8.38 (br, 1H), 8.53 (s, 1H), 9.13 (s, 1H), 12.36 (br, 1H).

Example 1.54

(RS)-N-(Ethoxycarbonyl)-S-methyl-S-[3-({[4-(thiazol-2-ylamino)quinazolin-7-yl]-amino}methyl)phenyl]sulphoximide

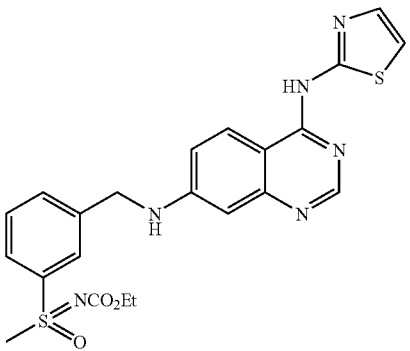

According to GWP 5, the reaction of N'-(2-cyano-5-{3-[(RS)-N-(ethoxycarbonyl)-S-methylsulphonimidoyl] benzylamino}phenyl)-N,N-dimethylformimidamide (90 mg, 0.21 mmol) with 2-aminothiazole (26 mg, 0.25 mmol) and chromatographic purification (silica gel, dichloromethane/methanol: 0→30% methanol) gives the desired product in 43% yield (43 mg).

$^1$H-NMR (300 MHz, DMSO): ∂ 0.97 (t, 3H), 3.40 (s, 3H), 3.74-3.85 (m, 2H), 4.54 (d, 2H), 6.60 (d, 1H), 7.03 (dd, 1H), 7.17 (s, 1H), 7.41 (t, 1H), 7.47 (d, 1H), 7.62 (t, 1H), 7.72 (d, 1H), 7.80 (d, 1H), 7.95 (s, 1H), 8.35-8.48 (br, 2H), 11.71 (br, 1H).

Example 1.55

(RS)-S-Methyl-S-[3-({[4-(thiazol-2-ylamino)quinazolin-7-yl]amino}methyl)-phenyl]sulphoximide

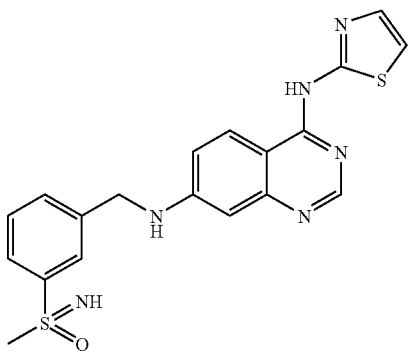

According to GWP 6, the conversion of (RS)-N-(ethoxycarbonyl)-S-methyl-S-[3-({[4-(thiazol-2-ylamino)quinazolin-7-yl]amino}methyl)phenyl]sulphoximide (40 mg, 0.083 mmol) and chromatographic purification (silica gel, dichloromethane/methanol: 0→20% methanol) gives the desired product in 77% yield (26 mg).

$^1$H-NMR (300 MHz, DMSO): ∂ 3.05 (s, 3H), 4.20 (s, 1H), 4.56 (d, 2H), 6.64 (d, 1H), 7.08 (dd, 1H), 7.22 (br, 1H), 7.45 (t, 1H), 7.52 (d, 1H), 7.59 (t, 1H), 7.68 (d, 1H), 7.99 (s, 1H), 8.40-8.53 (br, 2H), 11.81 (br, 1H).

Example 1.56

(RS)-S-[3-({[6-Bromo-4-(isopropylamino)quinazolin-7-yl]amino}methyl)phenyl]-N-(ethoxycarbonyl)-S-methylsulphoximide

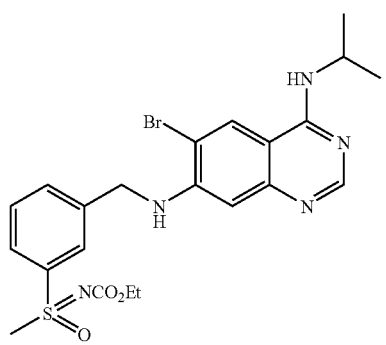

1.56. a) Preparation of the Intermediates

Compound 1.56. a.1

2-Amino-5-bromo-4-nitrobenzonitrile

2-Amino-4-nitrobenzonitrile (1.6 g, 9.81 mmol) is presented as an initial charge in 30 mL of dioxane and is mixed at 10° C. with bromine (0.56 mL, 11 mmol). This is followed by stirring at 60° C. for 6 hours. After cooling to room temperature, the batch is added to dilute sodium thiosulphate solution. After extraction of dichloromethane, the combined organic phases are dried over sodium sulphate to leave, after removal of the solvent and chromatographic purification (silica gel, n-hexane/ethyl acetate: 0→100% ethyl acetate), the product in 36% yield (820 mg).

$^1$H-NMR (400 MHz, DMSO): ∂ 6.85 (s, 2H), 7.27 (s, 1H), 7.98 (s, 1H)

Compound 1.56. a.2

N'-(4-Bromo-2-cyano-5-nitrophenyl)-N,N-dimethylformimidamide

2-Amino-5-bromo-4-nitrobenzonitrile (815 mg, 3.37 mmol) is admixed with N,N-dimethylformamide dimethyl acetal (1.65 mL, 12.5 mmol). After 20 minutes in an ultrasonic bath, excess N,N-dimethylformamide dimethyl acetal is removed on a rotary evaporator to leave, after chromatographic purification of the residue (silica gel, n-hexane/ethyl acetate: 0→60% ethyl acetate) the product in 86% yield (863 mg).

$^1$H-NMR (400 MHz, DMSO): ∂ 2.99 (s, 3H), 3.07 (s, 3H), 7.83 (s, 1H), 8.14 (s, 1H), 8.16 (s, 1H).

Compound 1.56. a.3

N'-(5-Amino-4-bromo-2-cyanophenyl)-N,N-dimethylformimidamide

N'-(4-Bromo-2-cyano-5-nitrophenyl)-N,N-dimethylformimidamide (1.1 g, 3.7 mmol) is dissolved in 500 mL of tetrahydrofuran, cooled to 0° C. and admixed with titanium trichloride solution (51 mL of a 15% solution in 10% aqueous HCl). This is followed by stirring at room temperature for 4 hours. The batch is adjusted to pH 9 at 0° C. by means of 2N aqueous sodium hydroxide solution. The mixture is diluted with water and ethyl acetate. The aqueous phase is saturated with sodium chloride and stirred out three times with ethyl acetate. The combined organic phases are dried over sodium sulphate to leave, after removal of the solvent and also chromatographic purification (silica gel, n-hexane/ethyl acetate: 0→100% ethyl acetate, ethyl acetate/methanol 9/1), the desired product in 60% yield (590 mg)

$^1$H-NMR (300 MHz, DMSO): ∂ 2.89 (s, 3H), 2.99 (s, 3H), 5.93 (s, 2H), 6.27 (s, 1H), 7.52 (s, 1H), 7.68 (s, 1H).

1.56. b) Preparation of the Final Product

N'-(5-Amino-4-bromo-2-cyanophenyl)-N,N-dimethylformimidamide (580 mg, 2.17 mmol) is dissolved in 15 mL of dimethylformamide and admixed with potassium carbonate (556 mg, 4.02 mmol) and also (RS)-S-[3-(bromomethyl)phenyl]-N-(ethoxy-carbonyl)-S-methylsulphoximide (696 mg, 2.17 mmol). This is followed by 9 hours' stirring at 110° C. After cooling to room temperature, the reaction solution is diluted with ethyl acetate and the organic phase is washed with water. Drying of the organic phase over sodium sulphate, concentrating the solvent and chromatography (silica gel, dichloromethane/methanol: 0→10% methanol) leaves 113 mg of product which is reacted with isopropylamine (0.023 mL, 0.27 mmol) according to GWP 5. Preparative thin layer chromatography gives the desired product via 2 stages in 6% yield (63 mg).

$^1$H-NMR (300 MHz, DMSO): ∂ 0.96 (t, 3H), 1.17 (d, 6H), 3.39 (s, 3H), 3.74-3.81 (m, 2H), 4.33-4.40 (m, 1H), 4.59 (d, 2H), 6.45 (s, 1H), 6.77 (t, 1H), 7.57-7.69 (m, 3H), 7.78 (d, 1H), 7.94 (s, 1H), 8.17 (s, 1H), 8.49 (s, 1H).

Example 1.57

(RS)-S-[3-({[6-Bromo-4-(isopropylamino)quinazolin-7-yl]amino}methyl)phenyl]-S-methylsulphoximide

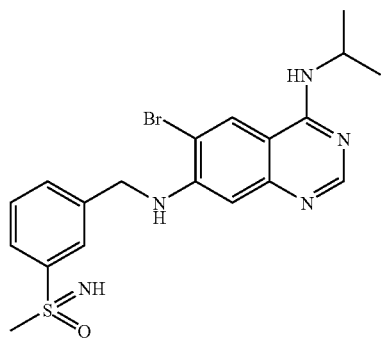

According to GWP 6, the conversion of (RS)-S-[3-({[6-bromo-4-(isopropylamino)-quinazolin-7-yl]amino}methyl)phenyl]-N-(ethoxycarbonyl)-S-methylsulphoximide (49 mg, 0.094 mmol) and preparative thin layer chromatography (silica gel, dichloromethane/methanol 9/1) gives the desired product in 85% yield (36 mg).

$^1$H-NMR (300 MHz, DMSO): ∂ 1.17 (d, 6H), 2.99 (s, 3H), 4.15 (s, 1H), 4.33-4.40 (m, 1H), 4.57 (d, 1H), 6.44 (s, 1H), 6.74 (t, 1H), 7.49-7.63 (m, 3H), 7.76 (d, 1H), 7.93 (s, 1H), 8.16 (s, 1H), 8.49 (s, 1H).

Example 1.58

(RS)-N-(Ethoxycarbonyl)-S-methyl-S-[3-({[4-(2-methyl-5-pyridylamino)-6-methoxyquinazolin-7-yl]oxy}methyl)phenyl]sulphoximide

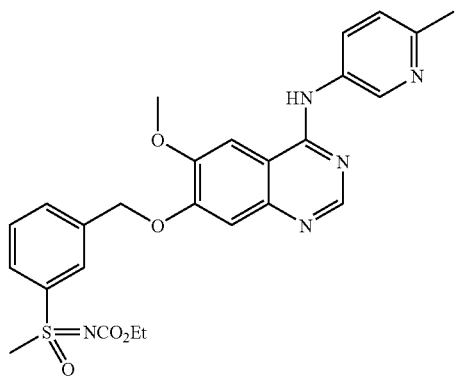

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (100 mg, 0.22 mmol) with 5-amino-2-methylpyridine (28 mg, 0.26 mmol) and chromatography (silica gel, dichloromethane/methanol: 4/1) gives the desired product in 36% yield (40 mg).

$^1$H-NMR (300 MHz, DMSO): ∂ 1.08 (t, 3H), 2.48 (s, 3H), 3.50 (s, 3H), 3.85-3.93 (m, 2H), 3.99 (s, 3H), 5.44 (s, 2H), 7.29 (d, 1H), 7.36 (s, 1H), 7.76 (t, 1H), 7.89-7.91 (m, 2H), 7.97 (d, 1H), 8.10-8.14 (m, 2H), 8.46 (s, 1H), 8.78 (d, 1H), 9.60 (s, 1H).

Example 1.59

(RS)-S-[3-({[4-(2-Methyl-5-pyridylamino)-6-methoxyquinazolin-7-yl]oxy}methyl)-phenyl]-S-methylsulphoximide

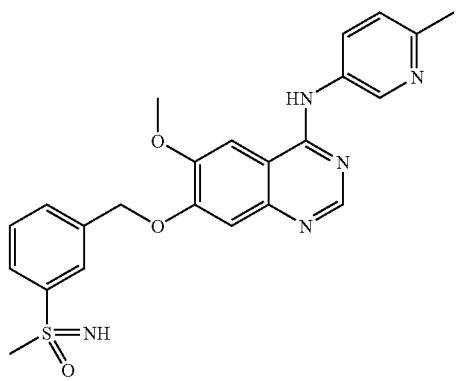

According to GWP 6, the conversion of (RS)-N-(ethoxycarbonyl)-S-methyl-S-[3-({[4-(2-methyl-5-pyridylamino)-6-methoxyquinazolin-7-yl]oxy}methyl)phenyl]-sulphoximide (33 mg, 0.063 mmol) and chromatography (silica gel, dichloromethane/methanol 4/1) gives the desired product in 83% yield (24 mg).

¹H-NMR (300 MHz, DMSO): ∂ 2.48 (s, 3H), 3.10 (s, 3H), 3.99 (s, 3H), 4.30 (s, 1H), 5.41 (s, 2H), 7.29 (d, 1H), 7.35 (s, 1H), 7.68 (t, 1H), 7.80 (d, H), 7.89 (s, 1H), 7.95 (d, 1H), 8.12 (dd, 1H), 8.46 (s, 1H), 8.78 (d, 1H), 9.60 (s, 1H).

Example 1.60

(RS)-S-{3-[({4-[(3-Cyanophenyl)amino]-6-methoxyquinazolin-7-yl}oxy)methyl]-phenyl}-N-(ethoxycarbonyl)-S-methylsulphoximide

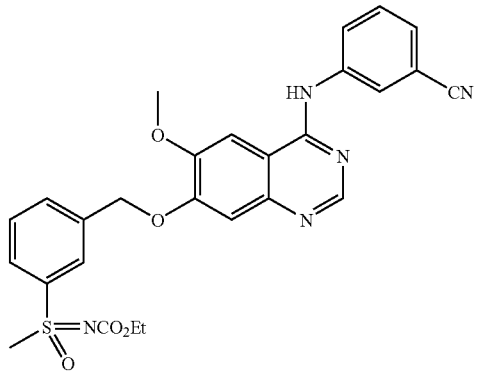

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (100 mg, 0.22 mmol) with 3-aminobenzonitrile (31 mg, 0.26 mmol) and chromatography (silica gel, dichloromethane/methanol: 4/1) gives the desired product in 71% yield (82 mg).

¹H-NMR (300 MHz, DMSO): ∂ 1.08 (t, 3H), 3.50 (s, 3H), 3.85-3.92 (m, 2H), 4.00 (s, 3H), 5.45 (s, 2H), 7.55-7.65 (m, 2H), 7.76 (t, 1H), 7.90-7.92 (m, 2H), 7.98 (d, 1H), 8.13-8.17 (m, 2H), 8.38 (s, 1H), 8.56 (s, 1H), 9.73 (s, 1H).

Example 1.61

(RS)-S-{3-[({4-[(3-Cyanophenyl)amino]-6-methoxyquinazolin-7-yl}oxy)methyl]-phenyl}-S-methylsulphoximide

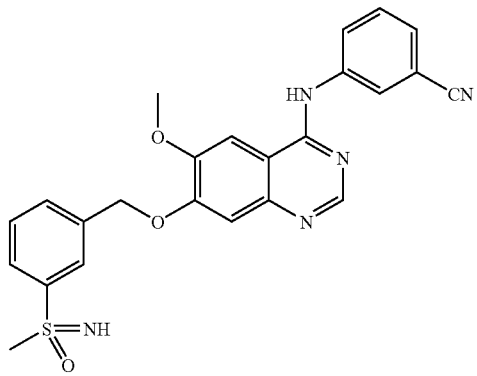

According to GWP 6, the conversion of (RS)-S-{3-[({4-[(3-cyanophenyl)amino]-6-methoxyquinazolin-7-yl}oxy)methyl]phenyl}-N-(ethoxycarbonyl)-S-methyl-sulphoximide (70 mg, 0.13 mmol) and chromatography (silica gel, dichloromethane/methanol 4/1) gives the desired product in 79% yield (48 mg).

¹H-NMR (400 MHz, DMSO): ∂ 3.05 (s, 3H), 3.96 (s, 3H), 4.25 (s, 1H), 5.38 (s, 2H), 7.34 (s, 1H), 7.51-7.65 (m, 3H), 7.75 (d, 1H), 7.84 (s, 1H), 7.90 (d, 1H), 8.06 (s, 1H), 8.11 (d, 1H), 8.34 (s, 1H), 8.52 (s, 1H), 9.68 (s, 1H).

Example 1.62

(RS)-N-(Ethoxycarbonyl)-S-methyl-S-[3-({[4-(2-methyl-4-pyridylamino)-6-methoxyquinazolin-7-yl]oxy}methyl)phenyl]sulphoximide

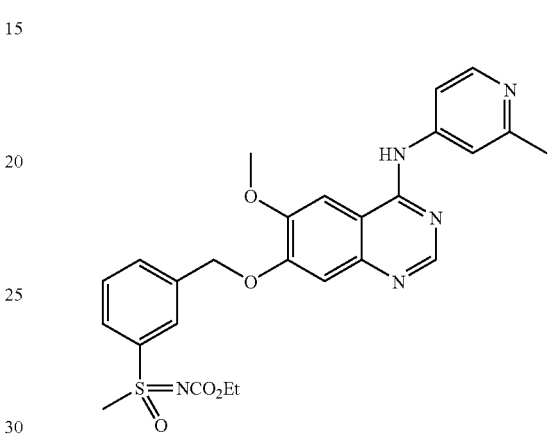

According to GWP 5, the reaction of N'-(2-cyano-5-{3-[(RS)-N-(ethoxycarbonyl)-S-methylsulphonimidoyl]benzyloxy}-4-methoxyphenyl)-N,N-dimethylformimidamide (100 mg, 0.22 mmol) with 4-amino-2-methylpyridine (28 mg, 0.26 mmol) and chromatography (silica gel, dichloromethane/methanol: 4/1) gives the desired product in 19% yield (21 mg).

¹H-NMR (400 MHz, DMSO): ∂ 1.03 (t, 3H), 2.43 (s, 3H), 3.45 (s, 3H), 3.81-3.88 (m, 2H), 3.97 (s, 3H), 5.41 (s, 2H), 7.37 (s, 1H), 7.70-7.79 (m, 3H), 7.85-7.87 (m, 2H), 7.92 (d, 1H), 8.09 (s, 1H), 8.32 (d, 1H), 8.59 (s, 1H), 9.61 (s, 1H).

Example 1.63

(RS)-S-[3-({[4-(2-Methyl-4-pyridylamino)-6-methoxyquinazolin-7-yl]oxy}methyl)-phenyl]-S-methylsulphoximide

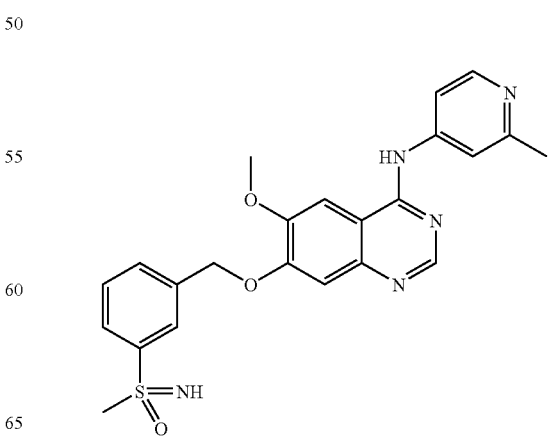

According to GWP 6, conversion of (RS)-N-(ethoxycarbonyl)-S-methyl-S-[3-({[4-(2-methyl-4-pyridylamino)-6-methoxyquinazolin-7-yl]oxy}methyl)phenyl]-sulphoximide (20 mg, 0.038 mmol) and chromatography (silica gel, dichloromethane/methanol 4/1) gives the desired product in 79% yield (14 mg).

¹H-NMR (400 MHz, DMSO): ∂ 2,43 (s, 3H), 3.05 (s, 3H), 3.96 (s, 3H), 4.25 (s, 1H), 5.38 (s, 2H), 7.36 (s, 1H), 7.64 (t, 3H), 7.75-7.79 (m, 3H), 7.87 (s, 1H), 7.90 (d, 1H), 8.06 (s, 1H), 8.31 (d, 1H), 8.59 (s, 1H), 9.63 (s, 1H).

Example 1.64

N-{2-[(6-Bromo-7-{3-[(RS)-N-(ethoxycarbonyl)-S-methylsulphonimidoyl]-benzyloxy}quinazolin-4-yl)amino]ethyl}acetamide

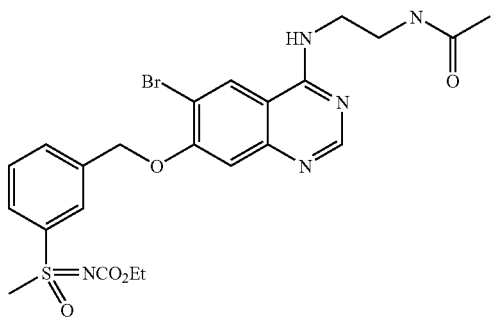

According to GWP 5, (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (70 mg, 0.14 mmol) is reacted with N-(2-aminoethyl)acetamide (0.02 mL mg, 0.17 mmol). The reaction solution is admixed with dilute sodium bicarbonate solution and the resulting crystals are filtered off with suction to obtain the desired product in 76% yield (59 mg).

¹H-NMR (300 MHz, DMSO): ∂ 1.02 (t, 3H), 1.77 (s, 3H), 3.25-3.29 (m, 2H+water), 3.44 (s, 3H), 3.48-3.54 (m, 2H), 3.80-3.91 (m, 2H), 5.46 (s, 2H), 7.31 (s, 1H), 7.72 (t, 1H), 7.85 (d, 1H), 7.91 (d, 1H), 7.98 (t, 1H), 8.10 (s, 1H), 8.31 (t, 1H), 8.40 (s, 1H), 8.56 (s, 1H).

Example 1.65

N-{2-[(6-Bromo-7-{3-[(RS)-S-methylsulphonimidoyl]benzyloxy}quinazolin-4-yl)-amino]ethyl}acetamide

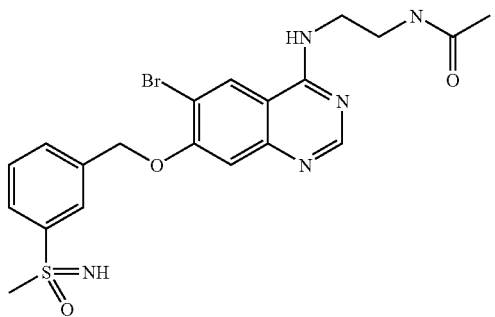

According to GWP 6, the conversion of N-{2-[(6-bromo-7-{3-[(RS)-N-(ethoxy-carbonyl)-S-methylsulphonimidoyl]benzyloxy}quinazolin-4-yl)amino]ethyl}acetamide (86 mg, 0.15 mmol) and chromatography (silica gel, dichloromethane/methanol: 0→10% methanol) gives the desired product in 45% yield (33 mg).

¹H-NMR (300 MHz, DMSO): ∂ 1.77 (s, 3H), 3.04 (s, 3H), 3.23-3.29 (m, 2H+water), 3.47-3.54 (m, 2H), 4.24 (s, 1H), 5.43 (s, 2H), 7.30 (s, 1H), 7.63 (t, 1H), 7.76 (d, 1H), 7.89 (d, 1H), 7.98 (t, 1H), 8.07 (s, 1H), 8.30 (t, 1H), 8.39 (s, 1H), 8.56 (s, 1H).

Example 1.66

(RS)-S-[3-({[6-Bromo-4-(ethylamino)quinazolin-7-yl]oxy}methyl)phenyl]-N-(ethoxycarbonyl)-S-methylsulphoximide

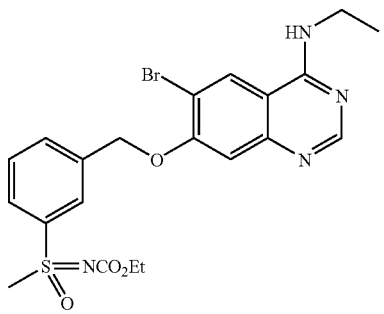

According to GWP 5, the reaction of (E/Z)-N'-(4-bromo-2-cyano-5-{3-[(RS)-N-(ethoxy-carbonyl)-S-methylsulphonimidoyl]benzyloxy}phenyl)-N,N-dimethylformimidamide (70 mg, 0.14 mmol) with ethylamine (0.08 mL mg, 0.17 mmol) and thin layer chromatography (silica gel, dichloromethane/methanol: 9/1) gives the desired product in 71% yield (50 mg)

¹H-NMR (300 MHz, DMSO): ∂ 1.02 (t, 3H), 1.18 (t, 3H), 3.44 (s, 3H), 3.47-3.53 (m, 2H), 3.80-3.91 (m, 2H), 5.45 (s, 2H)7.29 (s, 1H), 7.72 (t, 1H), 7.85 (d, 2H), 7.91 (d, 1H), 8.11 (s, 1H), 8.19 (t, 1H), 8.39 (s, 1H), 8.59 (s, 1H).

Example 1.67

(RS)-S-[3-({[6-Bromo-4-(ethylamino)quinazolin-7-yl]oxy}methyl)phenyl]-S-methylsulphoximide

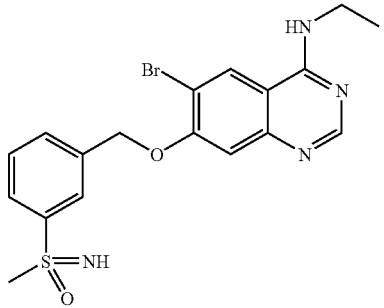

According to GWP 6, (RS)-S-[3-({[6-bromo-4-(ethylamino)quinazolin-7-yl]oxy}methyl)-phenyl]-N-(ethoxycarbonyl)-S-methylsulphoximide (38 mg, 0.075 mmol) is dissolved in ethanol (5 mL), admixed with sodium ethoxide (19 mg, 0.27 mmol) and stirred at 60° C. for 3 hours. The reaction solution is admixed with saturated sodium bicarbonate solution and extracted with ethyl acetate. After drying of the organic phase over sodium sulphate and removal of the solvent, the residue is subsequently stirred up with methanol and the crystals are filtered off with suction to obtain the desired product in 45% yield (33 mg).

¹H-NMR (400 MHz, DMSO): ∂ 1.18 (s, 3H), 3.04 (s, 3H), 3.46-3.52 (m, 2H), 4.23 (s, 1H), 5.43 (s, 2H), 7.29 (s, 1H), 7.64 (t, 1H), 7.76 (d, 1H), 7.88 (d, 1H), 8.08 (s, 1H), 8.19 (t, 1H), 8.38 (s, 1H), 8.58 (s, 1H).

Example 1.68

(RS)-S-{3-[({6-Bromo-4-[(3-hydroxy-2,2-dimethyl-propyl)amino]quinazolin-7-yl}-oxy)methyl]phenyl}-S-methylsulphoximide

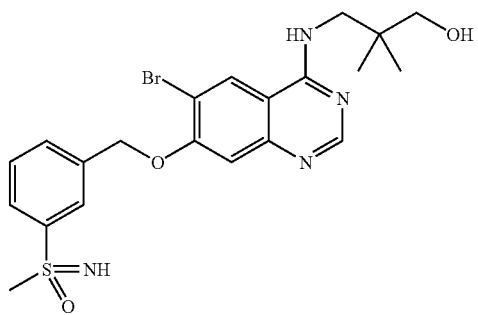

According to GWP 5, (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (75 mg, 0.15 mmol) is reacted with 3-amino-2,2-dimethyl-1-propanol (18 mg, 0.18 mmol). After the reaction has ended, the reaction solution is diluted with dilute sodium bicarbonate solution and subsequently extracted with ethyl acetate. Drying of the organic phase over sodium sulphate, removal of the solvent and chromatographic purification of the residue (silica gel, dichloromethane/methanol: 0→10% methanol) gives 67 mg of product which is subsequently reacted with sodium ethoxide (29 mg, 0.41 mmol) according to GWP 6. Chromatographic purification (silica gel, dichloromethane/methanol: 0→10% methanol) gives via 2 stages the desired product in 35% yield (26 mg).

¹H-NMR (300 MHz, DMSO): ∂ 0.80 (s, 6H), 3.04 (s, 3H), 3.10 (d, 2H), 3,86 (s, 2H), 4.24 (s, 1H), 4.81 (t, 1H), 5.46 (s, 2H), 7.35 (s, 1H), 7.64 (t, 1H), 7.75 (d, 1H), 7.89 (d, 1H), 8.07 (s, 1H), 8.24-8.26 (m, 2H).

Example 1.69

(RS)-S-(3-{[(6-Bromo-4-{[(RS)-2-hydroxy-1-methylethyl]amino}quinazolin-7-yl)-oxy]methyl}phenyl)-S-methylsulphoximide

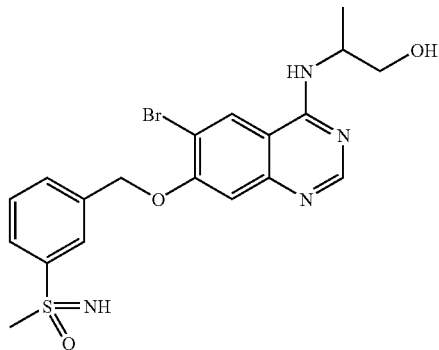

According to GWP 5, (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (250 mg, 0.49 mmol) is reacted with alaninol (0.05 mL, 0.59 mmol). After the reaction has ended, the reaction solution is diluted with dilute sodium bicarbonate solution and subsequently extracted with ethyl acetate. Drying of the organic phase over sodium sulphate, removal of the solvent and chromatographic purification of the residue (silica gel, dichloromethane/methanol: 0→10% methanol) leaves 146 mg of product which is subsequently reacted with sodium ethoxide (67 mg, 0.98 mmol) according to GWP 6. Chromatographic purification (silica gel, dichloromethane/methanol: 0→10% methanol) gives via 2 stages the desired product in 26% yield (59 mg).

¹H-NMR (400 MHz, DMSO): ∂ 1.35 (d, 3H), 3.04 (s, 3H), 3.55-3.62 (m, 1H), 3.67-3.75 (m, 1H), 4.23 (s, 1H), 4.76-4.82 (m, 1H), 4.99 (t, 1H), 5.46 (s, 2H), 7.35 (s, 1H), 7.63 (t, 1H), 7.75 (d, 1H), 7.88 (d, 1H), 8.08 (s, 1H), 8.24 (s, 1H), 8.35 (s, 1H).

Example 1.70

(RS)-S-(3-{[(6-Bromo-4-{[(S)-2-hydroxypropyl]amino}quinazolin-7-yl)oxy]-methyl}phenyl)-N-(ethoxycarbonyl)-S-methylsulphoximide

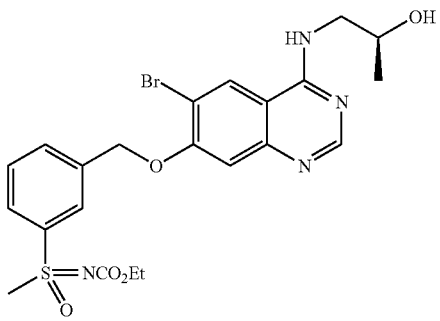

According to GWP 5, (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (80 mg, 0.16 mmol) is reacted with (S)-1-amino-2-propanol (14 mg, 0.19 mmol). After the reaction has ended, the reaction solution is diluted with dilute sodium bicarbonate solution and the resulting precipitate is filtered off with suction. Chromatographic purification of the residue (silica gel, dichloromethane/methanol: 0→10% methanol) gives the desired product in 58% yield (49 mg).

¹H-NMR (400 MHz, DMSO): ∂ 1.06 (t, 3H), 1.10 (d, 3H), 3.37-3.50 (m, 5H), 3.84-3.94 (m, 3H), 4.84 (d, 1H), 5.50 (s, 2H), 7.34 (s, 1H), 7.76 (t, 1H), 7.90 (d, 1H), 7.95 (d, 1H), 8.15 (s, 1H), 8.29 (t, 1H), 8.42 (s, 1H), 8.70 (s, 1H).

Example 1.71

(RS)-S-(3-{[(6-Bromo-4-{[(S)-2-hydroxypropyl]
amino}quinazolin-7-yl)oxy]-methyl}phenyl)-S-methylsulphoximide

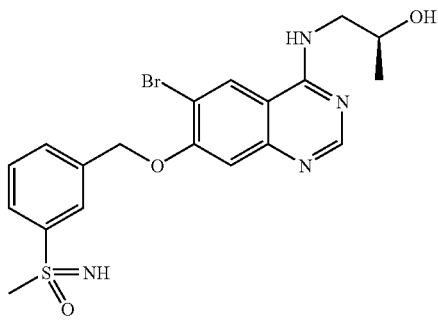

According to GWP 6, (RS)-S-(3-{[(6-bromo-4-{[(S)-2-hydroxypropyl]amino}quinazolin-7-yl)oxy]methyl}phenyl)-N-(ethoxycarbonyl)-S-methylsulphoximide (39 mg, 0.073 mmol) is dissolved in ethanol (5 mL), admixed with sodium ethoxide (18 mg, 0.26 mmol) and stirred at 60° C. for 6 hours. The reaction solution is admixed with saturated sodium bicarbonate solution and extracted with ethyl acetate. Drying of the organic phase over sodium sulphate and removal of the solvent and also chromatographic purification of the residue (silica gel, dichloromethane/methanol: 0→10% methanol) gives the desired product in 86% yield (29 mg).

$^1$H-NMR (400 MHz, DMSO): ∂ 1.06 (d, 3H), 3.04 (s, 3H), 3.38-3.45 (m, 2H), 3.89 (br, 1H), 4.25 (br, 1H), 4.79 (d, 1H), 5.43 (s, 2H), 7.29 (s, 1H), 7.64 (t, 1H), 7.76 (d, 1H), 7.88 (d, 1H), 8.08 (s, 1H), 8.24 (t, 1H), 8.37 (s, 1H), 8.65 (s, 1H).

Example 1.72

(RS)-S-(3-{[(6-Bromo-4-{[(R)-2-hydroxypropyl]
amino}quinazolin-7-yl)oxy]-methyl}-phenyl)-N-
(ethoxycarbonyl)-S-methylsulphoximide

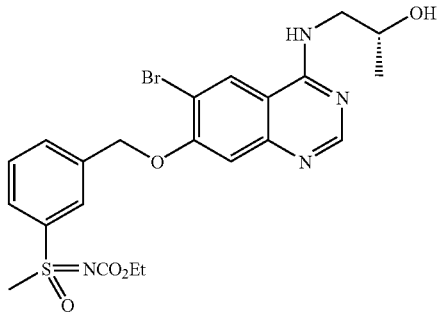

According to GWP 5, (E/Z)-N'-(4-bromo-2-cyano-5-{3-[(RS)-N-(ethoxycarbonyl)-S-methylsulphonimidoyl]benzyloxy}phenyl)-N,N-dimethylformimidamide (80 mg, 0.16 mmol) is reacted with (R)-1-amino-2-propanol (14 mg, 0.19 mmol). After the reaction has ended, the reaction solution is diluted with dilute sodium bicarbonate solution and the resulting precipitate is filtered off with suction. Chromatographic purification of the precipitate (silica gel, dichloromethane/methanol: 0→10% methanol) gives the desired product in 58% yield (49 mg).

$^1$H-NMR (400 MHz, DMSO): ∂ 1.06 (t, 3H), 1.10 (d, 3H), 3.39-3.50 (m, 5H), 3.84-3.94 (m, 3H), 4.84 (d, 1H), 5.50 (s, 2H), 7.34 (s, 1H), 7.76 (t, 1H), 7.89 (d, 1H), 7.95 (d, 1H), 8.15 (s, 1H), 8.29 (t, 1H), 8.42 (s, 1H), 8.70 (s, 1H).

Example 1.73

(RS)-S-(3-{[(6-Bromo-4-{[(R)-2-hydroxypropyl]
amino}quinazolin-7-yl)oxy]-methyl}phenyl)-S-methylsulphoximide

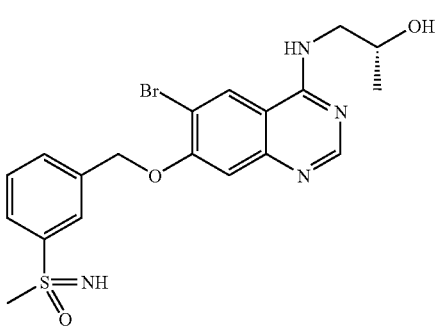

According to GWP 6, (RS)-S-(3-{[(6-bromo-4-{[(R)-2-hydroxypropyl]amino}quinazolin-7-yl)oxy]methyl}phenyl)-N-(ethoxycarbonyl)-S-methylsulphoximide (38 mg, 0.071 mmol) is dissolved in ethanol (5 mL), admixed with sodium ethoxide (17 mg, 0.25 mmol) and stirred at 60° C. for 6 hours. The reaction solution is admixed with saturated sodium bicarbonate solution and extracted with ethyl acetate. Drying of the organic phase over sodium sulphate and removal of the solvent and also chromatographic purification of the residue (silica gel, dichloromethane/methanol: 0→10% methanol) gives the desired product in 88% yield (29 mg).

$^1$H-NMR (400 MHz, DMSO): ∂ 1.06 (d, 3H), 3.04 (s, 3H), 3.36-3.48 (m, 2H), 3.89 (br, 1H), 4.25 (br, 1H), 4.79 (d, 1H), 5.43 (s, 2H), 7.29 (s, 1H), 7.64 (t, 1H), 7.76 (d, 1H), 7.89 (d, 1H), 8.08 (s, 1H), 8.24 (t, 1H), 8.37 (s, 1H), 8.65 (s, 1H).

2. Process Variant 2

Example 2.1

(RS)-N-(Ethoxycarbonyl)-S-[3-({[4-(isopropylamino)quinazolin-7-yl]oxy}methyl)-phenyl]-S-methylsulphoximide

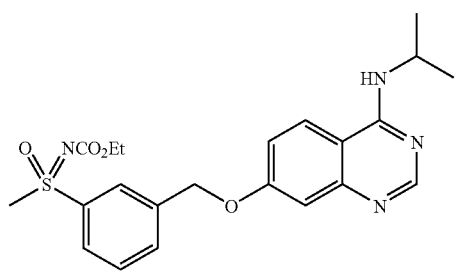

2.1. a) Preparation of the Intermediates

Compound 2.1. a.1

4-Amino-5-cyano-2-hydroxybenzoic acid

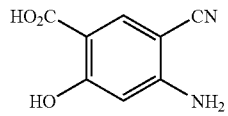

Ethyl 4-amino-5-cyano-2-hydroxybenzoate (3 g, 14.55 mmol) is treated with 60 ml of a 10% strength sodium hydroxide solution and the mixture is stirred at 50° C. for one hour. After cooling, the reaction solution is acidified with concentrated hydrochloric acid, diluted with water and the precipitate is filtered off with suction. The desired product is obtained after recrystallization from ethanol in 62% yield (1.6 g).

$^1$H-NMR (400 MHz, DMSO-d6): δ 6.17 (s, 1H), 6.73 (brs, 2H), 7.86 (s, 1H), 11.71 (br s, 1H), 13.62 (br s, 1H).

Compound 2.1 a.2

2-Amino-4-hydroxybenzonitrile

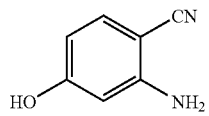

4-Amino-5-cyano-2-hydroxybenzoic acid (2.1 g, 11.79 mmol) is added to a quinoline solution already heated to 160° C. (12 ml) and the reaction solution is stirred at 180° C. for a further hour. After cooling, it is diluted with about 50 ml of a 1N sodium hydroxide solution. The mixture is extracted with dichloromethane. Subsequently, the aqueous phase is adjusted to pH 6.5 with hydrochloric acid and extracted with ethyl acetate and methanol (as a solubilizer). The combined organic phases are dried over sodium sulphate. The desired product is obtained after concentrating the solvents in 76% yield (1.2 g).

$^1$H-NMR (400 MHz, DMSO-d6): δ 5.81 (s, 2H), 6.04 (dd, 1H), 6.16 (d, 1H), 7.17 (d, 1H), 9.98 (s, 1H).

Compound 2.1. a.3

(E/Z)-N'-(2-Cyano-5-hydroxyphenyl)-N,N-dimethyl-formimidamide

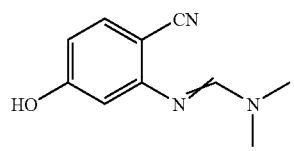

2-Amino-4-hydroxybenzonitrile (1.1 g, 8.2 mmol) and dimethylformamide dimethyl acetal (3.91 g, 33 mmol) are combined and stirred at room temperature for 2 hours. The reaction solution is concentrated. The desired product is obtained after chromatographic purification (silica gel, dichloromethane/methanol: 9/1) of the residue in 86% yield (1.4 g)

$^1$H-NMR (400 MHz, DMSO-d6): δ 2.95 (s, 3H), 3.05 (s, 3H), 6.41-6.46 (m, 2H), 7.38 (d, 1H), 7.82 (s, 1H), 10.17 (s, 1H).

Compound 2.1. a.4

4-(Isopropylamino)quinazolin-7-ol

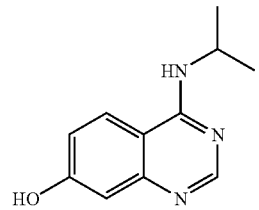

According to GWP 5, (E/Z)-N'-(2-cyano-5-hydroxyphenyl)-N,N-dimethylformimid-amide (1.4 g, 7.4 mmol) is reacted in 2 portions with isopropylamine (0.53 g, 8.88 mmol) in acetonitrile (14 ml) and acetic acid (7 ml). The reaction solution is concentrated and the residue is triturated with diethyl ether. The crystals are filtered off with suction and dried. The desired product is obtained in quantitative yield (2.1 g).

LC-MS (Instrument: Micromass Platform LCZ with HPLC Agilent Series 1100; column: Thermo Hypersil GOLD 3μ 20×4 mm; eluent A: 1 l of water+0.5 ml of 50% strength formic acid, eluent B: 1 l of acetonitrile+0.5 ml 50% of strength formic acid; gradient: 0.0 min 100% A→0.2 min 100% A→2.9 min 30% A→3.1 min 10% A→5.5 min 10% A; oven: 50° C.; flow: 0.8 ml/min; UV detection: 210 nm): $R_t$=2.16 min; MS (ESI pos.): m/z=204 (M+H$^+$).

2.1. b) Preparation of the Final Product 4-(Isopropylamino)quinazolin-7-ol (60 mg, 0.23 mmol) and (RS)-S-[3-(bromomethyl)-phenyl]-N-(ethoxycarbonyl)-S-methylsulphoximide (112 mg, 0.29 mmol) are suspended in 10 ml of acetone. After addition of caesium carbonate (264 mg, 0.81 mmol), the reaction mixture is refluxed for 4 hours. The batch is diluted with ethyl acetate, and the organic phase is washed with water and dried over sodium sulphate. The desired product is obtained after removing the solvent and after chromatographic purification (silica gel, dichloromethane/methanol: 9/1), in 62% yield (70 mg).

LC-MS (method: see Example 1.16): $R_t$=1.00 min; MS (ESI pos.): m/z=443 (M+H$^+$).

Example 2.2

(RS)-S-[3-({[4-(Isopropylamino)quinazolin-7-yl]oxy}methyl)phenyl]-S-methyl-sulphoximide

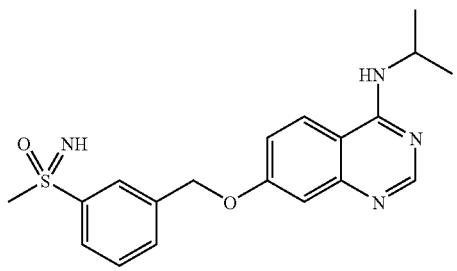

According to GWP 6, (RS)-N-(ethoxycarbonyl)-S-[3-({[4-(isopropylamino)quinazolin-7-yl]oxy}methyl)phenyl]-S-methylsulphoximide (68 mg, 0.16 mmol) is reacted with sodium ethoxide (46 mg, 0.68 mmol) at 80° C. for 2 hours. The reaction mixture is concentrated to dryness. The residue is taken up in ethyl acetate and water. The organic phase is separated off, dried over sodium sulphate and subsequently concentrated. The residue is triturated a number of times with diethyl ether and the solvent is subsequently decanted off. The residue is dissolved in dichloromethane and concentrated again. The desired product is obtained in 51% yield (30 mg).

$^1$H-NMR (400 MHz, DMSO-d6): δ 1.24 (d, 6H), 3.08 (s, 3H), 4.26 (s, 1H), 4.48 (dsept, 1H), 5.36 (s, 2H), 7.18 (d, 1H), 7.20 (dd, 1H), 7.65 (t, 1H), 7.74-7.79 (m, 2H), 7.91 (d, 1H), 8.08 (s, 1H), 8.25 (d, 1H), 8.38 (s, 1H).

Example 2.3

Ethyl 7-({(RS)-3-[N-(ethoxycarbonyl)-S-methylsulphonimidoyl]benzyl}oxy)-4-(thiazol-2-ylamino)quinazoline-6-carboxylate

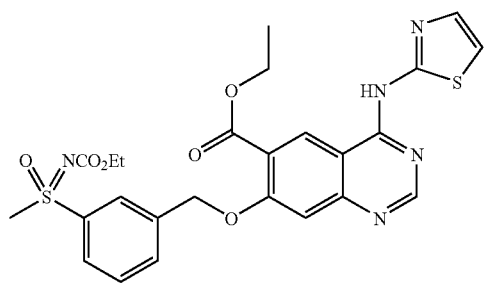

2.3. a) Preparation of the Intermediate

Ethyl 7-hydroxy-4-(thiazol-2-ylamino)quinazoline-6-carboxylate, acetate

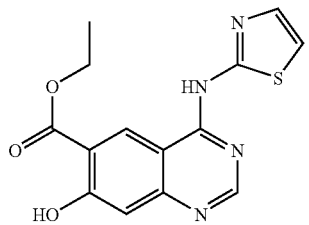

According to GWP 5, ethyl-5-cyano-4-{(E/Z)-[(dimethylamino)methylene]amino}-2-hydroxybenzoate (2.0 g, 7.7 mmol) is reacted with 2-aminothiazole (0.92 g, 9.18 mmol) in acetonitrile (10 ml) and acetic acid (5 ml). After cooling, the resulting crystals are stirred with diethyl ether, filtered off with suction and dried. The desired product is obtained in 73% yield (2.1 g) as the acetic acid salt.

LC-MS (method: see Example 1.16): $R_t$=1.08 min. MS (ESI pos.): m/z=317 (M+H$^+$).

2.3. b) Preparation of the Final Product

Ethyl 7-hydroxy-4-(thiazol-2-ylamino)quinazoline-6-carboxylate, acetate (80 mg, 0.213 mmol) and (RS)-S-[3-(bromomethyl)phenyl]-N-(ethoxycarbonyl)-S-methyl-sulphoximide (104 mg, 0.28 mmol) are suspended in 10 ml of acetone. After the addition of caesium carbonate (264 mg, 0.81 mmol), the reaction mixture is initially refluxed for 4 hours, N,N-dimethylformamide (3 ml) is added and it is stirred and refluxed for a further 3 hours. After cooling, the batch is concentrated, the residue is taken up in ethyl acetate and water, and the organic phase is separated off and dried over sodium sulphate. After removing the solvent, the residue (175 mg, 86% of theory) is employed in the next reaction without further purification.

LC-MS (apparatus type MS: Micromass ZQ; apparatus type HPLC: HP 1100 Series; UV DAD; column: Phenomenex Gemini 3µ 30 mm×3.00 mm; eluent A: 1 l of water+0.5 ml of 50% strength formic acid, eluent B: 1 l of acetonitrile+0.5 ml of 50% strength formic acid; gradient: 0.0 min 90% A→2.5 min 30% A→3.0 min 5% A→4.5 min 5% A; flow: 0.0 min 1 ml/min, 2.5 min/3.0 min/4.5 min. 2 ml/min; oven: 50° C.; UV detection: 210 nm): $R_t$=1.68 min; MS (ESI pos.): m/z=556 (M+H$^+$).

Example 2.4

Ethyl 7-{[(RS)-3-(S-methylsulphonimidoyl)benzyl]oxy}-4-(thiazol-2-ylamino)-quinazoline-6-carboxylate

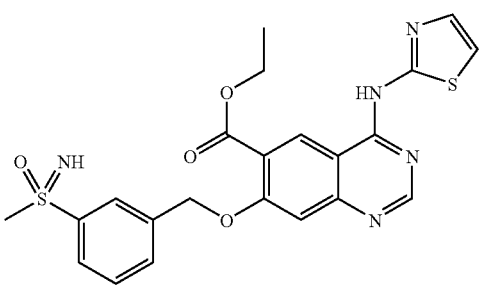

According to GWP 6, ethyl-7-({(RS)-3-[N-(ethoxycarbonyl)-S-methyl-sulphonimidoyl]-benzyl}oxy)-4-(thiazol-2-ylamino)quinazoline-6-carboxylate (175 mg, 0.182 mmol) is reacted at 80° C. for 2 hours with sodium ethoxide (55 mg, 0.8 mmol). After cooling, the reaction mixture is concentrated to dryness. The residue is taken up in ethyl acetate and water. The organic phase is separated off, dried over sodium sulphate and subsequently concentrated. The desired product is obtained after chromatographic purification (silica gel, dichloromethane/methanol: 9/1) in 42% yield (39 mg).

¹H-NMR (400 MHz, DMSO-d6): δ 1.38 (t, 3H), 2.99 (s, 3H), 4.18 (s, 1H), 4.43 (q, 2H), 5.57 (s, 2H), 7.13 (s, 1H), 7.18 (d, 1H), 7.61 (t, 1H), 7.80 (d, 1H), 7.87 (d, 2H), 8.01 (s, 1H), 8.76 (s, 1H), 9.02 (s, 1H), 10.86 (s, 1H).

LC-MS (method see Compound 1.16. a.3): $R_t$=1.19 min; MS (ESI pos.): m/z=473 (M+H⁺).

Example 2.5

(RS)-N-(Ethoxycarbonyl)-S-[3-({[4-(isopropylamino)-6-methoxyquinazolin-7-yl]oxy}methyl)phenyl]-S-methylsulphoximide

Example 2.6

(RS)-S-[3-({[4-(Isopropylamino)-6-methoxyquinazolin-7-yl]oxy}methyl)phenyl]-S-methylsulphoximide

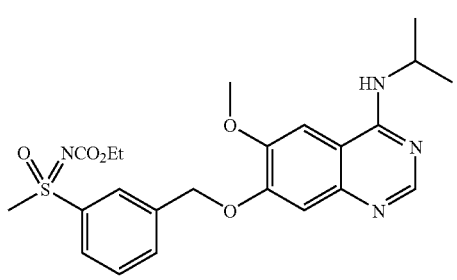

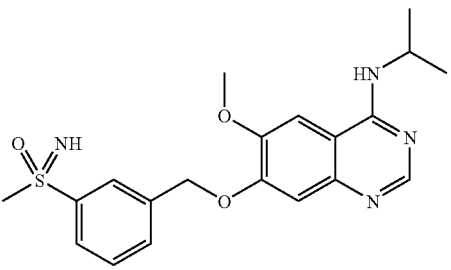

2.5. a) Preparation of the Intermediate 4-(Isopropylamino)-6-methoxyquinazolin-7-ol

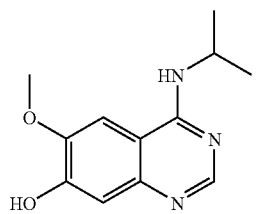

According to GWP 5, (E/Z)-N'-(2-cyano-5-hydroxy-4-methoxyphenyl)-N,N-dimethyl-formimidamide (0.62 g, 2.25 mmol) prepared according to WO2004/58752 is reacted with isopropylamine (0.16 g, 2.7 mmol) in acetonitrile (3 ml) and acetic acid (0.7 ml). After cooling, the batch is rendered alkaline by means of saturated sodium hydrogencarbonate solution and extracted with ethyl acetate. Concentrating the organic phase, the desired product is obtained in 55% yield (310 mg) as the acetic acid salt.

¹H-NMR (400 MHz, DMSO-d6): δ 1.26 (d, 6H), 3.91 (s, 3H), 4.49 (dsept, 1H), 6.94 (s, 1H), 7.45 (d, 1H), 7.59 (s, 1H), 8.25 (s, 1H), 10.08 (br s, 1H).

2.5. b) Preparation of the Final Product 4-(Isopropylamino)-6-methoxyquinazolin-7-ol (65 mg, 0.21 mmol) and (RS)-S-[3-(bromomethyl)phenyl]-N-(ethoxycarbonyl)-S-methylsulphoximide (102 mg, 0.27 mmol) are suspended in 14 ml of acetone. After addition of caesium carbonate (2427 mg, 0.74 mmol), the reaction mixture is stirred at reflux for 3 hours. After cooling, the batch is concentrated, the residue is taken up in ethyl acetate, and the organic phase is washed with water and dried over sodium sulphate. After removal of the solvent, the residue (144 mg, 97% of theory) is employed in the next reaction without further purification.

(RS)-N-(Ethoxycarbonyl)-S-[3-({[4-(isopropylamino)-6-methoxyquinazolin-7-yl]oxy}-methyl)phenyl]-S-methylsulphoximide (105 mg, 0.22 mmol) is introduced into 2.5 ml of ethanol. 1.0 ml of a 1-molar ethanolic sodium ethoxide solution is added and the mixture is heated to 80° C., until starting material is no longer present according to TLC checking (eluent dichloromethane/methanol 10:1). The reaction solution is concentrated in vacuo, and the residue is taken up in ethyl acetate and washed with saturated sodium carbonate solution. The organic phase is dried over sodium sulphate and concentrated. The crude product is purified by preparative HPLC and the desired product is obtained in 36% yield (32 mg).

¹H-NMR (400 MHz, DMSO-d6): δ 1.27 (d, 6H), 3.08 (s, 3H), 3.92 (s, 3H), 4.27 (s, 1H), 4.50 (dsept, 1H), 5.35 (s, 2H), 7.20 (s, 1H), 7.56 (d, 1H), 7.63-7.68 (m, 2H), 7.77 (d, 1H), 7.92 (d, 1H), 8.07 (s, 1H), 8.32 (s, 1H).

Example 2.7

(RS)-S-[4-({[6-Bromo-4-(isopropylamino)quinazolin-7-yl]oxy}methyl)phenyl]-N-(ethoxycarbonyl)-S-methylsulphoximide

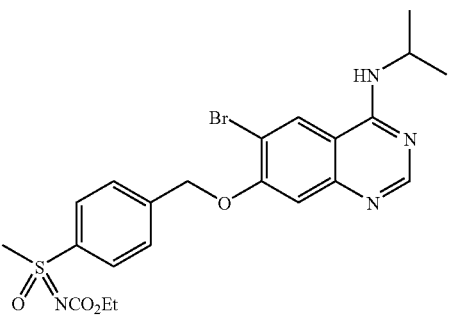

2.7. a) Preparation of the Intermediates

Compound 2.7. a.1

(RS)-S-Methyl-S-(m-tolyl)sulphoximide

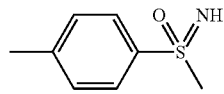

According to GWP 2, in the case of the reaction of 4-methylphenylsulphinyl (1.0 g, 6.5 mmol), the desired product is obtained after chromatographic purification (silica gel, hexane/ethyl acetate: 0→100% ethyl acetate, then ethyl acetate/methanol: 9/1) in 93% yield (1.02 g).

$^1$H-NMR (300 MHz, DMSO-d6): δ 2.35 (s, 3H), 2.98 (s, 3H), 4.97 (s, 1H), 7.36 (d, 2H), 7.77 (d, 2H).

Compound 2.7. a.2

(RS)-N-(Ethoxycarbonyl)-S-methyl-S-(p-tolyl)sulphoximide

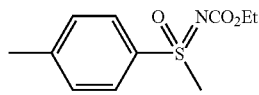

According to GWP 3, in the case of the reaction of (RS)-S-methyl-S-(m-tolyl)-sulphoximide (1.02 g, 6.03 mmol), the desired product is obtained after chromatographic purification (silica gel, hexane/ethyl acetate: 0→100% ethyl acetate, then ethyl acetate/methanol: 9/1) in 96% yield (1.39 g).

$^1$H-NMR (300 MHz, DMSO-d6): δ 1.05 (t, 3H), 2.38 (s, 3H), 3.39 (s, 3H), 3.82-3.92 (m, 2H), 7.45 (d, 2H), 7.79 (d, 2H).

Compound 2.7. a.3

(RS)-S-[4-(Bromomethyl)phenyl]-N-(ethoxycarbonyl)-S-methylsulphoximide

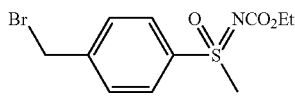

According to GWP 4, in the case of the reaction of (RS)-N-(ethoxycarbonyl)-S-methyl-S-(p-tolyl)sulphoximide (0.5 g, 2.07 mmol), the desired product is obtained after chromatographic purification (silica gel, hexane/ethyl acetate: 0→100% ethyl acetate, then ethyl acetate/methanol: 4/1) in 65% yield (0.43 g).

$^1$H-NMR (400 MHz, DMSO-d6): δ 1.04 (t, 3H), 3.43 (s, 3H), 3.82-3.91 (m, 2H), 4.77 (s, 2H), 7.70 (d, 2H), 7.90 (d, 2H).

Compound 2.7. a.4

6-Bromo-7-methoxy-3H-quinazolin-4-one

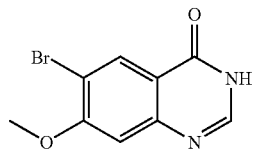

2-Amino-5-bromo-4-methoxybenzoic acid (1.56 g, 6.34 mmol) is dissolved in methanol (15 ml), treated with piperidine (0.063 ml, 0.63 mmol) and 1,3,5-triazine (772 mg, 9.5 mmol) and refluxed for one hour. After cooling to room temperature, the resulting crystals are filtered off with suction and washed with methanol. The desired product is obtained in 63% yield (1.01 g).

$^1$H-NMR (300 MHz, DMSO-d6): δ 3.95 (s, 3H), 7.20 (s, 1H), 8.08 (s, 1H), 8.16 (s, 1H), 12.2 (br, 1H).

Compound 2.7. a.5

(6-Bromo-4-methoxyquinazolin-4-yl)isopropylamine

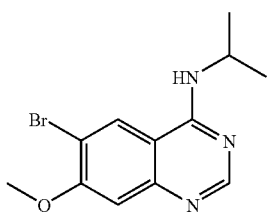

6-Bromo-7-methoxy-3H-quinazolin-4-one (1.01 g, 3.96 mmol) and N,N-(diisopropyl-ethylamine (1.78 ml, 10.4 mmol) are introduced into 1,2-dichloroethane (19 ml), treated dropwise with POCl$_3$ (0.46 ml, 4.95 mmol) and then stirred at 80° C. for 2 h. The reaction mixture is subsequently concentrated to dryness. The residue is taken up in isopropanol (10 ml), treated with isopropylamine (0.34 ml, 3.96 mmol) and stirred for 30 minutes at 80° C. After cooling to room temperature, the resulting precipitate is filtered off with suction and dried in vacuo. The desired product is obtained in 46% yield (530 mg).

$^1$H-NMR (400 MHz, DMSO-d6): δ 1.20 (d, 6H), 3.93 (s, 3H), 4.38-4.46 (m, 1H), 7.14 (s, 1H), 7.87 (d, 1H), 8.38 (s, 1H), 8.63 (s, 1H).

Compound 2.7. a.6

6-Bromo-4-(isopropylamino)quinazolin-7-ol

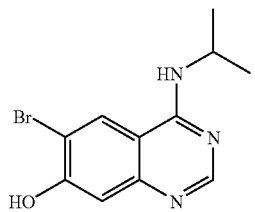

(6-Bromo-4-methoxyquinazolin-4-yl)isopropylamine (430 mg, 1.45 mmol) is introduced into $CH_2Cl_2$ (15 ml), a 1M boron tribromide solution (30 ml) in methylene chloride is added dropwise at room temperature and the mixture is stirred at RT for 20 hours. The reaction is terminated by addition of methanol. After removal of the solvent, the residue is treated with triethylamine and concentrated again. The desired product is obtained after chromatographic purification (silica gel, dichloromethane/methanol: 0→20% methanol), in 12% yield (50 mg).

$^1$H-NMR (300 MHz, DMSO-d6): δ 1.23 (d, 6H), 4.48-4.57 (m, 1H), 7.13 (s, 1H), 8.56 (s, 1H), 8.71 (s, 1H).

2.7. b) Preparation of the Final Product

6-Bromo-4-(isopropylamino)quinazolin-7-ol (50 mg, 0.18 mmol) and (RS)-S-[4-(bromomethyl)phenyl]-N-(ethoxycarbonyl)-S-methylsulphoximide (86 mg, 0.27 mmol) are suspended in acetone (10 ml), treated with potassium carbonate (45 mg, 0.33 mmol) and refluxed for 6 hours. After cooling, the batch is diluted with ethyl acetate and washed with water. The organic phase is dried over sodium sulphate and subsequently concentrated. The desired product is obtained after chromatographic purification (silica gel, dichloromethane/methanol: 0→20% methanol), in 45% yield (42 mg).

$^1$H-NMR (300 MHz, DMSO-d6): δ 1.09 (t, 3H), 1.25 (d, 6H), 3.49 (s, 3H), 3.86-3.97 (m, 2H), 4.41-4.53 (m, 1H), 5.52 (s, 2H), 7.31 (s, 1H), 7.82 (d, 2H), 7.94 (d, 1H), 8.03 (d, 2H), 8.42 (s, 1H), 8.72 (s, 1H).

Example 2.8

(RS)-S-[4-({[6-Bromo-4-(isopropylamino)quinazolin-7-yl]oxy}methyl)phenyl]-S-methylsulphoximide

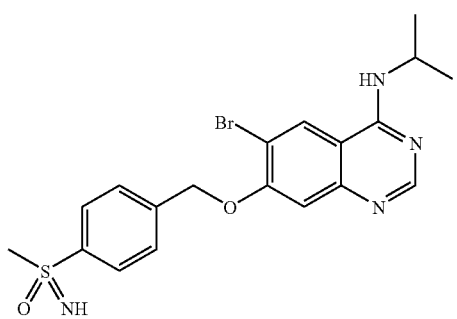

(RS)-S-[4-({[6-Bromo-4-(isopropylamino)quinazolin-7-yl]oxy}methyl)phenyl]-N-(ethoxycarbonyl)-S-methylsulphoximide (37 mg, 0.07 mmol) is dissolved in ethanol (5 ml), treated with sodium ethoxide (16 mg, 0.26 mmol), and is stirred at 60° C. for 6 hours and subsequently stirred at room temperature overnight. The batch is added to dilute aqueous sodium carbonate solution and extracted with ethyl acetate. The combined organic phases are dried over sodium sulphate and concentrated. The desired product is obtained after chromatographic purification (silica gel, dichloro-methane/methanol: 020% methanol) of the residue in 79% yield (25 mg)

$^1$H-NMR (300 MHz, DMSO-d6): δ 1.20 (d, 6H), 3.04 (s, 3H), 4.25-4.48 (m, 2H), 5.44 (s, 2H), 7.24 (s, 1H), 7.68 (d, 2H), 7.91-7.96 (m, 3H), 8.38 (s, 1H), 8.67 (s, 1H).

Example 2.9

(RS)-N-(Ethoxycarbonyl)-S-ethyl-S-[3-({[4-(isopropylamino)-6-methoxy-quinazolin-7-yl]oxy}methyl)phenyl]sulphoximide

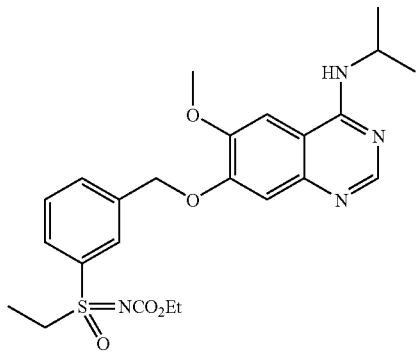

4-(Isopropylamino)-6-methoxyquinazolin-7-ol (50 mg, 0.21 mmol) and (RS)-S-[3-(bromomethyl)phenyl]-N-(ethoxycarbonyl)-S-ethylsulphoximide (108 mg, 0.32 mmol) are suspended in 5.0 mL of acetone. After addition of potassium carbonate (55 mg, 0.4 mmol), the reaction mixture is refluxed for 6 hours. The batch is diluted with ethyl acetate and the organic phase is washed with water and dried over sodium sulphate to leave, after removal of the solvent and also after chromatographic purification (silica gel, hexane/ethyl acetate: 0→100% ethyl acetate, followed by ethyl acetate/methanol: 9/1) the desired product in 62% yield (65 mg).

$^1$H-NMR (300 MHz, DMSO): ∂ 0.99-1.07 (m, 6H), 1.23 (d, 6H), 3.47-3.60 (m, 2H), 3.76-3.90 (m, 5H), 4.43-4.49 (m, 1H), 5.35 (s, 2H), 7.16 (s, 1H), 7.54 (d, 1H), 7.62 (s, 1H), 7.70 (t, 1H), 7.82-7.85 (m, 2H, 7.99 (s, 1H), 8.28 (s, 1H).

Example 2.10

(RS)-S-Ethyl-S-[3-({[4-(isopropylamino)-6-methoxyquinazolin-7-yl]oxy}-methyl)phenyl]sulphoximide

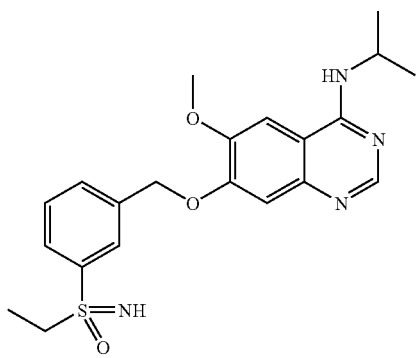

According to GWP 6, the conversion of (RS)-N-(ethoxycarbonyl)-S-ethyl-S-[3-({[4-(isopropylamino)-6-methoxyquinazolin-7-yl]oxy}methyl)phenyl]sulphoximide (64 mg, 0.13 mmol) and chromatographic purification (silica gel, hexane, ethyl acetate/methanol: 0→10% methanol, followed by dichloromethane/methanol: 0→15% methanol) gives the desired product in 82% yield (45 mg).

$^1$H-NMR (300 MHz, DMSO): ∂ 1.01 (t, 3H), 1.23 (d, 6H), 3.08 (q, 2H), 3.88 (s, 3H), 4.19 (s, 1H), 4.42-4.49 (m, 1H), 5.32 (s, 2H), 7.15 (s, 1H), 7.54 (d, 1H), 7.59-7.64 (m, 2H), 7.73 (d, 1H), 7.81-7.83 (d, 1H), 7.97 (s, 1H), 8.28 (s, 1H).

Example 2.11

(RS)-S-[3-({[6-Cyano-4-(isopropylamino)quinazolin-7-yl]oxy}methyl)phenyl]-N-(ethoxycarbonyl)-S-methylsulphoximide

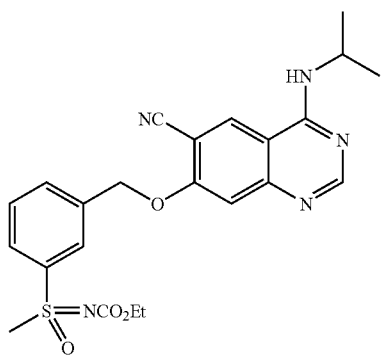

2.11. a) Preparation of the Intermediates

Compound 2.11. a.1

6-(Hydroxymethyl)-4-(isopropylamino)quinazolin-7-ol

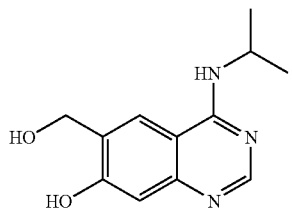

Acetate salt of the compound 3.5. a.1 (1.05 g, 3.13 mmol) is presented as an initial charge in 60 mL of tetrahydrofuran and at 0° C. admixed portionwise with lithium aluminium hydride (590 mg, 15.7 mmol). This is followed by stirring at room temperature for 90 minutes. The reaction is discontinued by addition of 10% aqueous ammonium chloride solution at 0° C. The batch is diluted with water and extracted with ethyl acetate, and the combined organic phases are dried over sodium sulphate to leave, after removal of the solvent, the desired product in 70% yield (510 mg).

$^1$H-NMR (300 MHz, DMSO): ∂ 1.24 (d, 6H), 4.47-4.54 (m, 1H), 4.59 (s, 2H), 5.15 (br, 1H), 6.92 (s, 1H), 7.74 (d, 1H), 8.19 (s, 1H), 8.28 (s, 1H), 10.30 (br, 1H).

Compound 2.11. a.2

7-Hydroxy-4-(isopropylamino)quinazoline-6-carbaldehyde

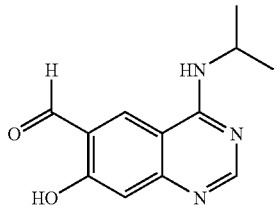

6-(Hydroxymethyl)-4-(isopropylamino)quinazoline-7-ol (510 mg, 2.19 mmol) is dissolved in 50 mL of toluene and 5 mL of dimethylformamide and at room temperature admixed portionwise with manganese(IV) oxide (1.9 g, 21.9 mmol). After 24 hours the batch is filtered through Celite and washed with dichloro-methane/methanol 9/1. Removal of the solvent and also chromatographic purification (silica gel, dichloromethane/methanol: 0→50% methanol) gives the desired product in 56% yield (280 mg).

$^1$H-NMR (300 MHz, DMSO): ∂ 1.20 (d, 6H), 4.41-4.52 (m, 1H), 6.97 (s, 1H), 8.29-8.32 (m, 2H), 8.72 (s, 1H), 10.30 (s, 1H), 11.22 (br, 1H).

Compound 2.11. a.3

7-Hydroxy-4-(isopropylamino)quinazoline-6-carbonitrile

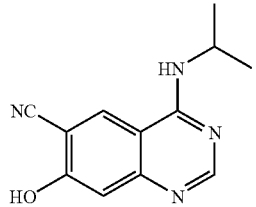

7-Hydroxy-4-(isopropylamino)quinazoline-6-carbaldehyde (310 mg, 1.34 mmol) is presented as an initial charge in acetic acid (7 mL, 81 mmol) and admixed with sodium acetate (366 mg, 3.3 mmol) and also hydroxylamine hydrochloride (186 mg, 2.68 mmol). The batch is stirred at 130° C. for 18 hours. After cooling to room temperature, the batch is diluted with water and extracted with ethyl acetate. The combined organic phases are dried over sodium sulphate. Removal of the solvent and also chromatographic purification (silica gel, dichloromethane/methanol: 0→30% methanol) of the residue gives the desired product in 38% yield (116 mg).

$^1$H-NMR (400 MHz, DMSO): ∂ 1.20 (d, 6H), 4.38-4.46 (m, 1H), 6.94 (s, 1H), 8.06 (d, 1H), 8.35 (s, 1H), 8.74 (s, 1H), 11.87 (br, 1H).

2.11. b) Preparation of the Final Product

7-Hydroxy-4-(isopropylamino)quinazoline-6-carbonitrile (50 mg, 0.22 mmol) and (RS)-S-[3-(bromomethyl)phenyl]-N-(ethoxycarbonyl)-S-methylsulphoximide (105 mg, 0.33 mmol) are suspended in 5.0 mL of acetone. After addition of potassium carbonate (56 mg, 0.4 mmol), the reaction mixture is refluxed for 6 hours. The batch is diluted with ethyl acetate and the organic phase is washed with water and dried over sodium sulphate. Removal of the solvent and also chromatographic purification (silica gel, dichloromethane/methanol: 0→30% methanol) gives the desired product in 74% yield (75 mg).

$^1$H-NMR (400 MHz, DMSO): ∂ 1.01 (t, 3H), 1.21 (d, 6H), 3.44 (s, 3H), 3.80-3.89 (m, 2H), 4.38-4.47 (m, 1H), 5.50 (s, 2H), 7.33 (s, 1H), 7.73 (t, 1H), 7.86 (d, 1H), 7.93 (d, 1H), 8.08 (s, 1H), 8.12 (d, 1H), 8.44 (s, 1H), 8.88 (s, 1H).

Example 2.12

(RS)-S-[3-({[6-Cyano-4-(isopropylamino)quinazolin-7-yl]oxy}methyl)phenyl]-S-methylsulphoximide

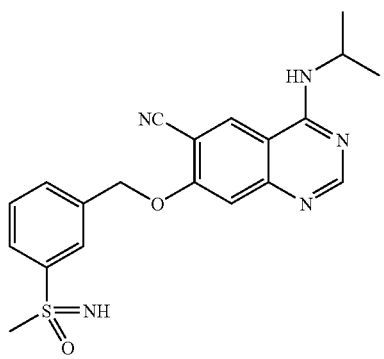

According to GWP 6, the conversion of (RS)-S-[3-({[6-cyano-4-(isopropylamino)-quinazolin-7-yl]oxy}methyl) phenyl]-N-(ethoxycarbonyl)-S-methylsulphoximide (65 mg, 0.14 mmol) and chromatographic purification (silica gel, dichloromethane/methanol: 0→30% methanol) gives the desired product in 74% yield (41 mg).

$^1$H-NMR (300 MHz, DMSO): ∂ 1.21 (d, 6H), 3.04 (s, 3H), 4.24 (s, 1H), 4.37-4.49 (m, 1H), 5.47 (s, 2H), 7.32 (s, 1H), 7.65 (t, 1H), 7.75 (d, 1H), 7.90 (d, 1H), 8.06 (s, 1H), 8.12 (d, 1H), 8.44 (s, 1H), 8.87 (s, 1H).

3. Process Variant 3

Example 3.1

(RS)-S-(4-{[4-(Isopropylamino)-6-methoxyquinazolin-7-yl]oxy}butyl)-S-methyl-N-[(4-nitrophenyl)sulphonyl]sulphoximide

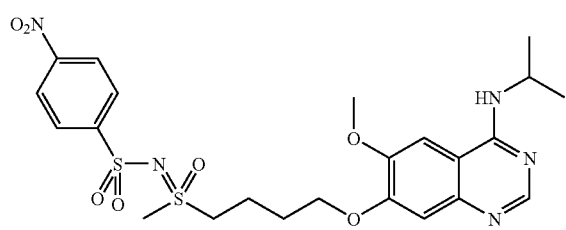

3.1. a) Preparation of the Intermediates

Compound 3.1. a.1

Isopropyl-[6-methoxy-7-(4-methylsulphanylbutoxy)quinazolin-4-yl]amine

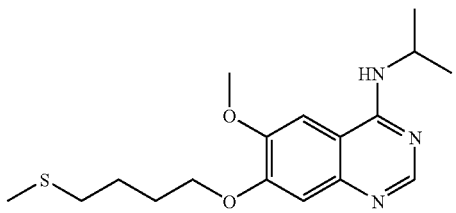

4-(Isopropylamino)-6-methoxyquinazolin-7-ol (380 mg, 1.63 mmol) is dissolved in methylene chloride (10 ml) under an argon atmosphere, treated with triphenylphosphine (641 mg, 2.44 mmol), azodicarboxylic acid dipiperidide (617 mg, 2.44 mmol) and 4-(methylthio)butan-1-ol (235 mg, 1.96 mmol) and stirred at room temperature for 20 hours. The batch is diluted with methylene chloride and water, and the organic phase is separated off and concentrated. The desired product is obtained after chromatography by means of preparative HPLC in 43% yield (258 mg).

$^1$H-NMR (400 MHz, DMSO-d6): δ 1.27 (d, 6H), 1.67-1.77 (m, 2H), 1.82-1.90 (m, 2H), 2.05 (s, 3H), 2.56 (t, 2H), 3.90 (s, 3H), 4.11 (t, 2H), 4.49 (dsept, 1H), 7.06 (s, 1H), 7.52 (d, 1H), 7.60 (s, 1H), 8.31 (s, 1H).

Compound 3.1. a.2

(RS)-S-(4-{[4-(Isopropylamino)-6-methoxyquinazolin-7-yl]oxy}butyl)-S-methyl-N-[(4-nitrophenyl)sulphonyl]sulphimide

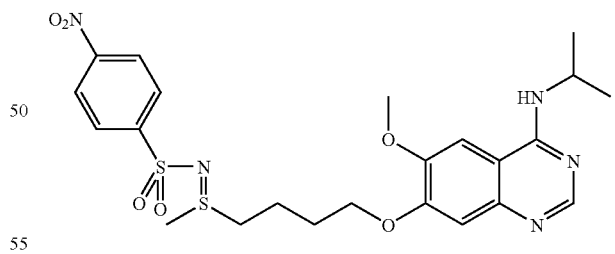

According to Bolm et al. (Org. Lett 2006, 8(11), 2349-2352), isopropyl-[6-methoxy-7-(4-methylsulphanylbutoxy) quinazolin-4-yl]amine (250 mg, 075 mmol) is dissolved in acetonitrile (7 ml) under an argon atmosphere, treated with N-(p-nitrosulphonyl-phenyl)imino)phenyliodinane (452 mg, 1.12 mmol) and iron(III) acetylacetonate (14 mg, 0.04 mmol) and stirred at room temperature for 20 hours. The desired product is obtained after removal of the solvent and chromatographic purification (silica gel, dichloromethane/methanol: 25/1) in 67% yield (272 mg).

$^1$H-NMR (400 MHz, DMSO-d6): δ 1.28 (d, 6H), 1.60-1.80 (m, 4H), 2.71 (s, 3H), 3.08-3.22 (m, 2H), 3.90 (s, 3H), 3.99-4.04 (m, 2H), 4.46-4.55 (m, 1H), 7.03 (s, 1H), 7.59 (br s, 1H), 7.62 (s, 1H), 7.98 (d, 2H), 8.30 (d, 2H), 8.34 (s, 1H).

3.1. b) Preparation of the Final Product (RS)-S-(4-{[4-(Isopropylamino)-6-methoxyquinazolin-7-yl]oxy}butyl)-S-methyl-N-[(4-nitrophenyl)sulphonyl]sulphimide (268 mg, 0.5 mmol) is suspended in acetonitrile (0.6 ml) and ethanol (8 ml), treated with potassium carbonate (156 g, 1.13 mmol) and a solution of ethanol (8 ml) and hydrogen peroxide (0.6 ml) and stirred at room temperature for 20 hours. The reaction batch is diluted with water. After removing ethanol and acetonitrile, the aqueous phase is extracted with methylene chloride and small amounts of methanol as a solubilizer. The organic phase is dried over sodium sulphate. After removal of the solvent, the residue is dissolved in a little methylene chloride, treated with diethyl ether, triturated and concentrated again. The desired product is obtained in 88% yield (267 mg).

LC-MS (method: see Compound 1.16. a.3): $R_t$=1.34 min; MS (ESI pos.): m/z=552 (M+H$^+$).

Example 3.2

(RS)-S-(4-{[4-(Isopropylamino)-6-methoxyquinazolin-7-yl]oxy}butyl)-S-methyl-sulphoximide

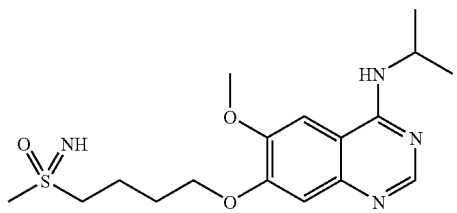

(RS)-S-(4-{[4-(Isopropylamino)-6-methoxyquinazolin-7-yl]oxy}butyl)-S-methyl-N-[(4-nitrophenyl)sulphonyl]sulphoximide (267 mg, 0.48 mmol) is dissolved in acetonitrile (7 ml), treated with caesium carbonate (266 mg, 0.82 mmol) and thiophenol (86 mg, 0.77 mmol) and stirred at room temperature for 20 hours. The reaction batch is diluted with water and methylene chloride. The organic phase is separated off and dried over sodium sulphate. The desired product is obtained after removal of the solvent and preparative HPLC in 51% yield (126 mg).

$^1$H-NMR (400 MHz, DMSO-d6): δ 1.27 (d, 6H), 1.83-1.95 (m, 4H), 2.89 (s, 3H), 3.12-3.18 (m, 2H), 3.61 (s, 1H), 3.91 (s, 3H), 4.10-4.15 (m, 2H), 4.49 (dsept, 1H), 7.08 (s, 1H), 7.53 (d, 1H), 7.61 (s, 1H), 8.31 (s, 1H).

Example 3.3

(RS)-S-(4-{[4-(Isopropylamino)-6-methoxyquinazolin-7-yl]oxy}propyl)-S-methyl-N-[(4-nitrophenyl)sulphonyl]sulphoximide

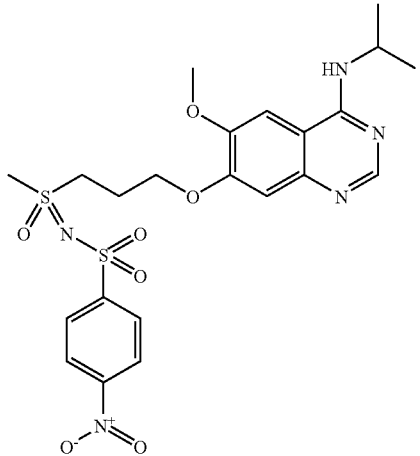

3.3. a) Preparation of the Intermediates

Compound 3.3. a.1

Isopropyl-[6-methoxy-7-(4-methylsulphanylpropoxy)quinazolin-4-yl]amine

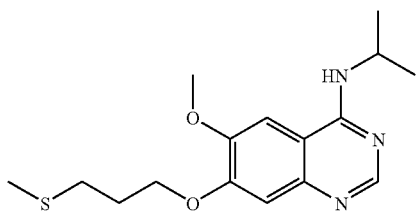

4-(Isopropylamino)-6-methoxyquinazolin-7-ol (400 mg, 1.72 mmol) is dissolved in methylene chloride (10 ml) under an argon atmosphere, treated with triphenylphosphine (675 mg, 2.57 mmol), azodicarboxylic acid dipiperidide (649 mg, 2.57 mmol) and 3-(methylthio)propan-1-ol (219 mg, 2.06 mmol) and stirred at room temperature for 20 hours. The batch is diluted with methylene chloride and water, and the organic phase is separated off and concentrated. The desired product is obtained after preparative HPLC in 35% yield (190 mg).

$^1$H-NMR (400 MHz, DMSO-d6): δ 1.27 (d, 6H), 2.04 (tt, 2H), 2.08 (s, 3H), 2.64 (t, 2H), 3.91 (s, 3H), 4.17 (t, 2H), 4.49 (dsept, 1H), 7.07 (s, 1H), 7.53 (d, 1H), 7.61 (s, 1H), 8.32 (s, 1H).

85

Compound 3.3. a.2

(RS)-S-(4-{[4-(Isopropylamino)-6-methoxyquinazolin-7-yl]oxy}propyl)-S-methyl-N-[(4-nitrophenyl)sulphonyl]sulphimide

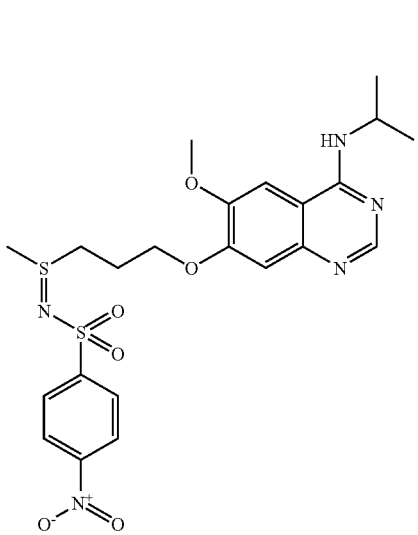

Isopropyl-[6-methoxy-7-(4-methylsulphanylpropoxy)quinazolin-4-yl]amine (95 mg, 0.296 mmol) is dissolved in acetonitrile (2 ml) under an argon atmosphere, treated with iodosylbenzene (104 mg, 0.47 mmol), 4-nitrobenzenesulphonamide (90 mg, 0.44 mmol) and iron(III) acetylacetonate (5.2 mg, 0.015 mmol) and stirred at room temperature for 2 hours. The desired product is obtained after removal of the solvent and chromatographic purification (silica gel, ethyl acetate then dichloromethane/methanol: 10/1), in 31% yield (48 mg).

LC-MS (Instrument: Micromass Quattro LCZ with HPLC Agilent Series 1100; column: Phenomenex Onyx Monolithic C18, 100 mm×3 mm. eluent A: 1 l of water+0.5 ml of 50% strength formic acid, eluent B: 1 l of acetonitrile+0.5 ml of 50% strength formic acid; gradient: 0.0 min 90% A→2 min 65% A→4.5 min 5% A→6 min 5% A; flow: 2 ml/min; oven: 40° C.; UV detection: 208-400 nm): $R_t$=1.99 min; MS (ESI pos.): m/z=522 (M+H$^+$).

3.3. b) Preparation of the Final Product (RS)-S-(4-{[4-(Isopropylamino)-6-methoxyquinazolin-7-yl]oxy}propyl) -S-methyl-N-[(4-nitrophenyl)sulphonyl]sulphimide (45 mg, 0.086 mmol) and potassium carbonate (25 mg, 0.18 mmol) are dissolved in N,N-dimethylformamide (1 ml) and treated at 0° C. with meta-chloroperbenzoic acid (26 mg, 0.104 mmol). After 2 hours at room temperature, the batch is added to water, extracted with ethyl acetate and the combined organic phases are dried over sodium sulphate. The desired product is obtained after removal of the solvent and subsequent purification (silica gel, dichloromethane/methanol: 100/3) with 47% yield (22 mg).

$^1$H-NMR (400 MHz, DMSO-d6): δ 1.27 (d, 6H), 2.24-2.34 (m, 2H), 3.59 (s, 3H), 3.72-3.90 (m, 2H), 3.91 (s, 3H), 4.22 (t, 2H), 4.45-4.54 (m, 1H), 7.06 (s, 1H), 7.56 (d, 1H), 7.63 (s, 1H), 8.10 (d, 2H), 8.32 (s, 1H), 8.36 (d, 2H).

86

Example 3.4

(RS)-S-(4-{[4-(Isopropylamino)-6-methoxyquinazolin-7-yl]oxy}propyl)-S-methyl-sulphoximide

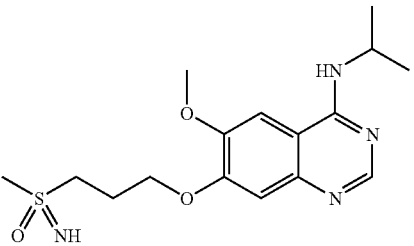

For the removal of the protective group on the sulphoximine, a 3-(4-tritylmercapto)-phenylpropionyl AM resin is used, which is prepared for the reaction in the following way (based on 89 mg, 0.078 mmol of resin): a) The resin is suspended 1/1 in 2 ml of methylene chloride/trifluoroacetic acid, shaken for 5 minutes and the solution is separated off. This process is repeated five times until the solution is colourless. The resin is in each case washed with methylene chloride and tetrahydrofuran. b) The resin is subsequently taken up in 2 ml of tetrahydrofuran/methanol 9/1 and treated with sodium ethoxide in methanol (5.4 M solution, 29 μl), and shaken for 5 minutes. The reaction solution is separated off and the resin is washed with tetrahydrofuran. (RS)-S-(4-{[4-(Isopropylamino)-6-methoxyquinazolin-7-yl]oxy}propyl)-S-methyl-N-[(4-nitrophenyl)sulphonyl]sulphoximide (21 mg, 0.039 mmol) is introduced into ethanol (1.5 ml) and treated with the prepared resin (455 mg, 0.39 mmol) and shaken overnight. The resin is filtered off and washed with tetrahydrofuran. The desired product is obtained after removing the solvents and chromatographic purification (silica gel, dichloromethane/methanol: 5/1) in 42% yield (5.8 mg).

$^1$H-NMR (400 MHz, DMSO-d6): δ 1.27 (d, 6H), 2.18-2.27 (m, 2H), 2.94 (s, 3H), 3.21 (t, 2H), 3.79 (br s, 1H), 3.91 (s, 3H), 4.22 (t, 2H), 4.49 (dsept, 1H), 7.08 (s, 1H), 7.56 (d, 1H), 7.63 (s, 1H), 8.32 (s, 1H).

Example 3.5

Ethyl 4-(isopropylamino)-7-[(RS)-3-{S-methyl-N-[(4-nitrophenyl)sulphonyl]-sulphonimidoyl}propoxy]quinazoline-6-carboxylate

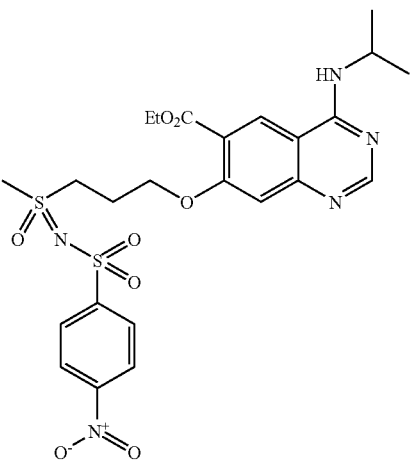

3.5. a) Preparation of the Intermediates

Compound 3.5. a.1

Ethyl 7-hydroxy-4-(isopropylamino)quinazoline-6-carboxylate

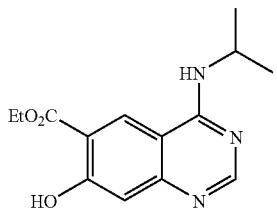

According to GWP 5, ethyl 5-cyano-4-{(E/Z)-[(dimethylamino)methylene]amino}-2-hydroxybenzoate (1.9 g, 7.27 mmol) is reacted with isopropylamine (516 mg, 8.73 mmol) in acetonitrile (10 ml) and acetic acid (5 ml). After cooling, the batch is diluted with water, rendered alkaline with concentrated sodium hydroxide solution, and extracted with ethyl acetate and methanol as a solubilizer. The organic phase is dried over sodium sulphate. After removal of the solvent, the residue is triturated a number of times with methylene chloride and employed in the next reaction without further purification. The desired product is obtained in 66% yield (1.6 g)

$^1$H-NMR (400 MHz, DMSO-d6): δ 1.26 (d, 6H), 1.39 (t, 3H), 1.91 (s, 3H), 4.43 (q, 2H), 4.52 (dsept, 1H), 7.01 (s, 1H), 8.25 (d, 1H), 8.37 (s, 1H), 8.81 (s, 1H), 10.82 (br s, 1H), 11.97 (br s, 1H).

Compound 3.5. a.2

Ethyl 4-(isopropylamino)-7-[3-(methylsulphanyl)propoxy]quinazoline-6-carboxylate

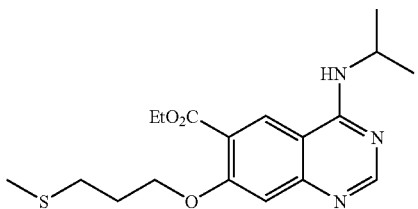

Sodium hydride (60%, 251 mg, 6.3 mmol) is introduced into N,N-dimethylformamide (13 ml), treated in portions with ethyl 7-hydroxy-4-(isopropylamino)quinazoline-6-carboxylate (1 g, 2.98 mmol) and subsequently stirred at room temperature for 30 minutes. After addition of a solution of 3-(methylthio)-1-(tosyloxy)propane (777 mg, 2.98 mmol) in N,N-dimethylformamide (8 ml), the mixture is stirred at 80° C. for one hour. After cooling, the batch is treated with water and ethyl acetate, and the organic phase is separated off and dried over sodium sulphate. The desired product is obtained after removing the solvents and preparative HPLC in 48% yield (548 mg).

$^1$H-NMR (400 MHz, DMSO-d6): δ 1.25 (d, 6H), 1.34 (t, 3H), 2.02 (quint, 2H), 2.07 (s, 3H), 2.68 (t, 2H), 4.21 (t, 2H), 4.33 (q, 2H), 4.50 (dsept, 1H), 7.13 (s, 1H), 8.12 (d, 1H), 8.42 (s, 1H), 8.64 (s, 1H).

Compound 3.5. a.3

Ethyl 4-(isopropylamino)-7-[(RS)-3-{S-methyl-N-[(4-nitrophenyl)sulphonyl]-sulphinimidoyl}propoxy]quinazoline-6-carboxylate

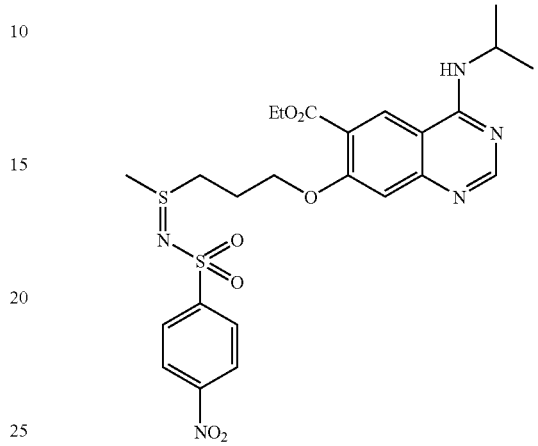

Ethyl 4-(isopropylamino)-7-[3-(methylsulphanyl)propoxy]quinazoline-6-carboxylate (237 mg, 0.65 mmol) is dissolved in acetonitrile (6 ml) under an argon atmosphere, treated with (N-(p-nitrosulphonylphenyl)imino)phenyliodinane (396 mg, 0.98 mmol) and iron(II) acetylacetonate (12 mg, 0.033 mmol) and stirred at room temperature for 20 hours. The desired product is obtained after removal of the solvent and chromatographic purification (silica gel, dichloromethane/methanol: 25/1), in 91% yield (347 mg).

$^1$H-NMR (400 MHz, DMSO-d6): δ 1.26 (d, 6H), 1.33 (t, 3H), 1.93-2.14 (m, 2H), 2.76 (s, 3H), 3.15-3.28 (m, 2H), 4.13 (t, 2H), 4.32 (q, 2H), 4.50 (dsept, 1H), 7.06 (s, 1H), 7.97 (d, 2H), 8.16 (d, 1H), 8.28 (d, 2H), 8.43 (s, 1H), 8.65 (s, 1H).

3.5. b) Preparation of the Final Product

Ethyl 4-(isopropylamino)-7-[(RS)-3-{S-methyl-N-[(4-nitrophenyl)sulphonyl]-sulphinimidoyl}propoxy]quinazoline-6-carboxylate (340 mg, 0.6 mmol) is suspended in acetonitrile (0.7 ml) and ethanol (10 ml), treated with potassium carbonate (188 g, 1.36 mmol) and a solution of ethanol (8 ml) and hydrogen peroxide (0.66 ml) and stirred at room temperature for 20 hours. The reaction batch is diluted with water. After removing ethanol and acetonitrile, the aqueous phase is extracted with methylene chloride. The organic phase is dried over sodium sulphate. After removal of the solvent, the residue is dissolved in a little methylene chloride, treated with diethyl ether, triturated and concentrated again. The desired product is obtained in 72% yield (271 mg).

LC-MS (apparatus type MS: Waters ZQ; apparatus type HPLC: Waters alliance 2795; column: Phenomenex Onyx Monolithic C18, 100 mm×3 mm; eluent A: 1 l of water+0.5 ml of 50% strength formic acid, eluent B: 1 l of acetonitrile+ 0.5 ml of 50% strength formic acid; gradient: 0.0 min 90% A→2 min 65% A→4.5 min 5% A→6 min 5% A; flow: 2 ml/min; oven: 40° C.; UV detection: 210 nm): $R_t$=2.58 min; MS (ESI pos.): m/z=580 (M+H$^+$).

Example 3.6

Ethyl 4-(isopropylamino)-7-[(RS)-3-(S-methylsulphonimidoyl)propoxy]-quinazoline-6-carboxylate

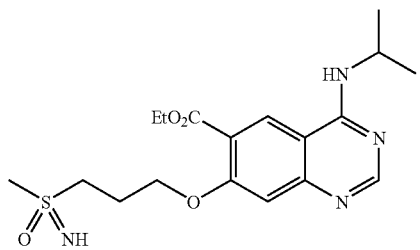

Ethyl 4-(isopropylamino)-7-[(RS)-3-{S-methyl -N-[(4-nitrophenyl)sulphonyl]-sulphonimidoyl}propoxy]quinazoline-6-carboxylate (270 mg, 0.47 mmol) is dissolved in acetonitrile (7 ml), treated with caesium carbonate (276 mg, 0.85 mmol) and thiophenol (90 mg, 0.82 mmol) and stirred at room temperature for 20 hours. The reaction batch is diluted with water and methylene chloride. The organic phase is separated off and dried over sodium sulphate. The desired product is obtained after removal of the solvent, preparative HPLC and subsequent repeated trituration of the residue in 45% yield (83 mg).

$^1$H-NMR (400 MHz, DMSO-d6): δ 1.25 (d, 6H), 1.35 (t, 3H), 2.17-2.25 (m, 2H), 2.93 (s, 3H), 3.22-3.27 (m, 2H), 3.75 (s, 1H), 4.27 (t, 2H), 4.35 (q, 2H), 4.50 (dsept, 1H), 7.14 (s, 1H), 8.14 (d, 1H), 8.42 (s, 1H), 8.66 (s, 1H).

Example 3.7

(RS)-S-[5-({[6-Bromo-4-(isopropylamino)quinazolin-7-yl]oxy}methyl)pyridin-3-yl]-S-methylsulphoximide

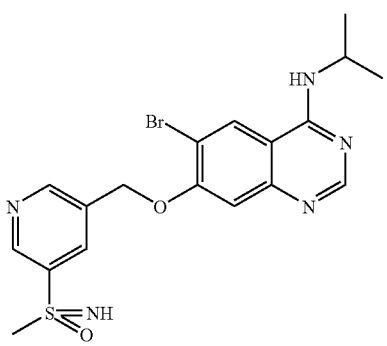

3.7. a) Preparation of the Intermediates

Compound 3.7. a.1

5-(Methylsulphanyl)pyridine-3-methanol

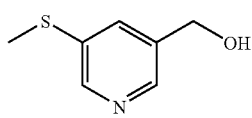

Methyl 5-methylsulphanylnicotinate (916 mg, 5 mmol) is dissolved in 150 mL of diethyl ether, admixed at 0° C. with lithium aluminium hydride (660 mg, 18 mmol) and subsequently stirred at room temperature for 90 minutes. The reaction is discontinued by addition of 10% ammonium chloride solution at 0° C. The batch is diluted with water and the aqueous phase is extracted with ether. Drying of the organic phase over sodium sulphate, concentrating the solvent and also chromatographic purification of the residue (silica gel, n-hexane/ethyl acetate: 50→100% ethyl acetate) gives the desired product in 7% yield (50 mg).

$^1$H-NMR (300 MHz, DMSO): ∂ 2.53 (s, 3H), 4.52 (s, 2H), 5.36 (br, 1H), 7.63 (t, 1H), 8.30 (d, 1H), 8.35 (d, 1H).

Compound 3.7. a.2

N'-(4-Bromo-2-cyano-5-{[5-(methylsulphanyl)pyridin-3-yl]methoxy}phenyl)-N,N-dimethylformimidamide

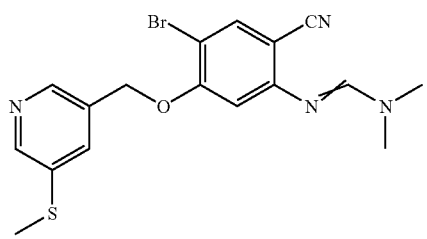

(E/Z)-N'-(4-Bromo-2-cyano-5-hydroxyphenyl)-N,N-dimethylformimidamide (242 mg, 0.9 mmol) is dissolved in 30 mL of tetrahydrofuran, admixed with 5-(methyl-sulphanyl)pyridine-3-methanol (280 mg, 1.8 mmol), triphenylphosphine (1.42 g, 5.41 mmol) and DEAD (943 mg, 5.41 mmol) and stirred at RT for 4 h. The reaction mixture is diluted with ethyl acetate and the organic phase is washed with saturated sodium bicarbonate solution. Drying of the organic phase over sodium sulphate, concentrating of the solvent and also chromatographic purification of the residue (silica gel, n-hexane, followed by ethyl acetate) gives the desired product in 11% yield (78 mg).

$^1$H-NMR (300 MHz, DMSO): ∂ 2.51 (s, 3H), 2.97 (s, 3H), 3.07 (s, 3H), 5.26 (s, 2H), 6.97 (s, 1H), 7.78 (t, 1H), 7.80 (s, 1H), 7.99 (s, 1H), 8.42 (d, 1H), 8.44 (d, 1H).

Compound 3.7. a.3

6-Bromo-N-isopropyl-7-{[5-(methylsulphanyl)pyridin-3-yl]methoxy}quinazolin-4-amine

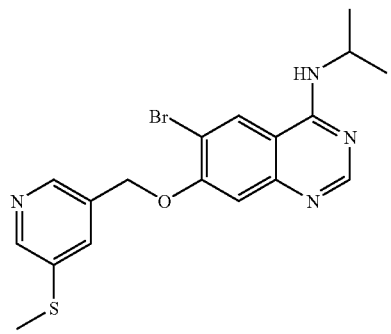

According to GWP 5, the reaction of N'-(4-bromo-2-cyano-5-{[5-(methylsulphanyl)-pyridin-3-yl]methoxy}phenyl)-N,N-dimethylformimidamide (540 mg, 1.33 mmol) with isopropylamine (0.14 mL, 1.6 mmol) and chromatography (silica gel, dichloro-methane/methanol: 0→30% methanol) gives the desired product in 77% yield (430 mg)

¹H-NMR (400 MHz, DMSO): ∂ 1.21 (d, 6H), 2.52 (s, 3H), 4.40-4.45 (m, 1H), 5.35 (s, 2H), 7.28 (s, 1H), 7.81 (t, 1H), 7.89 (d, 1H), 8.39 (s, 1H), 8.43 (d, 1H), 8.46 (d, 1H), 8.66 (s, 1H).

Compound 3.7. a.4

6-Bromo-N-isopropyl-7-{[5-(methylsulphinyl)pyridin-3-yl]methoxy}quinazolin-4-amine

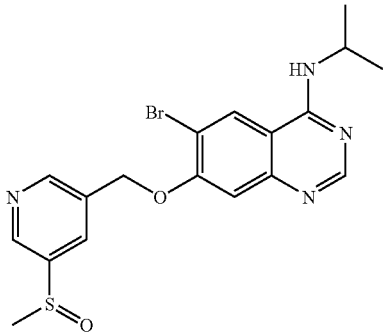

6-Bromo-N-isopropyl-7-{[5-(methylsulphanyl)pyridin-3-yl]methoxy}quinazolin-4-amine (430 mg, 1.03 mmol) is presented as an initial charge in 20 mL of chloroform and at 0° C. and at 0° C. admixed with meta-chloroperbenzoic acid (260 mg, 1.13 mmol). The batch is subsequently stirred at 0° C. for 45 minutes. The batch is introduced into 2N aqueous sodium hydroxide solution. The mixture is extracted with dichloromethane, the organic phase is dried over sodium sulphate and the solvent is concentrated. Chromatography (silica gel, dichloromethane/methanol: 0→30% methanol) gives the desired product in 74% yield (330 mg).

¹H-NMR (300 MHz, DMSO): ∂ 1.21 (d, 6H), 2.84 (s, 3H), 4.39-4.46 (m, 1H), 5.47 (s, 2H), 7.31 (s, 1H), 7.90 (d, 1H), 8.25 (t, 1H), 8.39 (s, 1H), 8.67 (s, 1H), 8.81 (d, 1H), 8.85 (d, 1H).

3.7. b) Preparation of the End Product

According to GWP 2,6-bromo-N-isopropyl-7-{[5-(methylsulphinyl)pyridin-3-yl]-methoxy}quinazolin-4-amine (270 mg, 0.62 mmol) is suspended in chloroform (10 mL) and admixed with sodium azide (90 mg, 1.39 mmol). Sulphuric acid (0.32 mL, 5.92 mmol) is added dropwise at 0° C. The reaction mixture is subsequently stirred at 45° C. for 24 hours. After cooling to room temperature, the batch is neutralized with 4N aqueous sodium hydroxide solution, concentrated under reduced pressure and evaporated off with toluene in a rotary evaporator. After purification of the residue by means of HPLC (column: XBridge C18 5µ 150×30 mm, eluent A: H₂O/0.2% NH₃, eluent B: methanol, gradient: 0.0 min 50% A→11 min 20% A→14.98 min 1% A, flow rate: 50 mL/min, room temperature, detection: DAD (200-400 nm) TAC; MS-ESI+ (m/z=160-1000 m/z) TIC, Rt: 4.5-5.2 min) the desired product is obtained in 21% yield (57 mg).

¹H-NMR (300 MHz, DMSO): ∂ 1.25 (d, 6H), 3.19 (s, 3H), 4.47 (m, 1H), 5.53 (s, 2H), 7.36 (s, 1H), 7.96 (br, 1H), 8.44-8.49 (m, 2H), 8.73 (s, 1H), 8.99 (d, 1H), 9.07 (d, 1H).

II. Biological Actions of the Compounds According to the Invention

TLR-Induced Cytokine Release in Human "Peripheral Blood Mononuclear Cells" (PBMC)

Test Principle

PBMCs isolated from human whole blood are stimulated using a TLR ligand. The cytokine determination is carried out by means of ELISA kits; a proliferation/cell metabolism determination is carried out using Alamar Blue.

PBMC Isolation:

For the cell preparation, about 200 ml of blood are treated with an anticoagulant (e.g. citrate Monovettes). Per Leucosep tube, 15 ml of Histopaque (room temperature, RT) are poured in and pressed downwards through the frit employed by brief initial centrifugation (one minute at 1000×g, RT). 20 ml of blood are added to the tubes prepared in this way and centrifuged at 800×g for 15 minutes (RT). After centrifugation, the following layered arrangement results from the top to the bottom: plasma—PBMC—Histopaque—filter disc—Histopaque—erythrocytes and granulocytes. The supernatant plasma is aspirated. The PBMC are transferred together with the underlying Histopaque to a new 50 ml tube, the contents of two Leucosep tubes always being added to one 50 ml tube. The 50 ml tubes are then filled to 50 ml with PBS. This cell suspension is centrifuged at 300×g (RT) for 10 minutes. The liquid supernatant is tipped off and the cell pellet is resuspended with a little PBS and subsequently filled to 50 ml with PBS. This washing step is repeated twice. The resulting pellet is taken up in a defined volume of medium (with additives). For the testing of the substances, PBMC are incubated for 18 hours with titrated concentrations of the test substances, e.g. in the presence or absence of TLR ligands. On the next day, the supernatants are investigated for the content of IL-12, TNF-alpha or other chemokines by means of specific ELISA. The metabolic activity of the treated cells is determined with the aid of Alamar Blue.

Results:

| Example | IC$_{50}$ (TNF-α) | IC$_{50}$ (IL-12) |
|---|---|---|
| 1.2 | 2.1 µM | 4.1 µM |
| 2.8 | 4 µM | 15 µM |
| 2.10 | 0.2 µM | 0.4 µM |
| 3.4 | 10 µM | 15 µM |
| 3.7 | 1 µM | 4 µM |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 08075043.3, filed Jan. 17, 2008, and U.S. Provisional Application Ser. No. 61/039,621, filed Mar. 26, 2008, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of formula (I):

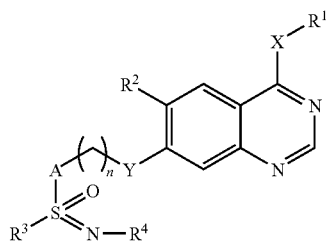

in which
R$^1$ represents
   (i) an aryl or heteroaryl ring, which in each case is optionally, identically or differently, mono- or polysubstituted by hydroxyl, —NR$^7$R$^8$, —NR$^6$—C(O)—R$^{11}$, —NR$^6$—C(O)—OR$^{11}$, —NR$^6$—C(O)—NR$^7$R$^8$, —NR$^7$—SO$_2$—R$^{11}$, cyano, halogen, C$_1$-C$_6$-alkoxy, —OCF$_3$, —CF$_3$, C$_1$-C$_6$-alkyl, C$_3$-C$_6$-cycloalkyl, and/or heterocyclyl having 3 to 8 ring atoms,
   (ii) a C$_1$-C$_6$-alkyl, C$_2$-C$_6$-alkenyl, or C$_2$-C$_6$-alkynyl, which in each case is optionally, identically or differently, mono- or polysubstituted by hydroxyl, —NR$^7$R$^8$, —NR$^6$—C(O)R$^{11}$, —NR$^6$—C(O)—OR$^{11}$, —NR$^6$—C(O)—NR$^7$R$^8$, —NR$^6$—SO$_2$—R$^{11}$, cyano, halogen, C$_1$-C$_6$-alkoxy, —OCF$_3$, —CF$_3$, C$_1$-C$_6$-alkyl, C$_3$-C$_6$-cycloalkyl, and/or heterocyclyl, or
   (iii) a C$_3$-C$_8$ cycloalkyl or heterocyclyl ring having 3 to 8 ring atoms, which in each case is optionally, identically or differently, mono- or polysubstituted by hydroxyl, —NR$^7$R$^8$, —NR$^6$—C(O)—R$^{11}$, —NR$^6$—C(O)—OR$^{11}$, —NR—C(O)—NR$^7$R$^8$, —NR$^6$—SO$_2$—R$^{11}$, cyano, halogen, C$_1$-C$_6$-alkoxy, —OCF$_3$, —CF$_3$, C$_1$-C$_6$-alkyl, C$_3$-C$_6$-cycloalkyl, and/or heterocyclyl having 3 to 8 ring atoms;
R$^2$ represents
   (i) hydrogen,
   (ii) hydroxyl, halogen, cyano, nitro, —CF$_3$, —OCF$_3$, —C(O)OR$^{11}$, —C(O)OH, —C(O)NR$^7$R$^8$, —C(S)NR$^7$R$^8$, —NR$^7$R$^8$, —NR$^6$—C(O)—OR$^{11}$, —NR$^6$—C(O)—OR$^{11}$, —NR$^6$—C(O)—NR$^7$R$^8$, —NR$^6$—SO$_2$—R$^{11}$,
   (iii) C$_1$-C$_6$-alkyl or C$_1$-C$_6$-alkoxy, which in each case is optionally, identically or differently, mono- or polysubstituted by halogen, hydroxyl, C$_1$-C$_6$-alkoxy, —CF$_3$, —OCF$_3$, or —NR$^7$R$^8$, or
   (iv) a C$_3$-C$_8$-cycloalkyl ring which is optionally, identically or differently, mono- or polysubstituted by halogen, hydroxyl, C$_1$-C$_6$-alkoxy, —CF$_3$, —OCF$_3$, —NR$^7$R$^8$, and/or C$_1$-C$_6$-alkyl;
R$^3$ represents a C$_1$-C$_6$-alkyl, C$_2$-C$_6$-alkenyl, C$_2$-C$_6$-alkynyl, a C$_3$—C$_7$-cycloalkyl, aryl ring, a heterocyclyl ring having 3 to 8 ring atoms, or a monocyclic heteroaryl ring, which in each case is optionally, identically or differently, mono- or polysubstituted by hydroxyl, —C(O)OR$^{11}$, —C(O)NR$^7$R$^8$, —NR$^7$R$^8$, cyano, halogen, —CF$_3$, C$_1$-C$_6$-alkoxy, —OCF$_3$, and/or C$_1$-C$_6$-alkyl;
R$^4$ represents hydrogen, —SO$_2$R$^{11}$, —C(O)R$^{11}$, —C(O)OR$^{11}$, —C(O)NR$^7$R$^8$, —C(S)OR$^{11}$, —C(S)NR$^7$R$^8$ or —R$^{11}$;

X, Y independently of one another represent —O— or —NR$^5$—;
A represents
   (i) a bond, or
   (ii) an aryl or heteroaryl ring, which in each case is optionally, identically or differently, mono- or polysubstituted by hydroxyl, —NR$^7$R$^8$, —NR$^6$—C(O)—R$^{11}$, —C(O)NR$^7$R$^8$, —NR$^6$—C(O)—OR$^{11}$, —NR$^6$—C(O)—NR$^7$R$^8$, —NR$^6$—SO$_2$—R$^{11}$, cyano, halogen, C$_1$-C$_6$-alkoxy, —OCF$_3$, —CF$_3$, C$_1$-C$_6$-alkyl, C$_3$-C$_6$-cycloalkyl, and/or heterocyclyl having 3 to 8 ring atoms;
n represents 1-6;
R$^5$ represents hydrogen;
R$^6$ represents hydrogen or a C$_1$-C$_6$-alkyl radical;
R$^7$ and R$^8$ independently of one another represent
   (i) hydrogen, and/or
   (ii) C$_1$-C$_6$-alkyl, C$_2$-C$_6$-alkenyl, C$_3$-C$_8$-cycloalkyl, aryl ring, a heterocyclyl ring having 3 to 8 ring atoms, and/or a heteroaryl ring, and in each case are optionally, identically or differently, mono- or polysubstituted by hydroxyl, —NR$^9$R$^{10}$, cyano, halogen, —CF$_3$, C$_1$-C$_6$-alkoxy, and/or —OCF$_3$, or
R$^7$ and R$^8$ together with the nitrogen atom form a 5- to 7-membered ring, which optionally in addition to the nitrogen atom contains 1 or 2 further heteroatoms, and which is optionally, identically or differently, mono- or polysubstituted by hydroxyl, —NR$^9$R$^{10}$, cyano, halogen, —CF$_3$, C$_1$-C$_6$-alkyl, C$_1$-C$_6$-alkoxy, and/or —OCF$_3$;
R$^9$ and R$^{10}$ independently of one another each represent hydrogen or C$_1$-C$_6$-alkyl, which in each case is optionally, identically or differently, mono- or polysubstituted by hydroxyl; and
R$^{11}$ represents a C$_1$-C$_6$-alkyl, C$_2$-C$_6$-alkenyl, C$_2$-C$_6$-alkynyl, C$_3$-C$_8$-cycloalkyl, aryl ring, a heterocyclyl ring having 3 to 8 ring atom, or a heteroaryl ring, which in each case is optionally, identically or differently, mono- or polysubstituted by hydroxyl, halogen, cyano, nitro, —NR$^7$R$^8$, C$_1$-C$_6$-alkyl, —CF$_3$, C$_1$-C$_6$-alkoxy, and/or —OCF$_3$;
or a pharmaceutically acceptable salt thereof, or a diastereomer or enantiomer thereof.

2. A compound according to claim 1, in which
R$^1$ represents
   (i) an aryl or heteroaryl ring, which in each case is optionally, identically or differently, mono- or polysubstituted by hydroxyl, —NR$^7$R$^8$, cyano, halogen, C$_1$-C$_6$-alkoxy, —NR$^6$—C(O)R$^{11}$, —OCF$_3$, —CF$_3$, or C$_1$-C$_6$-alkyl,
   (ii) a C$_1$-C$_6$-alkyl, which is optionally, identically or differently, mono- or polysubstituted by hydroxyl, —NR$^7$R$^8$, cyano, halogen, C$_1$-C$_6$-alkoxy, —NR$^6$—C(O)R$^{11}$, —OCF$_3$, —CF$_3$, or C$_1$-C$_6$-alkyl, or
   (iii) a C$_3$-C$_8$ cycloalkyl or heterocyclyl ring having 3 to 8 ring atoms and optionally identically or differently mono- or polysubstituted by hydroxyl, —NR$^7$R$^8$, cyano, halogen, C$_1$-C$_6$-alkoxy, —OCF$_3$, —CF$_3$, C$_1$-C$_6$-alkyl,
R$^2$ represents hydrogen, halogen, cyano, —C(O)OR$^{11}$, —C(O)OH, or —C(O)NR$^7$R$^8$, or C$_1$-C$_6$-alkyl or C$_1$-C$_6$-alkoxy which in each case is optionally, identically or differently, mono- or polysubstituted by halogen, hydroxyl, C$_1$-C$_6$-alkoxy, —CF$_3$, —OCF$_3$, or —NR$^7$R$^8$,
R$^3$ represents a C$_1$-C$_6$-alkyl or a C$_3$—C$_7$-cycloalkyl ring, which in each case is optionally, identically or differently, mono- or polysubstituted by hydroxyl, —C(O)

$OR^{11}$, —C(O)$NR^7R^8$, —$NR^7R^8$, cyano, halogen, —$CF_3$, $C_1$-$C_6$-alkoxy, —$OCF_3$ and/or $C_1$-$C_6$-alkyl,
$R^4$ represents hydrogen, —$SO_2R^{11}$, —C(O)$OR^{11}$, or —C(O)$NR^7R^8$,
X represents —$NR^5$—,
Y represents —O— or $NR^5$,
A represents
  (i) a bond or
  (ii) an aryl or heteroaryl ring, which in each case is optionally, identically or differently, mono- or polysubstituted by hydroxyl, —$NR^7R^8$, —C(O)$NR^7R^8$, cyano, halogen, $C_1$-$C_6$-alkoxy, —$OCF_3$, —$CF_3$, $C_1$-$C_6$-alkyl, $C_3$-$C_6$-cycloalkyl, and/or heterocyclyl having 3 to 8 ring atoms,
n represents 1-5,
$R^7$ and $R^8$ independently of one another represent hydrogen, or and/or a $C_1$-$C_6$-alkyl radical, $C_3$-$C_8$-cycloalkyl, aryl ring, a heterocyclyl ring having 3 to 8 ring atoms, and/or a heteroaryl ring, which in each case is optionally, identically or differently, mono- or polysubstituted by hydroxyl, —$NR^9R^{10}$, cyano, halogen, —$CF_3$, $C_1$-$C_6$-alkoxy, and/or $OCF_3$, and
$R^{11}$ represents a $C_1$-$C_3$-alkyl, a $C_3$-$C_8$-cycloalkyl, aryl ring, a heterocyclyl ring having 3 to 8 ring atoms, or a heteroaryl ring, which in each case is optionally, identically or differently, mono- or polysubstituted by hydroxyl, halogen, cyano, nitro, —$NR^7R^8$, $C_1$-$C_6$-alkyl, —$CF_3$, $C_1$-$C_6$-alkoxy, and/or —$OCF_3$.

3. A compound according to claim 1, in which
$R^1$ represents
  (i) a phenyl or monocyclic heteroaryl ring, which in each case is optionally, identically or differently, mono- or polysubstituted by hydroxyl, —$NR^6$—C(O)—$R^{11}$, cyano, or $C_1$-$C_6$-alkyl,
  (ii) a $C_1$-$C_6$-alkyl radical which is optionally, identically or differently, mono- or polysubstituted by hydroxyl, —$NR^7R^8$, $C_1$-$C_6$-alkoxy, and/or $C_3$-$C_6$-cycloalkyl, or
  (iii) a $C_3$-$C_8$ cycloalkyl ring.

4. A compound according to claim 1, in which $R^2$ represents hydrogen, halogen, cyano, —C(O)$OR^{11}$, —C(O)OH or a $C_1$-$C_6$-alkoxy radical.

5. A compound according to claim 1, in which $R^3$ represents a $C_1$-$C_3$-alkyl radical.

6. A compound according to claim 1, in which $R^4$ represents hydrogen, —$SO_2R^{11}$ or —C(O)$OR^{11}$.

7. A compound according to claim 1, in which $R^4$ represents hydrogen.

8. A compound according to claim 1, in which A represents a bond or a phenyl or monocyclic heteroaryl ring.

9. A compound according to claim 1, in which X represents —NH—.

10. A compound according to claim 1, in which $R^7$ and $R^8$ independently of one another represent a $C_1$-$C_6$-alkyl radical.

11. A compound according to claim 1, in which n represents 1-4.

12. A compound according to claim 1 in which
$R^1$ represents
  (i) a phenyl or monocyclic heteroaryl ring, which in each case is optionally, identically or differently, mono- or polysubstituted by hydroxyl, —$NR^6$—C(O)—$R^{11}$, cyano, or $C_1$-$C_6$-alkyl, or
  (ii) a $C_1$-$C_6$-alkyl radical which is optionally, identically or differently, mono- or polysubstituted by hydroxyl, —$NR^7R^8$, $C_1$-$C_6$-alkoxy, and/or $C_3$-$C_6$-cycloalkyl, or
  (iii) a $C_3$-$C_8$ cycloalkyl ring,
$R^2$ represents hydrogen, halogen, cyano, —C(O)$OR^{11}$, —C(O)OH, or $C_1$-$C_6$-alkoxy,
$R^3$ represents $C_1$-$C_6$-alkyl,
$R^4$ represents hydrogen, $SO_2R^{11}$ or —C(O)$OR^{11}$,
X represents —NH—,
Y represents —O— or —NH—,
A represents a bond, phenyl, or monocyclic heteroaryl ring,
n represents 1-4,
$R^6$ represents hydrogen,
$R^7$ and $R^8$ each represent $C_1$-$C_6$-alkyl,
$R^{11}$ represents $C_1$-$C_6$-alkyl or phenyl, which in each case is optionally substituted by nitro.

13. A process for the preparation of a compound according to claim 1, comprising

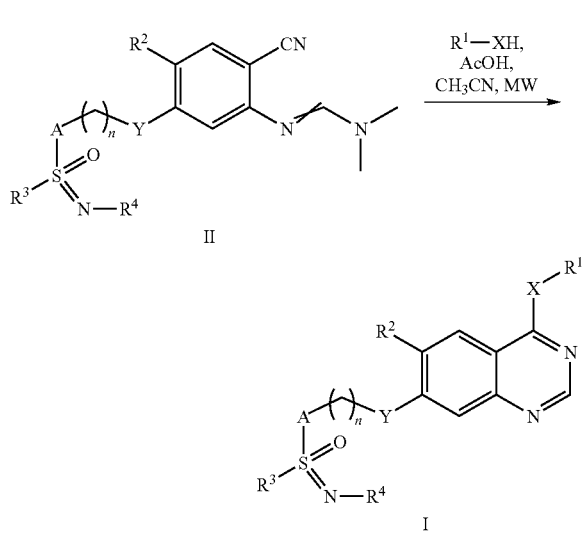

reacting an intermediate compound according to formula (II) with a compound of the formula $R^1$—XH to obtain a compound according to formula I, where $R^4$ is not hydrogen.

14. A process according to claim 13, further comprising replacing the $R^4$ group with hydrogen for the preparation of compounds with $R^4$ equal to hydrogen, characterized by subsequent removal of $R^4$ unequal to hydrogen.

15. A pharmaceutical composition comprising a compound according to claim 1 and at least one galenic excipient selected from vehicles, fillers, disintegrants, binders, moisturizers, lubricants, absorbents and adsorbents, diluents, solvents, cosolvents, emulsifiers, solubilizers, taste corrigents, colorants, preservatives, stabilizers, wetting agents, salts for changing the osmotic pressure, and buffers.

16. A compound according to claim 1, wherein
$R^1$ is an aryl or heteroaryl ring, which in each case is optionally substituted by hydroxyl, or is $C_1$-$C_6$-alkyl radical or $C_3$-$C_8$ cycloalkyl which in each case is optionally mono- or polysubstituted by —$NR^7R^8$ or $C_1$-$C_6$-alkoxy,
$R^2$ is hydrogen, halogen, —C(O)$OR^{11}$, —C(O)OH or $C_1$-$C_6$-alkoxy,
$R^3$ is $C_1$-$C_3$-alkyl radical
$R^4$ is hydrogen, —$SO_2R^{11}$, or —C(O)$OR^{11}$,
X is —NH—,
Y is —O—,
A is a bond or an aryl ring,
n is 1-4,
$R^7$ and $R^8$ are each independently of one another $C_1$-$C_6$-alkyl, $R^{11}$ is $C_1$-$C_3$-alkyl or an aryl ring, which in each case is optionally substituted by nitro.

17. A compound according to claim 1, wherein $R^9$ and $R^{10}$, independently of one another, is hydrogen or $C_1$-$C_6$-alkyl, which in each case is optionally mono- or polysubstituted by hydroxyl.

18. A compound according to claim 1, wherein $R^{11}$ is $C_1$-$C_6$-alkyl, $C_2$-$C_6$-alkenyl, $C_2$-$C_6$-alkynyl, a $C_3$-$C_8$-cycloalkyl, aryl ring, a heterocyclyl ring having 3 to 8 ring atoms, or a heteroaryl ring, which in each case is optionally mono- or polysubstituted by hydroxyl, halogen, cyano, nitro, —$NR^7R^8$, $C_1$-$C_6$-alkyl, —$CF_3$, $C_1$-$C_6$-alkoxy, and/or —$OCF_3$.

19. A compound according to claim 1, wherein said compound is selected from:

(RS)-S-[3-({[6-Bromo-4-(isopropylamino)quinazolin-7-yl]oxy}methyl)phenyl]—N-(ethoxycarbonyl)-S-ethyl-sulphoximide, (RS-S-[3-({[6-Bromo-4-(isopropylamino)quinazolin-7-yl]oxy}methyl)phenyl]-S-methylsulphoximide, (RS)-S-{3-[({6-Bromo-4-[(cyclopropylmethyl)amino]quinazolin-7-yl}oxy)methyl]-phenyl}-N-(ethoxycarbonyl)-S-methylsulphoximide, (RS)-S-{3-[({6-Bromo-4-[(cyclopropylmethyl)amino]quinazolin-7-yl}oxy)methyl]phenyl}-S-methylsulphoximide, (RS)-S-{3-[({6-Bromo-4-[(4-hydroxyphenyl)amino]quinazolin-7-yl}oxy)methyl]-phenyl}-N-(ethoxycarbonyl)-S-methylsulphoximide, (RS)-S-[3-({[6-Bromo-4-(1H-pyrazol-3-ylamino)quinazolin-7-yl]oxy}methyl)-phenyl]—N-(ethoxycarbonyl)-S-methylsulphoximide, (RS)-S-[3-({[6-Bromo-4-(1H-pyrazol-3-ylamino)quinazolin-7-yl]oxy}methyl)-phenyl]-S-methylsulphoximide, (RS)-S-{3-[({6-Bromo-4-[(2-methoxyethyl)amino]quinazolin-7-yl}oxy)methyl]-phenyl}-N-(ethoxycarbonyl)-S-ethylsulphoximide, (RS)-S-{3-[({6-Bromo-4-[(2-methoxyethyl)amino]quinazolin-7-yl}oxy)methyl]-phenyl}-S-methylsulphoximide, (RS)-S-(3-{[(6-Bromo-4-{[2-(dimethylamino)ethyl]amino}quinazolin-7-yl)oxy]-methyl}phenyl)-N-(ethoxycarbonyl)-S-methylsulphoximide, (RS)-S-(3-{[(6-Bromo-4-{[2-(dimethylamino)ethyl]amino}quinazolin-7-yl)oxy]-methyl}phenyl)-S-methylsulphoximide, (RS)-S-[3-({[6-Bromo-4-(cyclopropylamino)quinazolin-7-yl]oxy}methyl)phenyl]-N-(ethoxycarbonyl)-S-methylsulphoximide, (RS)-S-[3-({[6-Bromo-4-(cyclopropylamino)quinazolin-7-yl]oxy}methyl)phenyl]-S-methylsulphoximide, (RS)-S-[3-({[6-Bromo-4-(cyclobutylamino)quinazolin-7-yl]oxy}methyl)phenyl]-N-(ethoxycarbonyl)-S-methylsulphoximide, (RS)-S-[3-({[6-Bromo-4-(cyclobutylamino)quinazolin-7-yl]oxy}methyl)phenyl]-S-methylsulphoximide, Ethyl 7-({(RS)-3-[N-(ethoxycarbonyl)-S-methylsulphonimidoyl]benzyl}oxy)-4-(isopropylamino)quinazoline-6-carboxylate, 4-(Isopropylamino)-7-{[(RS)-3-(S-methylsulphonimidoyl)benzyl]oxy}-quinazoline-6-carboxylic acid, (RS)-S-[3-({[6-Bromo-4-(1,3,4-thiadiazol-2-ylamino)quinazolin-7-yl]oxy}methyl)-phenyl]-S-methylsulphoximide, (RS)-S-[3-({[4-(Cyclopropylamino)-6-methoxyquinazolin-7-yl]oxy}methyl)phenyl]-N-(ethoxycarbonyl)-S-methylsulphoximide, (RS)-S-[3-({[4-(Cyclopropylamino)-6-methoxyquinazolin-7-yl]oxy}methyl)phenyl]-S-methylsulphoximide, (RS)-S-[3-({[4-(Cyclobutylamino)-6-methoxyquinazolin-7-yl]oxy}methyl)phenyl]-N-(ethoxycarbonyl)-S-methylsulphoximide, (RS)-S-[3-({[4-(Cyclobutylamino)-6-methoxyquinazolin-7-yl]oxy}methyl)phenyl]-S-methylsulphoximide, (RS)-N-(Ethoxycarbonyl)-S-methyl-S-[3-({[6-methoxy-4-(4-pyridylamino)-quinazolin-7-yl]oxy}methyl)phenyl]sulphoximide, (RS)-S-[3-({[6-Methoxy-4-(4-pyridylamino)quinazolin-7-yl]oxy}methyl)phenyl]-S-methylsulphoximide, (RS)-N-(Ethoxycarbonyl)-S-methyl-S-[3-({[6-methoxy-4-(3-pyridylamino)-quinazolin-7-yl]oxy}methyl)phenyl]sulphoximide, (RS)-S-[3-({[6-Methoxy-4-(3-pyridylamino)quinazolin-7-yl]oxy}methyl)-phenyl]-S-methylsulphoximide, (RS)-N-(Ethoxycarbonyl)-S-methyl-S-[3-({[6-methoxy-4-(thiazol-2-ylamino)-chinazolin-7-yl]oxy}methyl)phenyl]sulphoximide, (RS)-S-[3-({[6-Methoxy-4-(thiazol-2-yl-amino)quinazolin-7-yl]oxy}methyl)-phenyl]-S-methylsulphoximide, (RS)-N-(Ethoxycarbonyl)-S-methyl-S-[3-({[6-methoxy-4-(1,3,4-thiadiazol-2-ylamino)quinazolin-7-yl]oxy}methyl)phenyl]sulphoximide, (RS)-S-[3-({[6-Methoxy-4-(1,3,4-thiadiazol-2-ylamino)quinazolin-7-yl]oxy}-methyl)phenyl]-S-methylsulphoximide, (RS)-S-[3-({[4-(Cyclopropylamino)-6-methoxyquinazolin-7-yl]oxy}methyl)phenyl]-N-(ethoxycarbonyl)-S-ethylsulphoximide, (RS)-S-[3-({[4-(Cyclopropylamino)-6-methoxyquinazolin-7-yl]oxy}methyl)phenyl]-S-ethylsulphoximide, (RS)-S-[3-({[4-(Cyclobutylamino)-6-methoxyquinazolin-7-yl]oxy}methyl)phenyl]-N-(ethoxycarbonyl)-S-ethylsulphoximide, (RS)-S-[3-({[4-(Cyclobutylamino)-6-methoxyquinazolin-7-yl]oxy}methyl)phenyl]-S-ethylsulphoximide, (RS)-N-(Ethoxycarbonyl)-S-ethyl-S-[3-({[6-methoxy-4-(thiazol-2-ylamino)-quinazolin-7-yl]oxy}methyl)phenyl]sulphoximide, (RS)-S-Ethyl-S-[3-({[6-methoxy-4-(thiazol-2-ylamino)quinazolin-7-yl]oxy}-methyl)phenyl]sulphoximide, (RS)-S-Ethyl-S [3-({[6-methoxy-4-(1H-pyrazol-3-ylamino)quinazolin-7-yl]oxy}-methyl)phenyl]sulphoximide, (RS)-S-Ethyl—S [3-({[6-methoxy-4-(oxazo-3-ylamino)quinazolin-7-yl]oxy}-methyl)phenyl]sulphoximide, (RS)-S-[3-({[6-Methoxy-4-(oxazo-3-ylamino)quinazolin-7-yl]oxy}methyl)phenyl]-S-methylsulphoximide, (RS)-S-(3-{[(6-Bromo-4-{[2-hydroxy-1-(hydroxymethyl)ethyl]amino}quinazolin-7-yl)oxy]methyl}phenyl)-N-(ethoxycarbonyl)-S-methylsulphoximide, (RS)-S-(3-{[(6-Bromo-4-{[2-hydroxy-1-(hydroxymethyl)ethyl]amino}quinazolin-7-yl)oxy]methyl}phenyl)-S-methylsulphoximide, (RS)-S-[3-({[6-Bromo-4-(2-hydroxyethylamino)quinazolin-7-yl]oxy}methyl)phenyl]-N-(ethoxycarbonyl)-S-methylsulphoximide, (RS)-S-[3-({[6-Bromo-4-(2-hydroxyethylamino)quinazolin-7-yl]oxy}methyl)phenyl]-S-methylsulphoximide, (RS)-N-(Ethoxycarbonyl)-S-methyl-S-[4-({[6-methoxy-4-(3-pyridylamino)-quinazolin-7-yl]oxy}methyl)phenyl]sulphoximide,
(RS)-S-[4-({[6-Methoxy-4-(3-pyridylamino)quinazolin-7-yl]oxy}methyl)phenyl]-S-methylsulphoximide,
(RS)-N-(Ethoxycarbonyl)-S-methyl-S-[4-({[6-methoxy-4-(1,3,4-thiadiazol-2-yl-amino)quinazolin-7-yl]oxy}ethyl)phenyl]sulphoximide,
(RS)-S-[4-({[6-Methoxy-4-(1,3,4-thiadiazol-2-ylamino)quinazolin-7-yl]oxy}-methyl)phenyl]-S-methylsulphoximide,
(RS)-S-[3-({[4-(Cyclopropylamino)quinazolin-7-yl]amino}methyl)phenyl]-N-(ethoxycarbonyl)-S-methylsulphoximide,
(RS)-S-[3-({[4-(Cyclopropylamino)quinazolin-7-yl]amino}methyl)phenyl]-S-methylsulphoximide,
(RS)-N-(Ethoxycarbonyl)-S-methyl-S-[3-({[4-(3-pyridylamino)quinazolin-7-yl]-amino}methyl)phenyl]sulphoximide,
(RS)-S-Methyl-S-[3-({[4-(3-pyridylamino)quinazolin-7-yl]amino}methyl)phenyl]-sulphoximide,
(RS)-S-[3-({[4-(Isopropylamino)quinazolin-7-yl]amino}methyl)phenyl]-S-methylsulphoximide,
(RS)-S-Methyl-S-[3-({[4-(1,3,4-thiadiazol-2-ylamino)quinazolin-7-yl]amino}-methyl)phenyl]sulphoximide,
(RS)-N-(Ethoxycarbonyl)-S-methyl-S-[3-({[4-(thiazol-2-ylamino)quinazolin-7-yl]-amino}methyl)phenyl]sulphoximide,
(RS)-S-Methyl-S-[3-({[4-(thiazol-2-ylamino)quinazolin-7-yl]amino}methyl)-phenyl]sulphoximide,
(RS)-S-[3-({[6-Bromo-4-(isopropylamino)quinazolin-7-yl]amino}methyl)phenyl]-N-(ethoxycarbonyl)-S-methylsulphoximide,
(RS)-S-[3-({[6-Bromo-4-(isopropylamino)quinazolin-7-yl]amino}methyl)phenyl]-S-methylsulphoximide,
(RS)-N-(Ethoxycarbonyl)-S-methyl-S-[3-({[4-(2-methyl-5-pyridylamino)-6-methoxyquinazolin-7-yl]oxy}methyl)phenyl]sulphoximide,
(RS)-S-[3-({[4-(2-Methyl-5-pyridylamino)-6-methoxyquinazolin-7-yl]oxy}methyl)-phenyl]-S-methylsulphoximide,
(RS)-S-{3-[({4-[(3-Cyanophenyl)amino]-6-methoxyquinazolin-7-yl}oxy)methyl]phenyl}-N-(ethoxycarbonyl)-S-methylsulphoximide,
(RS)-S-{3-[({4-[(3-Cyanophenyl)amino]-6-methoxyquinazolin-7-yl}oxy)methyl]phenyl}-S-methylsulphoximide,
(RS)-N-(Ethoxycarbonyl)-S-methyl-S-[3-({[4-(2-methyl-4-pyridylamino)-6-methoxyquinazolin-7-yl]oxy}methyl)phenyl]sulphoximide,
(RS)-S-[3-({[4-(2-Methyl-4-pyridylamino)-6-methoxyquinazolin-7-yl]oxy}methyl)-phenyl]-S-methylsulphoximide,
N-{2-[(6-Bromo-7-{3-[(RS)-N-(ethoxycarbonyl)-S-methylsulphonimidoyl]-benzyloxy}quinazolin-4-yl)amino]ethyl}acetamide,
N-{2-[(6-Bromo-7-{3-[(RS)-S-methylsulphonimidoyl]benzyloxy}quinazolin-4-yl)-amino]ethyl}acetamide,
(RS)-S-[3-({[6-Bromo-4-(ethylamino)quinazolin-7-yl]oxy}methyl)phenyl]-N-(ethoxycarbonyl)-S-methylsulphoximide,
(RS)-S-[3-({[6-Bromo-4-(ethylamino)quinazolin-7-yl]oxy}methyl)phenyl]-S-methylsulphoximide,
(RS)-S-{3-[({6-Bromo-4-[(3-hydroxy-2,2-dimethylpropyl)amino]quinazolin-7-yl}-oxy)methyl]phenyl}-S-methylsulphoximide,
(RS)-S-(3-{[(6-Bromo-4-{[(RS)-2-hydroxy-1-methylethyl]amino}quinazolin-7-yl)-oxy]methyl}phenyl)-S-methylsulphoximide,
(RS)-S-(3-{[(6-Bromo-4-{[(S)-2-hydroxypropyl]amino}quinazolin-7-yl)oxy]-methyl}phenyl)-N-(ethoxycarbonyl)-S-methylsulphoximide,
(RS)-S-(3-{[(6-Bromo-4-{[(R)-2-hydroxypropyl]amino}quinazolin-7-yl)oxy]-methyl}phenyl)-S-methylsulphoximide,
(RS)-S-(3-{[(6-Bromo-4-{[(R)-2-hydroxypropyl]amino}quinazolin-7-yl)oxy]methyl}-phenyl)-N-(ethoxycarbonyl)-S-methylsulphoximide,
(RS)-S-(3-{[(6-Bromo-4-{[(R)-2-hydroxypropyl]amino}quinazolin-7-yl)oxy]-methyl}phenyl)-S-methylsulphoximide,
and pharmaceutically acceptable salts thereof.

20. A compound according to claim 1, wherein said compound is selected from:
(RS)-N-(Ethoxycarbonyl)-S-[3-({[4-(isopropylamino)quinazolin-7-yl]oxy}methyl)-phenyl]-S-methylsulphoximide,
(RS)-S-[3-({[4-(Isopropylamino)quinazolin-7-yl]oxy}methyl)phenyl]-S-methyl-sulphoximide,
Ethyl 7-({(RS)-3-[N-(ethoxycarbonyl)-S-methylsulphonimidoyl]benzyl}oxy)-4-(thiazol-2-ylamino)quinazoline-6-carboxylate,
Ethyl 7-{[(RS)-3-(S-methylsulphonimidoyl)benzyl]oxy}-4-(thiazol-2-ylamino)-quinazoline-6-carboxylate,
(RS)-N-(Ethoxycarbonyl)-S-[3-({[4-(isopropylamino)-6-methoxyquinazolin-7-yl]oxy}methyl)phenyl]-S-methylsulphoximide,
(RS)-S-[3-({[4-(Isopropylamino)-6-methoxyquinazolin-7-yl]oxy}methyl)phenyl]-S-methylsulphoximide,
(RS)-S-[4-({[6-Bromo-4-(isopropylamino)quinazolin-7-yl]oxy}methyl)phenyl]-N-(ethoxycarbonyl)-S-methylsulphoximide,
(RS)-S-[4-({[6-Bromo-4-(isopropylamino)quinazolin-7-yl]oxy}methyl)phenyl]-S-methylsulphoximide,
(RS)-N-(Ethoxycarbonyl)-S-ethyl-S-[3-({[4-(isopropylamino)-6-methoxyquinazolin-7-yl]oxy}methyl)phenyl]sulphoximide,
(RS)-S-Ethyl-S-[3-({[4-(isopropylamino)-6-methoxyquinazolin-7-yl]oxy}-methyl)phenyl]sulphoximide,
(RS)-S-[3-({[6-Cyano-4-(isopropylamino)quinazolin-7-yl]oxy}methyl)phenyl]-N-(ethoxycarbonyl)-S-methylsulphoximide,
(RS)-S-[3-({[6-Cyano-4-(isopropylamino)quinazolin-7-yl]oxy}methyl)phenyl]-S-methylsulphoximide,
and pharmaceutically acceptable salts thereof.

21. A compound according to claim 1, wherein said compound is selected from:
(RS)-S-(4-{[4-(Isopropylamino)-6-methoxyquinazolin-7-yl]oxy}butyl)-S-methyl-N-[(4-nitrophenyl)sulphonyl]sulphoximide,
(RS)-S-(4-{[4-(Isopropylamino)-6-methoxyquinazolin-7-yl]oxy}butyl)-S-methyl-sulphoximide,
(RS)-S-(4-{[4-(Isopropylamino)-6-methoxyquinazolin-7-yl]oxy}propyl)-S-methyl-N-[(4-nitrophenyl)sulphonyl]sulphoximide,
(RS)-S-(4-{[4-(Isopropylamino)-6-methoxyquinazolin-7-yl]oxy}propyl)-S-methyl-sulphoximide,
Ethyl 4-(isopropylamino)-7-[(RS)-3-{S-methyl-N-[(4-nitrophenyl)sulphonyl]-sulphonimidoyl}propoxy]quinazoline-6-carboxylate,
Ethyl 4-(isopropylamino)-7-[(RS)-3-(S-methylsulphonimidoyl)propoxy]-quinazoline-6-carboxylate, (RS)-S-[4-({[6-Bromo-4-(isopropylamino)quinazolin-7-yl]oxy}methyl)pyridin-3-yl]-S-methylsulphoximide,
and pharmaceutically acceptable salts thereof.

22. A compound according to claim 19, wherein said compound is selected from:
   (RS)-S-[3-({[6-Bromo-4-(isopropylamino)quinazolin-7-yl]oxy}methyl)phenyl]-N-(ethoxycarbonyl)-S-methylsulphoximide,
   (RS)-S-[3-({[6-Bromo-4-(isopropylamino)quinazolin-7-yl]oxy}methyl)phenyl]-S-methylsulphoximide,
   (RS)-S-{3-[({6-Bromo-4-[(cyclopropylmethyl)amino]quinazolin-7-yl}oxy)methyl]-phenyl}-N-(ethoxycarbonyl)-S-methylsulphoximide,
   (RS)-S-{3-[({6-Bromo-4-[(cyclopropylmethyl)amino]quinazolin-7-yl}oxy)methyl]-phenyl}-S-methylsulphoximide,
   (RS)-S-{3-[({6-Bromo-4-[(4-hydroxyphenyl)amino]quinazolin-7-yl}oxy)methyl]-phenyl}-N-(ethoxycarbonyl)-S-methylsulphoximide,
   (RS)-S-[3-({[6-Bromo-4-(1H-pyrazol-3-ylamino)quinazolin-7-yl]oxy}methyl)-phenyl]-N-(ethoxycarbonyl)-S-methylsulphoximide,
   (RS)-S-[3-({[6-Bromo-4-(1H-pyrazol-3-ylamino)quinazolin-7-yl]oxy}methyl)-phenyl]-S-methylsulphoximide,
   (RS)-S-{3-[({6-Bromo-4-[(2-methoxyethyl)amino]quinazolin-7-yl}oxy)methyl]-phenyl}-N-(ethoxycarbonyl)-S-methylsulphoximide,
   (RS)-S-{3-[({6-Bromo-4-[(2-methoxyethyl)amino]quinazolin-7-yl}oxy)methyl]-phenyl}-S-methylsulphoximide,
   (RS)-S-(3-{[(6-Bromo-4-{[2-(dimethylamino)ethyl]amino}quinazolin-7-yl)oxy]-methyl}phenyl)-N-(ethoxycarbonyl)-S-methylsulphoximide,
   (RS)-S-(3-{[(6-Bromo-4-{[2-(dimethylamino)ethyl]amino}quinazolin-7-yl)oxy]-methyl}phenyl)-S-methylsulphoximide,
   (RS)-S-[3-({[6-Bromo-4-(cyclopropylamino)quinazolin-7-yl]oxy}methyl)phenyl]-N-(ethoxycarbonyl)-S-methylsulphoximide,
   (RS)-S-[3-({[6-Bromo-4-(cyclopropylamino)quinazolin-7-yl]oxy}methyl)phenyl]-S-methylsulphoximide,
   (RS)-S-[3-({[6-Bromo-4-(cyclobutylamino)quinazolin-7-yl]oxy}methyl)phenyl]-N-(ethoxycarbonyl)-S-methylsulphoximide,
   (RS)-S-[3-({[6-Bromo-4-(cyclobutylamino)quinazolin-7-yl]oxy}methyl)phenyl]-S-methylsulphoximide,
   (RS)-S-[3-({[6-Bromo-4-(1,3,4-thiadiazol-2-ylamino)quinazolin-7-yl]oxy}methyl)-phenyl]-S-methylsulphoximide,
   (RS)-S-(3-{[(6-Bromo-4-{[2-hydroxy-1-(hydroxymethyl)ethyl]amino}quinazolin-7-yl)oxy]methyl}phenyl)-N-(ethoxycarbonyl)-S-methylsulphoximide,
   (RS)-S-(3-{[(6-Bromo-4-{[2-hydroxy-1-(hydroxymethyl)ethyl]amino}quinazolin-7-yl)oxy]methyl}phenyl)-S-methylsulphoximide,
   (RS)-S-[3-({[6-Bromo-4-(2-hydroxyethylamino)quinazolin-7-yl]oxy}methyl)phenyl]-N-(ethoxycarbonyl)-S-methylsulphoximide,
   (RS)-S-[3-({[6-Bromo-4-(2-hydroxyethylamino)quinazolin-7-yl]oxy}methyl)phenyl]-S-methylsulphoximide,
   (RS)-S-[3-({[6-Bromo-4-(isopropylamino)quinazolin-7-yl]amino}methyl)phenyl]-N-(ethoxycarbonyl)-S-methylsulphoximide,
   (RS)-S-[3-({[6-Bromo-4-(isopropylamino)quinazolin-7-yl]amino}methyl)phenyl]-S-methylsulphoximide,
   N-{2-[(6-Bromo-7-{3-[(RS)-N-(ethoxycarbonyl)-S-methylsulphonimidoyl]-benzyloxy}quinazolin-4-yl)amino]ethyl}acetamide,
   N-{2-[(6-Bromo-7-{3-[(RS)-S-methylsulphonimidoyl]benzyloxy}quinazolin-4-yl)-amino]ethyl}acetamide,
   (RS)-S-[3-({[6-Bromo-4-(ethylamino)quinazolin-7-yl]oxy}methyl)phenyl]-N-(ethoxycarbonyl)-S-methylsulphoximide,
   (RS)-S-[3-({[6-Bromo-4-(ethylamino)quinazolin-7-yl]oxy}methyl)phenyl]-S-methylsulphoximide,
   (RS)-S-{3-[({6-Bromo-4-[(3-hydroxy-2,2-dimethylpropyl)amino]quinazolin-7-yl}-oxy)methyl]phenyl}-S-methylsulphoximide,
   (RS)-S-(3-{[(6-Bromo-4-{[(RS)-2-hydroxy-1-methylethyl]amino}quinazolin-7-yl)-oxy]methyl}phenyl)-S-methylsulphoximide,
   (RS)-S-(3-{[(6-Bromo-4-{[(S)-2-hydroxypropyl]amino}quinazolin-7-yl)oxy]methyl}phenyl)-N-(ethoxycarbonyl)-S-methylsulphoximide,
   (RS)-S-(3-{[(6-Bromo-4-{[(S)-2-hydroxypropyl]amino}quinazolin-7-yl)oxy]-methyl}phenyl)-S-methylsulphoximide,
   (RS)-S-(3-{[(6-Bromo-4-{[(R)-2-hydroxypropyl]amino}quinazolin-7-yl)oxy]methyl}-phenyl)-N-(ethoxycarbonyl)-S-methylsulphoximide,
   (RS)-S-(3-{[(6-Bromo-4-{[(R)-2-hydroxypropyl]amino}quinazolin-7-yl)oxy]-methyl}phenyl)-S-methylsulphoximide,
   and pharmaceutically acceptable salts thereof.

23. A compound according to claim 19, wherein said compound is selected from:
   Ethyl 7-({(RS)-3-[N-(ethoxycarbonyl)-S-methylsulphonimidoyl]benzyl}oxy)-4-(isopropylamino)quinazoline-6-carboxylate,
   4-(Isopropylamino)-7-{[(RS)-3-(S-methylsulphonimidoyl)benzyl]oxy}-quinazoline-6-carboxylic acid,
   (RS)-S-[3-({[4-(Cyclopropylamino)-6-methoxyquinazolin-7-yl]oxy}methyl)phenyl]-N-(ethoxycarbonyl)-S-methylsulphoximide,
   (RS)-S-[3-({[4-(Cyclopropylamino)-6-methoxyquinazolin-7-yl]oxy}methyl)phenyl]-S-methylsulphoximide,
   (RS)-S-[3-({[4-(Cyclobutylamino)-6-methoxyquinazolin-7-yl]oxy}methyl)phenyl]-N-(ethoxycarbonyl)-S-methylsulphoximide,
   (RS)-S-[3-({[4-(Cyclobutylamino)-6-methoxyquinazolin-7-yl]oxy}methyl)phenyl]-S-methylsulphoximide,
   (RS)-N-(Ethoxycarbonyl)-S-methyl-S-[3-({[6-methoxy-4-(4-pyridylamino)-quinazolin-7-yl]oxy}methyl)phenyl]sulphoximide,
   (RS)-S-[3-({[6-Methoxy-4-(4-pyridylamino)quinazolin-7-yl]oxy}methyl)phenyl]-S-methylsulphoximide,
   (RS)-N-(Ethoxycarbonyl)-S-methyl-S-[3-({[6-methoxy-4-(3-pyridylamino)-quinazolin-7-yl]oxy}methyl)phenyl]sulphoximide,
   (RS)-S-[3-({[6-Methoxy-4-(3-pyridylamino)quinazolin-7-yl]oxy}methyl)-phenyl]-S-methylsulphoximide,
   (RS)-N-(Ethoxycarbonyl)-S-methyl-S-[3-({[6-methoxy-4-(thiazol-2-ylamino)-chinazolin-7-yl]oxy}methyl)phenyl]sulphoximide,
   (RS)-S-[3-({[6-Methoxy-4-(thiazol-2-yl-amino)quinazolin-7-yl]oxy}methyl)-phenyl]-S-methylsulphoximide,
   (RS)-N-(Ethoxycarbonyl)-S-methyl-S-[3-({[6-methoxy-4-(1,3,4-thiadiazol-2-ylamino)quinazolin-7-yl]oxy}methyl)phenyl]sulphoximide, (RS)-S-[3-({[6-Methoxy-4-(1,3,4-thiadiazol-2-ylamino)quinazolin-7-yl]oxy}-methyl)phenyl]-S-methylsulphoximide, (RS)-S-[3-({[4-(Cyclopropylamino)-6-methoxyquinazolin-7-yl]oxy}methyl)phenyl]-N-(ethoxycarbonyl)-S-ethylsulphoximide, (RS)-S-[3-({[4-(Cyclopropylamino)-6-methoxyquinazolin-7-yl]oxy}methyl)phenyl]-S-ethylsulphoximide, (RS)-S-[3-({[4-(Cyclobutylamino)-6-methoxyquinazolin-7-yl]oxy}methyl)phenyl]-N-(ethoxycarbonyl)-S-ethylsulphoximide, (RS)-S-[3-({[4-(Cyclobutylamino)-6-methoxyquinazolin-7-yl]oxy}methyl)phenyl]-S-ethylsulphoximide, (RS)-N-(Ethoxycarbonyl)-S-ethyl-S-[3-({[6-methoxy-4-(thiazol-2-ylamino)-quinazolin-7-yl]oxy}methyl)phenyl]sulphoximide, (RS)-S-Ethyl-S-[3-({[6-methoxy-4-(thiazol-2-ylamino)quinazolin-7-yl]oxy}-methyl)phenyl]sulphoximide, (RS)-S-Ethyl-S-[3-({[6-methoxy-4-(1H-pyrazol-3-ylamino)quinazolin-7-yl]oxy}-methyl)phenyl]sulphoximide, (RS)-S-Ethyl-S-[3-({[6-methoxy-4-(oxazo-3-ylamino)quinazolin-7-yl]oxy}-methyl)phenyl]sulphoximide, (RS)-S-[3-({[6-Methoxy-4-(oxazo-3-ylamino)quinazolin-7-yl]oxy}methyl)phenyl]-S-methylsulphoximide, (RS)-N-(Ethoxycarbonyl)-S-methyl-S-[4-({[6-methoxy-4-(3-pyridylamino)-quinazolin-7-yl]oxy}methyl)phenyl]sulphoximide, (RS)-S-[4-({[6-methoxy-4-(3-pyridylamino)quinazolin-7-yl]oxy}methyl)phenyl]-S-methylsulphoximide, (RS)-N-(Ethoxycarbonyl)-S-methyl-S-[4-({[6-methoxy-4-(1,3,4-thiadiazol-2-yl-amino)quinazolin-7-yl]oxy}methyl)phenyl]sulphoximide, (RS)-S-[4-({[6-Methoxy-4-(1,3,4-thiadiazol-2-ylamino)quinazolin-7-yl]oxy}-methyl)phenyl]-S-methylsulphoximide, (RS)-S-[3-({[4-(Cyclopropylamino)quinazolin-7-yl]amino}methyl)phenyl]-N-(ethoxycarbonyl)-S-methyl-sulphoximide, (RS)-S-[3-({[4-(Cyclopropylamino)quinazolin-7-yl]amino}methyl)phenyl]-S-methylsulphoximide, (RS)-N-(Ethoxycarbonyl)-S-methyl-S-[3-({[4-(3-pyridylamino)quinazolin-7-yl]-amino}methyl)phenyl]sulphoximide, (RS)-S-Methyl-S-[3-({[4-(3-pyridylamino)quinazolin-7-yl]amino}methyl)phenyl]-sulphoximide, (RS)-S-[3-({[4-(Isopropylamino)quinazolin-7-yl]amino}methyl)phenyl]-S-methylsulphoximide, (RS)-S-Methyl-S-[3-({[4-({1,3,4-thiadiazol-2-ylamino)quinazolin-7-yl]amino}-methyl)phenyl]sulphoximide, (RS)-N-(Ethoxycarbonyl)-S-methyl-S-[3-({[4-(thiazol-2-ylamino)quinazolin-7-yl]-amino}methyl)phenyl]sulphoximide, (RS)-S-Methyl-S-[3-({[4-(thiazol-2-ylamino)quinazolin-7-yl]amino}methyl)-phenyl]sulphoximide, (RS)-N-(Ethoxycarbonyl)-S-methyl-S-[3-({[4-(2-methyl-5-pyridylamino)-6-methoxyquinazolin-7-yl]oxy}methyl)phenyl]sulphoximide, (RS)-S-[3-({[4-(2-Methyl-5-pyridylamino)-6-methoxyquinazolin-7-yl]oxy}methyl)-phenyl]-S-methylsulphoximide, (RS)-S-{3-[({4-[(3-Cyanophenyl)amino]-6-methoxyquinazolin-7-yl}oxy)methyl]phenyl}-N-(ethoxycarbonyl)-S-methylsulphoximide, (RS)-S-{3-[({4-[(3-Cyanophenyl)amino]-6-methoxyquinazolin-7-yl}oxy)methyl]phenyl}-S-methylsulphoximide, (RS)-N-(Ethoxycarbonyl)-S-methyl-S-[3-({[4-(2-methyl-4-pyridylamino)-6-methoxyquinazolin-7-yl]oxy}methyl)phenyl]sulphoximide, (RS)-S-[3-({[4-(2-Methyl-4-pyridylamino)-6-methoxyquinazolin-7-yl]oxy}methyl)-phenyl]-S-methylsulphoximide, and pharmaceutically acceptable salts thereof.

\* \* \* \* \*